US010636527B2

(12) United States Patent
Pulitzer et al.

(10) Patent No.: US 10,636,527 B2
(45) Date of Patent: Apr. 28, 2020

(54) SYSTEM AND METHOD FOR QUANTIFYING, ENSURING, AND TRIGGERING THE PRESCRIPTIVE AUTHORITY FOR A TELEMEDICINE SESSION

(71) Applicant: RELIANT IMMUNE DIAGNOSTICS, INC., Austin, TX (US)

(72) Inventors: Jovan Hutton Pulitzer, Frisco, TX (US); Henry Joseph Legere, Austin, TX (US)

(73) Assignee: RELIANT IMMUNE DIAGNOSTICS, INC., Austin, TX (US)

( * ) Notice: Subject to any disclaimer, the term of this patent is extended or adjusted under 35 U.S.C. 154(b) by 0 days.

(21) Appl. No.: 16/014,643

(22) Filed: Jun. 21, 2018

(65) Prior Publication Data
US 2019/0378624 A1 Dec. 12, 2019

Related U.S. Application Data

(60) Provisional application No. 62/681,602, filed on Jun. 6, 2018.

(51) Int. Cl.
*G16H 80/00* (2018.01)
*G16H 50/20* (2018.01)
(Continued)

(52) U.S. Cl.
CPC ............. *G16H 80/00* (2018.01); *G16H 10/65* (2018.01); *G16H 20/10* (2018.01); *G16H 50/20* (2018.01); *G16H 15/00* (2018.01); *G16H 50/70* (2018.01)

(58) Field of Classification Search
CPC ........ G16H 50/20; G16H 80/00; G06F 19/34; G06F 19/3418
See application file for complete search history.

(56) References Cited

U.S. PATENT DOCUMENTS 5,587,061 A 12/1996 Chen
5,709,788 A 1/1998 Chen
(Continued)

FOREIGN PATENT DOCUMENTS

CN 105954512 A 9/2016
WO 2010118124 A2 10/2010
(Continued)

OTHER PUBLICATIONS

Health Information Standards Committee for Alberta, Laboratory Results Delivery Message Specification; Sep. 2, 2009; Health Information Messaging Standard, Version 2.0, pp. 4-47 (Year: 2009).*

(Continued)

*Primary Examiner* — Evangeline Barr

(57) ABSTRACT

A method for creating a unique transaction ID (UTID) securely representing a medical diagnostic transaction between a user/patient and a telemedicine professional is provided. The method includes receiving test information to initiate a new diagnostic transaction, initiating generation of a UTID for the new diagnostic transaction initiated by the receive operation for storage of any transaction information associated therewith, and receiving a request for a telemedicine session and in response thereto executing the following steps: analyzing the test results with an expert system, contacting a telemedicine professional and transmitting predetermined information from the first central office database including at least the test results and determined treatment regimens determined by the expert system, and receiving (Continued)

approval from the telemedicine professional of a selection of the determined treatment regimen.

20 Claims, 39 Drawing Sheets

(51) Int. Cl.
  *G16H 20/10* (2018.01)
  *G16H 10/65* (2018.01)
  *G16H 50/70* (2018.01)
  *G16H 15/00* (2018.01)

(56) References Cited

U.S. PATENT DOCUMENTS

| | | | |
|---|---|---|---|
| 5,904,826 A | 5/1999 | Chen | |
| 6,081,786 A * | 6/2000 | Barry | G06F 19/3456 705/3 |
| 6,149,865 A | 11/2000 | Hsu | |
| 7,090,802 B1 | 8/2006 | Wang | |
| 7,235,098 B2 | 6/2007 | Palmaz | |
| 8,308,452 B2 | 11/2012 | Amirouche et al. | |
| 8,506,901 B2 | 8/2013 | Chen et al. | |
| 8,655,009 B2 | 2/2014 | Chen et al. | |
| 8,807,169 B2 | 8/2014 | Amirouche et al. | |
| 8,877,140 B2 | 11/2014 | Chen et al. | |
| 8,911,679 B2 | 12/2014 | Chen et al. | |
| 9,285,323 B2 | 3/2016 | Burg et al. | |
| 9,390,237 B2 | 6/2016 | Myers et al. | |
| 9,523,358 B2 | 12/2016 | Amirouche et al. | |
| 9,569,858 B2 | 2/2017 | Babcock et al. | |
| 9,607,380 B2 | 3/2017 | Burg et al. | |
| 9,726,161 B2 | 8/2017 | Kim et al. | |
| 9,805,165 B2 * | 10/2017 | Xiang | G01N 33/48792 |
| 2002/0029350 A1 * | 3/2002 | Cooper | G06Q 10/10 726/26 |
| 2002/0134682 A1 | 9/2002 | Chen | |
| 2003/0207458 A1 | 11/2003 | Sookbumroong | |
| 2005/0266582 A1 | 12/2005 | Modlin et al. | |
| 2006/0014302 A1 | 1/2006 | Martinez | |
| 2006/0222567 A1 | 10/2006 | Kloepfer et al. | |
| 2006/0245933 A1 | 11/2006 | Balch | |
| 2007/0124278 A1 * | 5/2007 | Lewis, Jr. | G06F 19/28 |
| 2008/0070599 A1 | 3/2008 | Apodaca | |
| 2008/0118397 A1 | 5/2008 | Slowey | |
| 2009/0298191 A1 | 12/2009 | Whitesides et al. | |
| 2011/0077971 A1 | 3/2011 | Surwit | |
| 2012/0082598 A1 | 4/2012 | Baydoun | |
| 2013/0161190 A1 | 6/2013 | Ewart et al. | |
| 2013/0189794 A1 | 7/2013 | Emeric et al. | |
| 2013/0273528 A1 | 10/2013 | Ehrenkranz | |
| 2014/0051173 A1 | 2/2014 | Barstis et al. | |
| 2014/0072189 A1 | 3/2014 | Jena | |
| 2014/0089006 A1 | 3/2014 | Abreu | |
| 2014/0121487 A1 | 5/2014 | Faybishenko et al. | |
| 2014/0170679 A1 | 6/2014 | Aitchison | |
| 2015/0056719 A1 | 2/2015 | Karlovac | |
| 2015/0359458 A1 | 12/2015 | Erickson et al. | |
| 2016/0077091 A1 | 3/2016 | Tyrrell et al. | |
| 2016/0223536 A1 | 8/2016 | Johnson et al. | |
| 2017/0059566 A1 | 3/2017 | Reed et al. | |
| 2017/0061074 A1 * | 3/2017 | Singh | G06F 19/3418 |
| 2017/0089893 A1 | 3/2017 | Legere, III | |

FOREIGN PATENT DOCUMENTS

| | | |
|---|---|---|
| WO | 2013158504 A1 | 10/2013 |
| WO | 2015143309 A1 | 9/2015 |

OTHER PUBLICATIONS

Jianjun Li et al. Application of Microfluidic Devices to Proteomics Research. Journal: Molecular & Cellular Proteomics Jan. 3, 2002. 1:157-168. Canada.

Pegah N. Abadian et al. Accepted Manuscript. Book: Analytical Methods. 22pgs. Boston, MA.

Kling A. et. al. Electrochemical microfluidic platform for simultaneous multianalyte detection. Article, 2015, 916-919, Europe.

Andre Kling et al. Multianalyte Antibiotic Detection on an Electrochemical Microfluidic Platform. Article. Jul. 19, 2016, 10036-10043, Germany.

Mercier Marco. Microfluidic Continuous Flow Cell Counting and Concentration. Article. 10pgs.

Meichei Wang Kadlec et. al. A Cell Phone-Based Microphotometric System for Rapid Antimicrobial Susceptibility Testing. Journal. 2014, vol. 19 (3) 258-266. Tucson, AZ.

Hongying Zhu et. al. Cost-effective and compact wide-field fluorescent imaging on a cell-phone. Article. Jan. 21, 2011. 315-322, 11(2). California.

Moffitt Jeffrey R. et. al. The single-cell chemostat: an agarose-based, microfluidic device for high-throughput, single-cell studies of bacteria and bacterial communities. Article. Oct. 24, 2017. 21pgs. 12(8).

Temiz Yuksel et al. Microelectronic Engineering. Article. 2015. 156-175. Published by Elsevier B.V. Switzerland.

Vasdekis Andreas et al. Review of methods to probe single cell metabolism and bioenergetics, Journal, Jan. 20151. 115-135. Published by Elsevier.

Wang Shuqi et al. Portable microfluidic chip for detection of *Escherichia coli* produce and blood. International Journal of Nanomedicine. May 27, 2012. 2012:7 2591-2600. MA.

Hoylandm James Donaldson. Microfluidic chip and connector. Nov. 11, 2012, 16pgs. Europe.

Baltekin Ozden et al. Antibiotic susceptibility testing in less than 30 min using direct single-cell imaging. Aug. 22, 2017. 9170-9175 vol. 114-34.

Ashraf Muhammad Waseem. Micro Electromechanical Systems (MEMS) Based Microfluidic Devices for Biomedical Applications. Journal : Molecular Sciences. Jun. 7, 2011. 3648-3704.

Radenovic Aleksandra. Advanced Bioengineering Methods Laboratory Microfluidics Lab on Chip. 27pgs.

U. Hassan et al, A microfluidic biochip for complete blood cell counts at the point-of-care, Dec. 2015, 201-213, 3(4).

Kling Andre et al, Multianalyte Antibiotic Detection on an Electrochemical Microfluidic Platform, 1-3 pgs. Germany.

Au K. Anthony et al, Microvalves and Micropumps for BioMEMS, May 24, 2011, 179-220.

Sticker Drago et al, Multi-layered, membrane-integrated microfluidics based on replica molding of a thiol-ene apoxy thermoset for . . . . Article, Nov. 2015, 4542-4554.

Shaegh et al, Plug-and-play microvalve and micropump for rapid integration with microfluidic chips, Article, Apr. 22, 2015, 557-564, Massachusetts, Springer Berlin Heidelberg.

Schafer Dawn et al, Microfluidic cell counter with embedded optical fibers fabricated by femtosecond laser ablation and anodic bonding, Article, Apr. 13, 2009, 17(8), 6068-6073, Colorado.

Hassan U. et al, A microfluidic biochip for complete blood cell counts at the point-of-care, Dec. 2015, 201-213. 3(4).

Brown, M. C. et al. (2009). Lateral Flow Immunoassay. Tse, H. Y., Wong, R. C. (Eds.). New York, NY: Humana Press.

Baltekin, O., et al. (Aug. 22, 2017). Antibiotic susceptibility testing in less than 30 min using direct single-cell imaging. Proceedings of the National Academy of Sciences. 114(34).

Mudanyali, O. et al. Integrated Rapid-Diagnostic-Test Reader Platform on a Cellphone. Lab on a Chip, vol. 12, No. 15. Aug. 7, 2012; pp. 7, 12.

FisherSCI. Anti-Zika virus ELISA (IgM) test instruction. Sep. 2, 2016.

Acharya, D. et al. An ultrasensitive electrogenerated chemiluminescence-based immunoassay for specific detection of Zika virus. Scientific Reports 6, Article No. 32227. Aug. 2016.

International Search Report and Written Opinion of the International Searching Authority from PCT/US17/57037, dated Dec. 28, 2017.

International Search Report and Written Opinion of the International Searching Authority from PCT/US17/57039, dated Dec. 26, 2017.

(56) References Cited

OTHER PUBLICATIONS

International Search Report and Written Opinion of the International Searching Authority from PCT/US17/57041, dated Dec. 14, 2017.
International Search Report and Written Opinion of the International Searching Authority from PCT/US17/60252, dated Jan. 12, 2018.
International Search Report and Written Opinion of the International Searching Authority from PCT/US17/66528, dated Mar. 7, 2018.

* cited by examiner

DEMOGRAPHIC I.D.

PERSONAL EMAIL

DTS (DATE/TIMESTAMP

EVRK

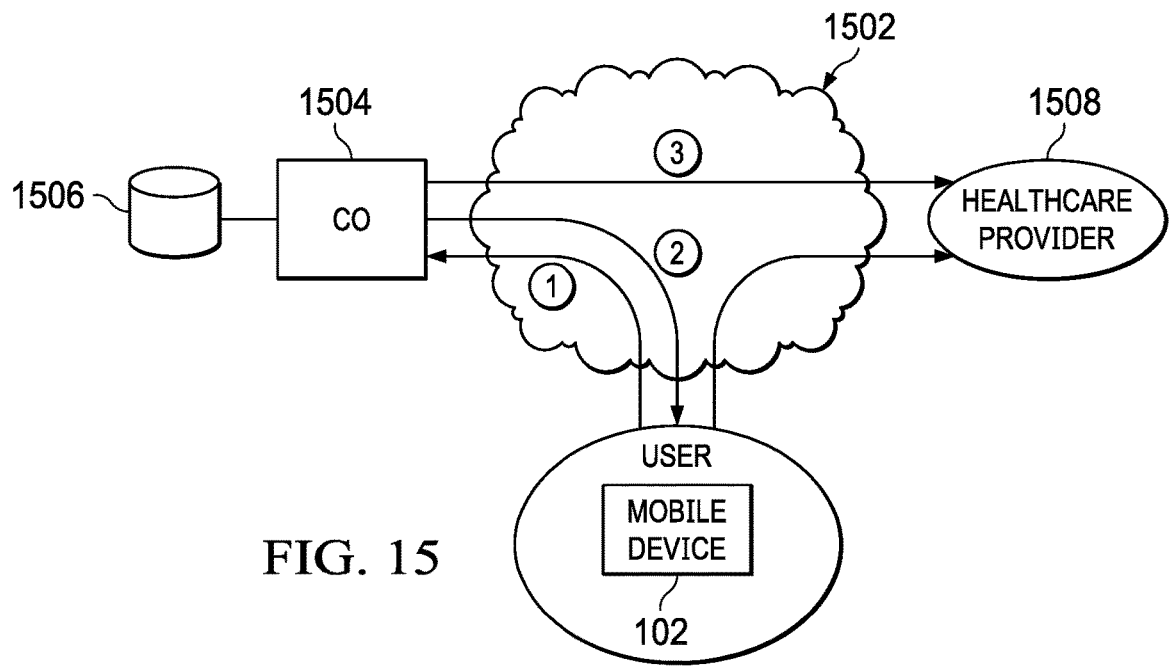
FIG. 15
| | 1604 | 1606 | 1608 |
|---|---|---|---|
| 1602 | TEST RATING | HEALTH RISK | MEDICAL INTERVENTION TYPE |
| | 76+ | DEADLY | EMERGENCY |
| | 51-75 | DANGEROUS | URGENT |
| | 26-50 | ELEVATED | NONE |
| | 0-25 | NORMAL | NONE |
FIG. 16
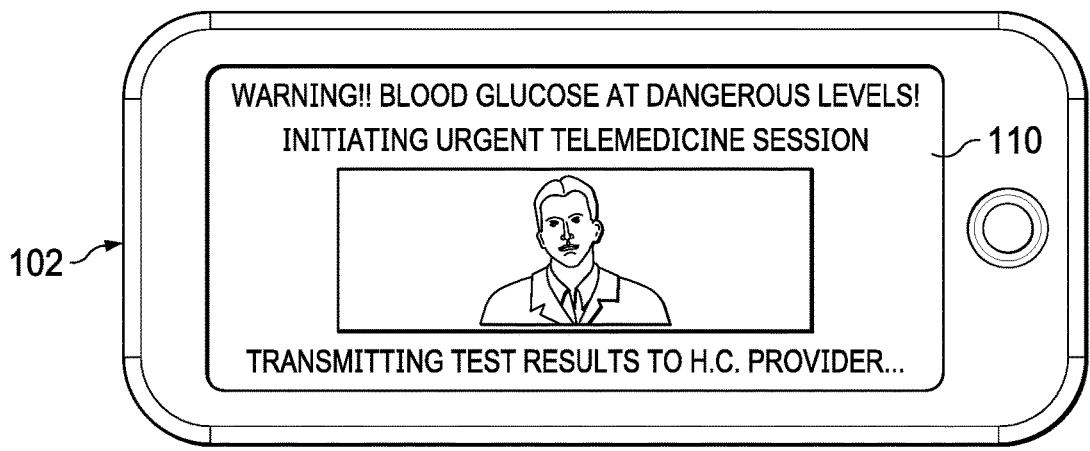
FIG. 17

| UNIQUE I.D. # XXXXX | | ← 1902 |
|---|---|---|
| NAME | JOHN DOE | ← 1904 |
| BIOLOGIC | 2402 | ← 1910 |
| BIOLOGIC | 6743 | ← 1910 |
| DOCTOR | M. FRANKLIN | ← 1906 |
| PHARMACY | MEDCO | ← 1908 |

2404

| TEST I.D. #10 | |
|---|---|
| TEST DATE | 11/5/2015 |
| BIOLOGIC TYPE | SALIVA |
| TEST TYPE | STREPTOCOCCAL |
| INFECTION STATUS | Y |
| EFFECTIVE TREATMENT | DOSE OF AMOXICILLIN |
| EFFECTIVE TREATMENT DOSAGE | 250 mg |
| TREATMENT PLAN | ADMINISTER TREATMENT AT EFFECTIVE DOSE EVERY 12 HOURS FOR 2 WEEKS |

2402

| PATIENT ID #1002 | |
|---|---|
| TEST I.D. | 10 |
| TEST I.D. | 11 |
| TEST I.D. | 12 |
| PRIMARY CARE PHYSICIAN | M. FRANKLIN |
| . | |
| . | |
| . | |
| INSURANCE INFORMATION | MEDCO |

FIG. 24

| HAPLOGROUP C | 2804 |
|---|---|
| TEST I.D. # 10 | 10720 |
| TEST I.D. # 11 | 2 |
| TEST I.D. #12 | 450 |
| . | |
| . | |
| . | |

| PATIENT ID #1002 | 2802 |
|---|---|
| TEST I.D. | 10 |
| TEST I.D. | 11 |
| TEST I.D. | 12 |
| PRIMARY CARE PHYSICIAN | M. FRANKLIN |
| HAPLOGROUP | C |
| TRENDING SUSCEPTABILITY | PROSTATE CANCER |
| . | |
| . | |

FIG. 28

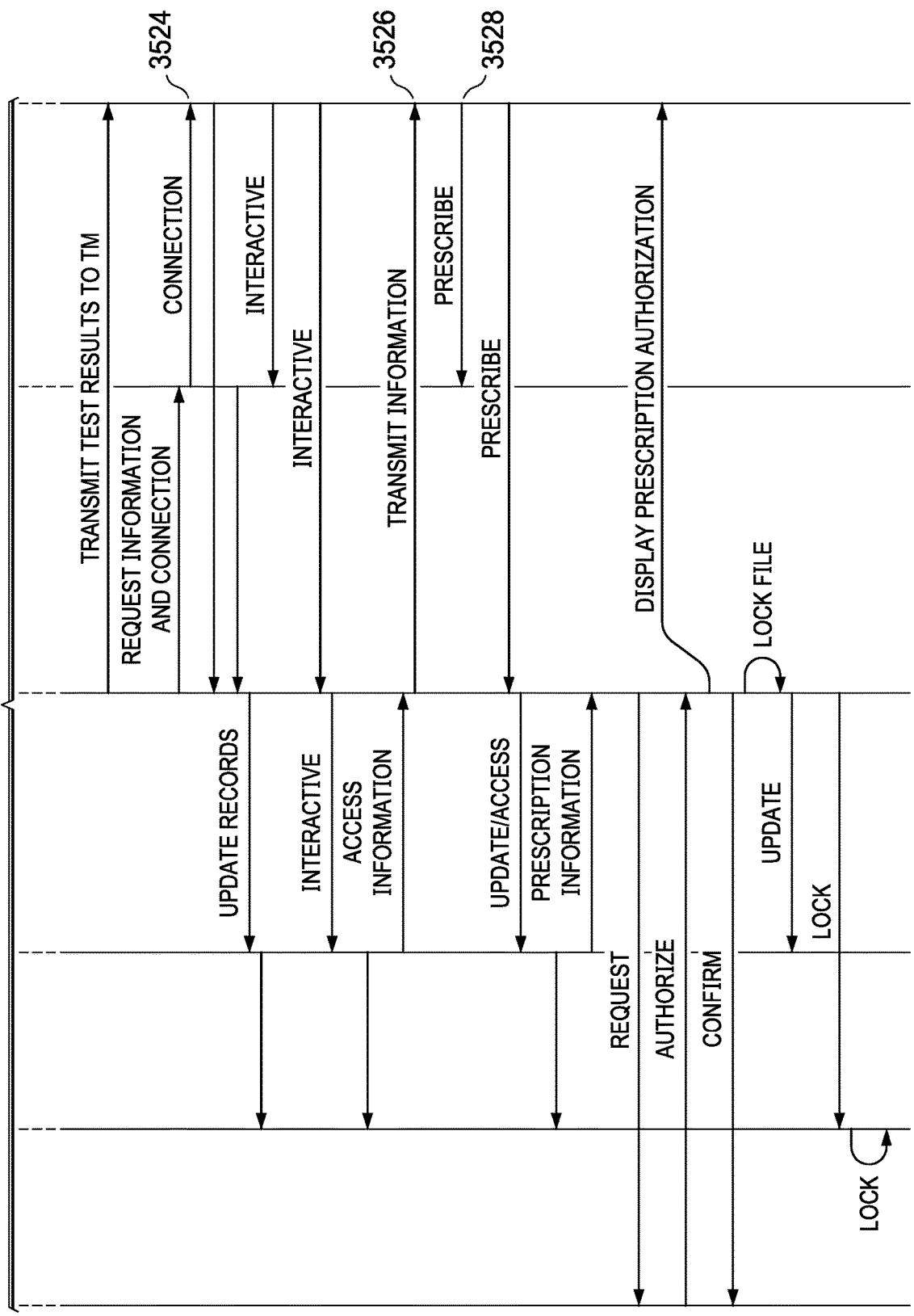

SYSTEM AND METHOD FOR QUANTIFYING, ENSURING, AND TRIGGERING THE PRESCRIPTIVE AUTHORITY FOR A TELEMEDICINE SESSION

CROSS-REFERENCE TO RELATED APPLICATIONS

This application claims the benefit of U.S. Provisional Application No. 62/681,602, filed Jun. 6, 2018, and entitled SYSTEM AND METHOD FOR QUANTIFYING, ENSURING, AND TRIGGERING THE PRESCRIPTIVE AUTHORITY FOR A TELEMEDICINE SESSION, the specification of which is incorporated herein in its entirety.

TECHNICAL FIELD

The following disclosure relates to a system for quantifying, ensuring, and triggering prescriptive authority for a telemedicine session.

BACKGROUND

A current issue with telemedicine procedures is that telemedicine healthcare professionals, that is, doctors and other personnel that participate in and provide telemedicine services to patients may be reluctant to write a prescription for a medication for a patient. This is because confirmation of patient identity and confirmation of actual patient symptoms and diagnosis is limited when the telemedicine healthcare professionals typically only have a brief communication, such as a video conference, with the patient. The telemedicine healthcare professional may be concerned that the patient is faking symptoms to get medications, may be concerned that the telemedicine healthcare professional may improperly diagnose the patient and provide medication that could harm the patient, or may fear liability due to an improper medication being prescribed.

SUMMARY

In one aspect thereof, a method for creating a unique transaction ID (UTID) securely representing a medical diagnostic transaction between a user/patient and a telemedicine professional is provided. The method includes receiving at a central office from a user/patient's mobile unit (MU) test information generated by a test platform proximate the user/patient's MU of a biologic received from the user/patient that tests for a specific medical condition to initiate a new diagnostic transaction, the central office having a first central office database for storing medical information and profile information for a plurality of users/patients, the central office having a second central office database for storing UTIDs, initiating generation of a UTID for the new diagnostic transaction initiated by the receive operation for storage of any transaction information associated therewith after creation thereof in the second central office database, and wherein all subsequent transactions associated with the UTID will be stored in the second central office database in association with and as part of the UTID, analyzing the received test information to determine if the test information indicates a positive or a negative result for the testing of the specific medical condition, transferring the analysis results back to the user/patient's MU for display to the user/patient, and receiving from the MU a request for a telemedicine professional session and in response thereto executing the following steps at the central office representing a diagnostic procedure for the specific medical condition following predetermined industry standard diagnostic procedures for such diagnosis for the specific medical condition, including analyzing the test results with an expert system in view of user/patient stored information in the first central office database to determine at least one treatment regimen, the expert system being trained on the predetermined industry standard diagnostic seizures associated with the diagnostic procedures for the specific medical condition and for generating a result of a suggested an industry recommended treatment regimen, contacting a telemedicine professional and transmitting predetermined information from the first central office database including at least the test results and determined treatment regimens determined by the expert system, receiving interactions between the telemedicine professional and the user MU, receiving approval from the telemedicine professional of a selection of the determined treatment regimen determined from at least responses from the user/patient by the telemedicine professional through the user/patient's MU in addition to the determined treatment regimens provided by the expert system or from stored preferences of the user/patient stored in the first central office database that define the appropriate action to be taken to complete an approved treatment regimen approved by the telemedicine professional, and locking the UTID to prevent additional transaction information from being appended thereto.

BRIEF DESCRIPTION OF THE DRAWINGS

For a more complete understanding, reference is now made to the following description taken in conjunction with the accompanying Drawings in which:

FIG. 4D illustrates an embodiment which includes a data stream which contains demographic information;

FIG. 4E illustrates an embodiment in which the unique identifier contains a data stream which indicates whether or not the user has supplied their personal email address;

FIG. 4F illustrates an embodiment of a data stream for a unique identifier which contains a timestamp of when a completed medical test is scanned or photographed by the mobile application;

FIG. 4G illustrates a data stream for an embodiment in which a unique identifier contains information related to the results of a medical test;

FIG. 15 illustrates an embodiment of a system which utilizes a remote diagnostic test to initiate a medical escalation and intervention;

FIG. 16 illustrates an example of a table which would be found in the database of a central office and which contains criteria for when to initiate a medical intervention based on the results of a remote diagnostic test;

FIG. 17 illustrates a mobile device from an embodiment in which a medical intervention in the form of a telemedicine session is initiated on a mobile device in response to a diagnostic test;

FIG. 24 illustrates information that may be recorded in a patient record in accordance with various embodiments of the present disclosure;

FIG. 28 illustrates one embodiment of database tables showing a particular trend in accordance with various embodiments of the present disclosure;

FIGS. 35A and 35B illustrate a sequence diagram depicting one specific example of a telemedicine transaction;

DETAILED DESCRIPTION

Figure 1:
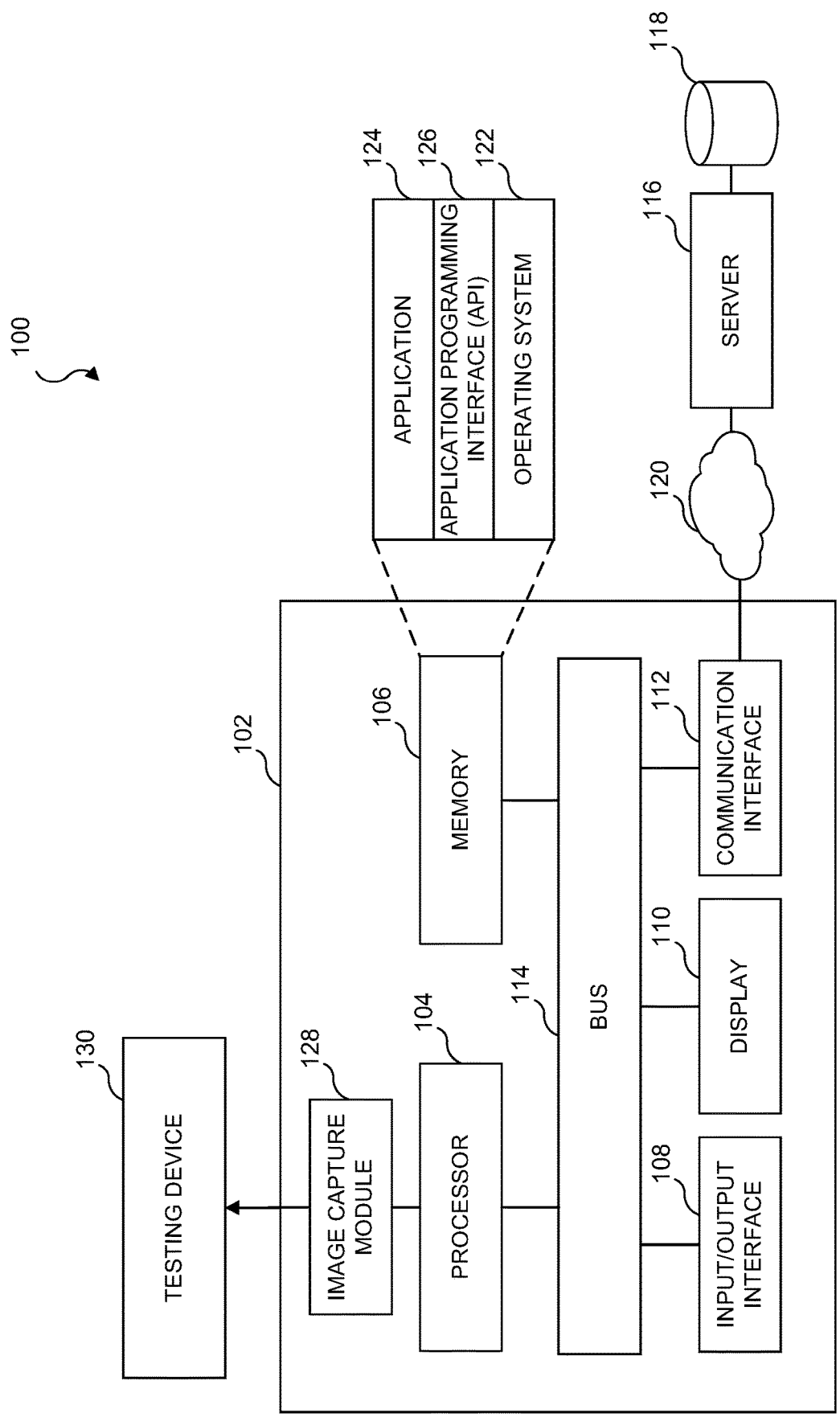
FIG. 1 illustrates a diagrammatic view of a biofluidic triggering system in accordance with various embodiments of the present disclosure.

Referring now to the drawings, wherein like reference numbers are used herein to designate like elements throughout, the various views and embodiments of a system and method for quantifying, ensuring, and triggering the prescriptive authority for a telemedicine session is illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

In some embodiments, a biological specimen (i.e. saliva, blood, urine, semen, feces) may be provided by a user onto an analog testing device. The analog testing device may be used for testing strep (i.e. strep A, strep B, rapid strep), TP/INR, chronic conditions, MERS (Middle Eastern Respiratory Syndrome), diabetes, urinary tract infection and analysis, influenza, pregnancy, HIV, malaria, immunology, blood glucose, hemoglobin, blood electrolytes, cholesterol, fertility, troponin, cardiac markers, fecal analysis, sperm viability, food pathogens, HemoCues, CRP (put them in), dengue fever, HBA1C (put them in), Homocystein, salivary assay, drugs of abuse, drug interaction, infectious diseases, viral loads, tuberculosis, allergies (i.e. food and environment), Lyme disease, Methacillian-resistent MRSA, *Staphylococcus* areas, sexually transmitted diseases, thyroid stimulating hormone (TSH), lipid profile, INR (put them in), TEG, magnesium, lactate, transcutaneous bilirubin, *Helicobacter pylori*, bacteria, cell count, cancer markers, tumor markers, resistant *Staph aureus*, antibiotic resistance, stroke markers, sepias markers, DNA markers, parathyroid, renal, or any other type of analog testing device that utilizes a biological specimen to determine a user's disease, disability, discomfort or dissatisfaction state of health. In some embodiments, the analog testing device may be compact and hand-held. In some embodiments, the analog testing device may be a standard stand-alone device.

In some embodiments, the user may take a sample of the biological specimen and transfer the biological specimen to an input of the testing device. The input of the testing device may include an input window that guides and holds the biological specimen securely within the analog testing device. In some embodiments, more than one window may be provided on the analog testing device to accommodate more than one biological specimen. For instance, the analog testing device may include two windows for a pregnancy test, in which one window may be provided to receive urine to test for the presence of HCG and a second window may be provided to receive urine to test for urinary tract infection bacteria. In some embodiments, multiple analog testing devices with one or more input windows may be used to detect the biological specimen. In some embodiments, the analog testing device may include a results display window indicating a positive or negative sign, a color spectrum, a line, a circle, a curve, a balloon, a signature marker, or variance of the like. The results may be mathematical, geometrical, color spectral, light spectrum, cell multiplication, or the like. The display window may indicate the completion of the test, an error, the test results or a combination thereof.

In some embodiments, the user may capture the results on the results display window via a mobile computing device, for instance in the form of audio, video, photo, scan, or a combination thereof. The mobile computing device may include one or more peripheral devices, for instance, an image scanner, microphone, video recorder, digital camera, speakers, and the like, to capture the results from the analog testing device and convert the results into a digital data package.

FIG. 1 illustrates a diagrammatic view of a biofluidic triggering system 100 in accordance with various embodiments of the present disclosure. The system 100 may include a mobile device 102. The mobile device 102 may be a mobile handheld user device, such as a smart phone, tablet, or the like. The mobile device 102 may include a processor 104, a memory 106, an input/output (I/O) interface 108, a display 110, and a communication interface 112 all connected via a bus 114. The communication interface may connect the mobile device 102 to outside sources, such as a server 116 having a database 118 associated therewith, over a network 120, i.e. a cellular network or Internet network. The memory 106 may store an operating system 122 and various special-purpose applications, such as a browser by which webpages and advertisements are presented, or special-purpose native applications, such as weather applications, games, social-networking applications, shopping applications, and the like. The digital data package may provide data to a special purpose native application 124 stored in the memory 106, the application 124 having associated therewith an application programming interface (API) 126. The digital data package may be obtained by the mobile device 102 by an image capture module 128 connected to the processor 104. The image capture module 128 may capture an image, scan, video, or other digital media of a testing device 130, converting the analog biologic sample testing device and the results presented on the device to a digital format and to create a unique identifier for providing a unique record of each transaction and that can be used to trigger a plurality of events.

The unique identifier comprising the digital data package may be analyzed by the application 124 to determine the results from the analog testing device. In some embodiments, the determination of the test results, due to the type of analog testing device, is not determined locally by the application 124. In some embodiments, the unique identifier may be transmitted to the server 116, via the network 120, for remote analysis of the data contained in or associated with the unique identifier. In some cases, results from the analog testing device may be determined locally and remotely. In some instances, the user of the mobile device 102 may not have cellular network or Internet connection, for instance, the settings for connectivity on the mobile device 102 is disabled, turned off or a combination thereof. In this case, the transmission of the unique identifier to the server 116 may be postponed until a connection is available. As will be described in more detail hereinbelow, this unique identifier is created at the initiation of a particular test transaction and will contain all of the information associated with the transaction from start to finish. At any point in the process, the unique identifier can be analyzed to determine the next step and the result of that analysis will be used to trigger the next step.

In some embodiments, the mobile device 102 may include a location sensor, such as a global positioning system (GPS) sensor or other components by which geographic location is obtained, for instance, based on the current wireless environment of the mobile device 102, like SSIDs of nearby wireless base stations, or identifiers of cellular towers in range. In some cases, geographic locations are inferred by, for instance, an IP address through which a given mobile device 102 communicates via the Internet, which may be a less accurate measure than GPS-determined locations. In other cases, geographic location is determined based on a cell tower to which a mobile device 102 is wirelessly connected. Depending on how the geographic data is acquired and subsequently processed, that data may have better or less reliable quality and accuracy.

Figure 2:
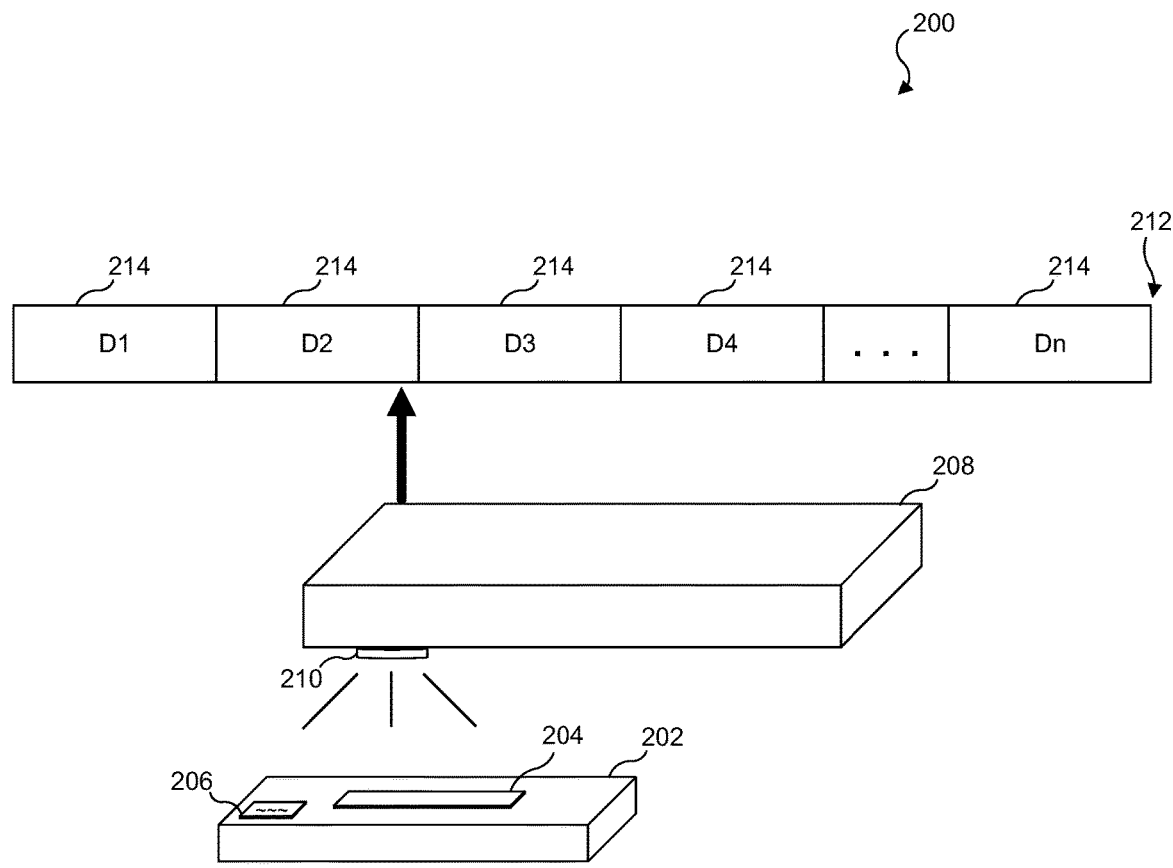
FIG. 2 illustrates a diagrammatic view of an analog testing device to a digital format and unique identifier conversion process.

FIG. 2 illustrates a diagrammatic view of an analog testing device to a digital format and unique identifier conversion process 200 in accordance with various embodiments of the present disclosure. A testing device 202 may provide medical test results in an analog format, such as in a results display window 204 indicating a positive or negative sign, a color spectrum, a line, a circle, a curve, a balloon, a signature marker, or variance of the like. A biologic specimen may be deposited into the testing device 202 where the biologic may bind or react with particular reagents specific to the type of test to which the testing device 202 pertains. The testing device 202 may also include a test type identifier 206, such as a code, graphic, symbol, or other indicator on a surface of the testing device 202.

A mobile device 208, which may be the mobile device 102 described herein, may include a capture device 210. The mobile device 208 may convert use the capture device 210, in addition to other data known or otherwise obtained by the mobile device 208, to convert the analog data and biologic presented by the testing device 202 to a digital unique identifier 212. When digital media such as an image, video, or other digital format of the testing device 202 is captured by the capture device 210, certain properties may be analyzed, processed, and stored as a digital data package. For instance, the test type associated with the testing device 202 may be determined by the mobile device 208 by identifying the particular test associated with the test type identifier 206 captured within the digital media and disposed on the surface thereof so as to be able to be captured with the mobile device and possibly analyzed at the mobile device.

Test results provided in the results display window 204 or elsewhere on the testing device 202 may also be captured within the digital media and analyzed. For example, in the case of a color indicator as the result of the test, the RGB values of the pixels contained in the digital media of the test results may be analyzed in order to provide a digital value for the test results. The test result may be stored in the digital data package in a particular digital format, for instance, a positive or negative test result value. The value may be a binary value, a rating, a probability, or other type of result indicator. The biologic specimen used to conduct the test may also be included in the digital data package. The biologic specimen introduced to the testing device 202 may be determined from the test type identifier 206, since in many cases the specific test will dictate the biologic to be used.

The data provided by the digital data package may also include the type, manufacture and serial number of the testing device 202, and a timestamp for when the capture device 210 captured the digital media. The manufacture, serial number and cellular provider of the mobile device 208 may also be included in the digital data package. The application 124 may then generate the unique identifier 212 from the data of the testing device 202 and mobile device 208, in combination with data of the user of the mobile device 208. Data of the user may be the user's name, birthday, age, gender, social security number, height, weight, race, diagnosis status, insurance information, medical codes, drug codes, and the like, and a combination thereof.

In some embodiments, the unique identifier may be verified by a verification server, such as the server 116, to determine the authentication of the biological specimen. In some cases, the user may provide the analog testing device 202 with a substance not classified as a biological specimen. In this instance, an application on the server 116 will provide the application program interface 110 with a message indicating an error, in which the user may be required to provide a biological specimen to a different analog testing device. In some embodiments, after verification of a biological specimen, the local application program 124 or the server 116 via the user's application program 124 will provide the user with a positive or negative outcome of the analog testing device 202. In some cases, the user is displayed a negative test result and the application program 124 of the mobile device 208 indicates that testing is completed. In other cases, the user is displayed a positive test result by the application program 124 on the display 110 of the mobile device 208.

The unique identifier 212 may include of a plurality of digital data streams 214 used during creation of the unique identifier 212, such as information included within the digital data package, or otherwise known or obtained by the mobile device 208 or the server 116. The plurality of digital data streams 214 (D1, D2, D3, D4 . . . Dn) may be assembled together to create the unique identifier 212, and the mobile device 208, the server 116, or the authorized system components may parse or deconstruct the unique identifier 212 to analyze specific user properties or test properties, and to trigger events based on the properties.

Creating a single unique identifier 212 which contains many different items of information is an efficient way of associating many different types of information with a single biologic, user, test, etc. Every time a test is conducted, a new unique identifier 212 may be created. Each unique identifier created may include the plurality of data streams 214. Each one of the plurality of data streams 214 in the unique identifier 212 stores a different type of information. In some embodiments, the information stored in data streams 214 includes the test type, the test results, demographics of the user, or an identification number, such as an IMSI number, for the mobile device 208. Different embodiments may include different data streams 214, as is described hereinbelow with respect to FIGS. 4A-4K. In some embodiments, the unique identifier 212 is set up in a structural format, such that each data stream 214 is a subcomponent of the unique identifier 212. In some embodiments, unique identifier 212 is a string of alphanumeric characters, and the data streams 214 which make up the unique identifier 212 are simply different portions of the character string. In these embodiments, the format of the unique identifier 212 is known to a database or server which can correctly parse the unique identifier 212 into the separate data streams 214 for analysis.

Figure 3:
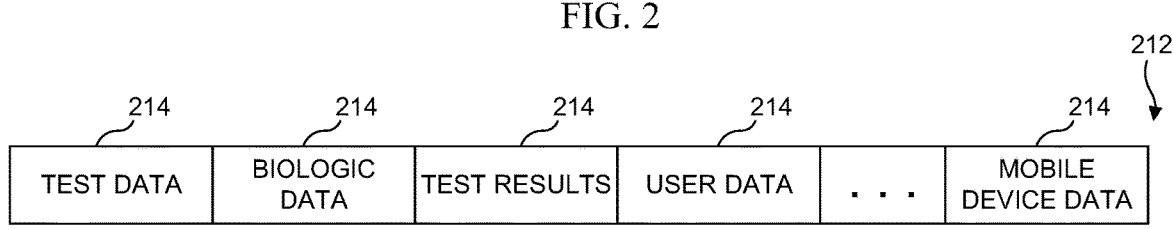
FIG. 3 illustrates one example of a unique identifier in accordance with various embodiments of the present disclosure.

FIG. 3 illustrates one example of a unique identifier 302 in accordance with various embodiments of the present disclosure. In this example, the plurality of data streams 212 includes, but is not limited to, test data, such as test type, biologic data, such as biologic type or types used by the test, test results obtained upon completion of the test, user data such as demographics, and mobile device data, such as an IMSI number.

Figure 4A:
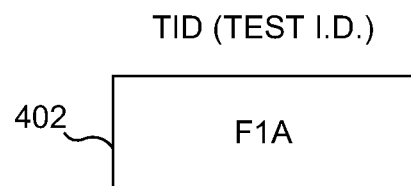
FIG. 4A illustrates an embodiment in which one of the data streams of the unique identifier is a test identification, TID field.

Referring now to FIG. 4A, there is illustrated an embodiment in which one of the data streams 214 of the unique identifier 212 is a test identification, TID data stream 402. The TID data stream 402 identifies the type of test which the user is conducting (pregnancy, HIV, peanut allergy, etc.). In the example depicted in FIG. 4A, the TID data stream 402 is a character string of "F1A," which indicates that the test is for the flu, is test version "1," and is a test of an example "A" type of flu substrain. Different embodiments of TID data stream 402 will have different sizes of character strings, or will not be character strings at all. In some embodiments, this information is obtained when a user uses the mobile application to scans a barcode or image from the test product, or when the user inputs an identification code into the mobile application. In some embodiments, the data in the TID data stream 402 is used by the mobile application to determine which database to access when processing the results of the medical test.

Figure 4B:
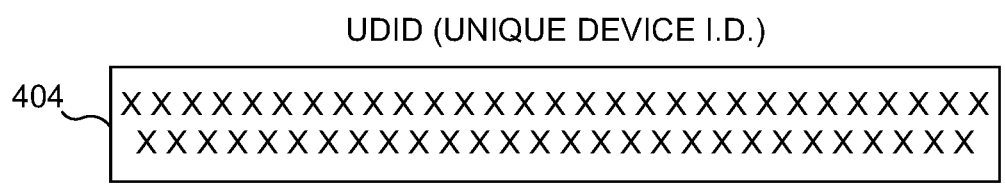
FIG. 4B illustrates an embodiment in which one of the data streams of the unique identifier is a unique device identification, or UDID field.

Referring now to FIG. 4B, there is illustrated an embodiment in which one of the data streams 214 of the unique identifier 212 is a unique device identification, or UDID data stream 404. The UDID data stream 404 contains information which uniquely identifies the mobile device on which the application is running. Many devices, such as mobile phones, have unique physical device identifiers built-in by the manufacturer, often in the form of long character strings, such as an IMSI number. In some embodiments, the UDID data stream 404 is a character string which includes such an identifier. In other embodiments, the UDID 404 is generated by the mobile application or the mobile application user.

Figure 4C:
FIG. 4C illustrates an embodiment which includes a SOD (self/other identification) field.

Referring now to FIG. 4C, there is illustrated an embodiment which includes a SOID (self/other identification) data stream 406. The SOID data stream 406 is a data stream 214 which designates whether the medical test is being performed on the mobile application user, or whether the test is being performed on an individual other than the user. The SOID data stream 406 also identifies the relationship between the person being tested and the mobile application user. Some embodiments also include basic demographic data, such as gender or age range, in the SOID data stream 406. For example, if the person being tested is a small child, then the actual user of the mobile application may be the child's mother or father. In the example depicted in FIG. 4C, the SOID data stream 406 is a character string which reads "CF3," which indicates that the person being tested is a child of the mobile application user, is female, and is three-years-old. Naturally, other embodiments will have different formats for the SOID data stream 406, and may not be character strings.

Referring now to FIG. 4D, there is illustrated an embodiment which includes a data stream 2302 which contains demographic information. A DEMZIP data stream 408 (demographic/ZIP code) contains information about the person being tested with the medical test. In the example illustrated in FIG. 4D, the DEMZIP data stream 408 includes a character string which represents the gender, age range, and geographic location (in the form of a ZIP code) of the person being tested. For example, in FIG. 4D, the DEMZIP data stream 408 indicates that the test subject is a male, in age range 4, who is located in the ZIP code 78237. In other embodiments, the DEMZIP data stream 408 will have additional demographic traits included, such as height or weight. Some embodiments will contain geographic location information in a format other than ZIP code, such as city, state, or country names. In some embodiments, such as is illustrated in FIG. 4D, the DEMZIP data stream 408 will be a character string, while in other embodiments, it will take other forms.

Referring now to FIG. 4E, there is illustrated an embodiment in which the unique identifier 212 contains a data stream 214 which indicates whether or not the user has supplied their personal email address. A personal email data stream 410 does not actually contain the email address of the user, but it does indicate whether or not the user has supplied an email address to the mobile application. In some embodiments, if personal email data stream 410 indicates that the user has supplied an email address, then when the unique identifier 212 is passed to a remote server, the remote server will link the unique identifier 212 with the email address of the user which has been stored in a separate database. In some embodiments, such as illustrated in FIG. 4E, the personal email data stream 410 is a simple character string of "Y" or "N" to indicate "yes" or "no" with regard to whether an email has been supplied. Other embodiments will have a "1" or a "0" for "yes" or "no" or may have other character strings or data formats.

Referring now to FIG. 4F, there is illustrated an embodiment of a data stream 214 for a unique identifier 212 which contains a timestamp of when a completed medical test is scanned or photographed by the mobile application. Knowing exactly when a medical test was scanned by a mobile application can be very important in different types of analysis. In this embodiment, the DTS data stream (date/time stamp) 412 indicates the time in a YYMMDDH-HMMSS format, that is, the first two characters indicate the year, the next two indicate the month, the next two indicate the day, the next two indicate the hour (in a 24-hour day format), the next two indicate the minute, and the last two indicate the second. Naturally, some embodiments will have other formats for the DTS data stream other than a 12-character string, and will have different levels of specificity with regard to the time.

Referring now to FIG. 4G, there is illustrated a data stream 214 for an embodiment in which a unique identifier 212 contains information related to the results of a medical test. These embodiments will have test results, or information related to test results as part of the overall unique identifier 212 as an EVRK (Evaluation of Results and Ranking of the Diagnosis) data stream 414, as opposed to, or in addition to, the results being in a totally separate file. In embodiments of the system which use numerical values for test results, these values will be incorporated into the EVRK data stream 414. Some embodiments will also include an escalation scale, which is a numerical indication, as a number on a predetermined scale, of how urgent or serious a potential medical problem might be. In the example illustrated in FIG. 4G, the EVRK data stream 414 is a character string and has a value of "0982," with the first three digits representing the results of the test and the last digit representing the escalation scale value. Other embodiments will have other formats for the EVRK data stream 414 and will have the results indicated in other ways, such as alphanumerically, rather than just numerically.

Figure 4H:
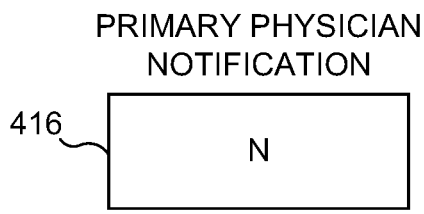
FIG. 4H illustrates a data stream for an embodiment in which a unique identifier includes an indication of whether or not the user wishes to have the test results sent to a healthcare provider.

Referring now to FIG. 4H, there is illustrated a data stream 214 for an embodiment in which a unique identifier 212 includes an indication of whether or not the user wishes to have the test results sent to a healthcare provider. In these embodiments, the unique identifier 212 includes a PDr (personal doctor) data stream 416. The PDr data stream 416 is simply an indication of whether or not the user wishes to have the test results transmitted to the user's healthcare provider. In some embodiments, a user inputs this preference into the mobile application after completing the medical test, while, in other embodiments, this preference is input into the mobile application separately from any particular test. In some embodiments, an indication of wanting the results sent to the healthcare provider will initiate a telemedicine session with the healthcare provider. In some embodiments, such as that which is illustrated in FIG. 4H, the PDr data stream 416 is a short, simple character string, such as "Y," "N," "1," or "0." Other embodiments will have different formats.

Figure 4I:
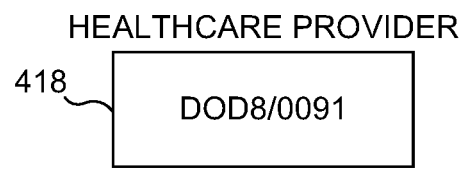
FIG. 4I illustrates a data stream for an embodiment in which a unique identifier includes information identifying the user's healthcare provider.

Referring now to FIG. 4I, there is illustrated a data stream 214 for an embodiment in which a unique identifier 212 includes information identifying the user's healthcare provider. In these embodiments, the unique identifier 212 includes a Healthcare Provider data stream 418. The Healthcare Provider data stream 418 includes information which can be used in a storage database to look up the healthcare provider's identification and contact information. This information would be used in situations where the mobile application user indicates that they wish to have the medical test results sent to the healthcare provider. In some embodiments, the Healthcare Provider data stream 418 contains a code which is used to look up more detailed information from another storage database, while in other embodiments, the identification information and the contact email address or phone number is stored in the data stream itself.

Figure 4J:
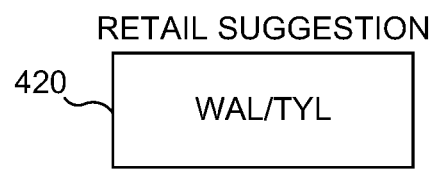
FIG. 4J illustrates a data stream for an embodiment in which a unique identifier includes information relating to a retail suggestion.

Referring now to FIG. 4J, there is illustrated a data stream 214 for an embodiment in which a unique identifier 212 includes information relating to a retail suggestion. For these embodiments, a Retail Suggestion data stream 420 is included in the unique identifier 212. The Retail Suggestion data stream 420 includes data which identifies a retailer or a product or service which can be suggested (for example, through the mobile application) to a user. In some embodiments, these suggestions are based on the type of medical test performed. In other embodiments, the suggestions are based on the results of the medical test. For example, if the medical test is a pregnancy test which returns a positive result, then the suggestion might be for a brand of baby diapers. In the example illustrated in FIG. 4J, the Retail Suggestion data stream 420 provides a suggestion of Tylenol ("TYL") which can be purchased at Walgreens ("WAL"). In the example illustrated in FIG. 4J, the Retail Suggestion data stream 420 is a character string. In other embodiments, the format of the Retail Suggestion data stream 420 will be different. In some embodiments, the Retail Suggestion data stream is utilized in situations where the PDr data stream 416 indicates that the user does not wish to have the test results communicated to a healthcare provider.

Figure 4K:
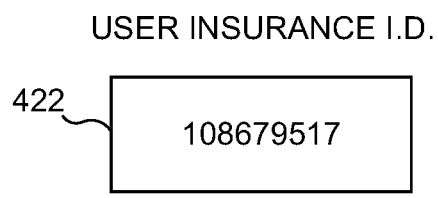
FIG. 4K illustrates a data stream for an embodiment in which a unique identifier includes information identifying the user's insurance I.D.
Figure 5A:
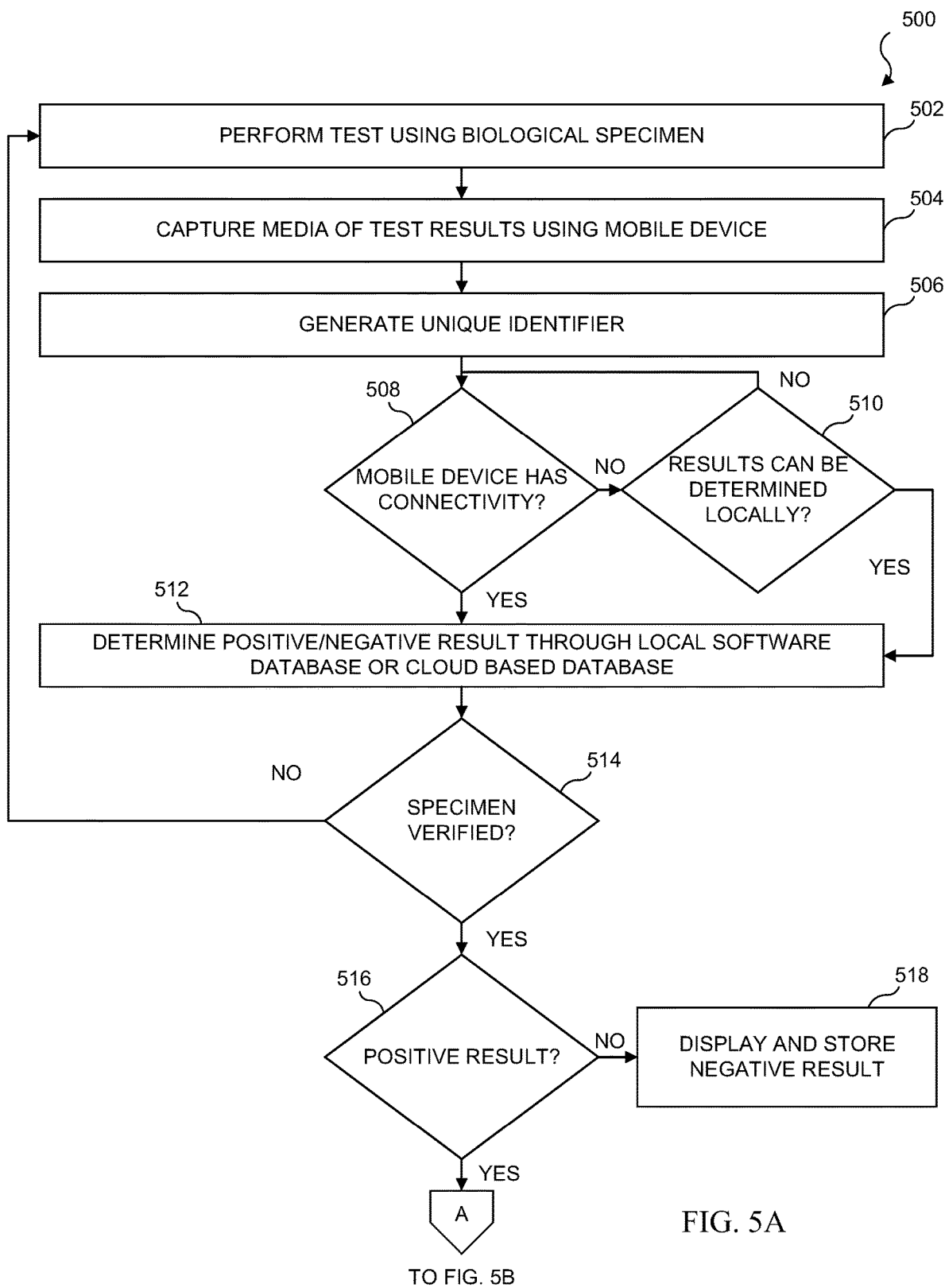
FIGS. 5A-5D illustrate a biofluidic triggers process.
Figure 5B:
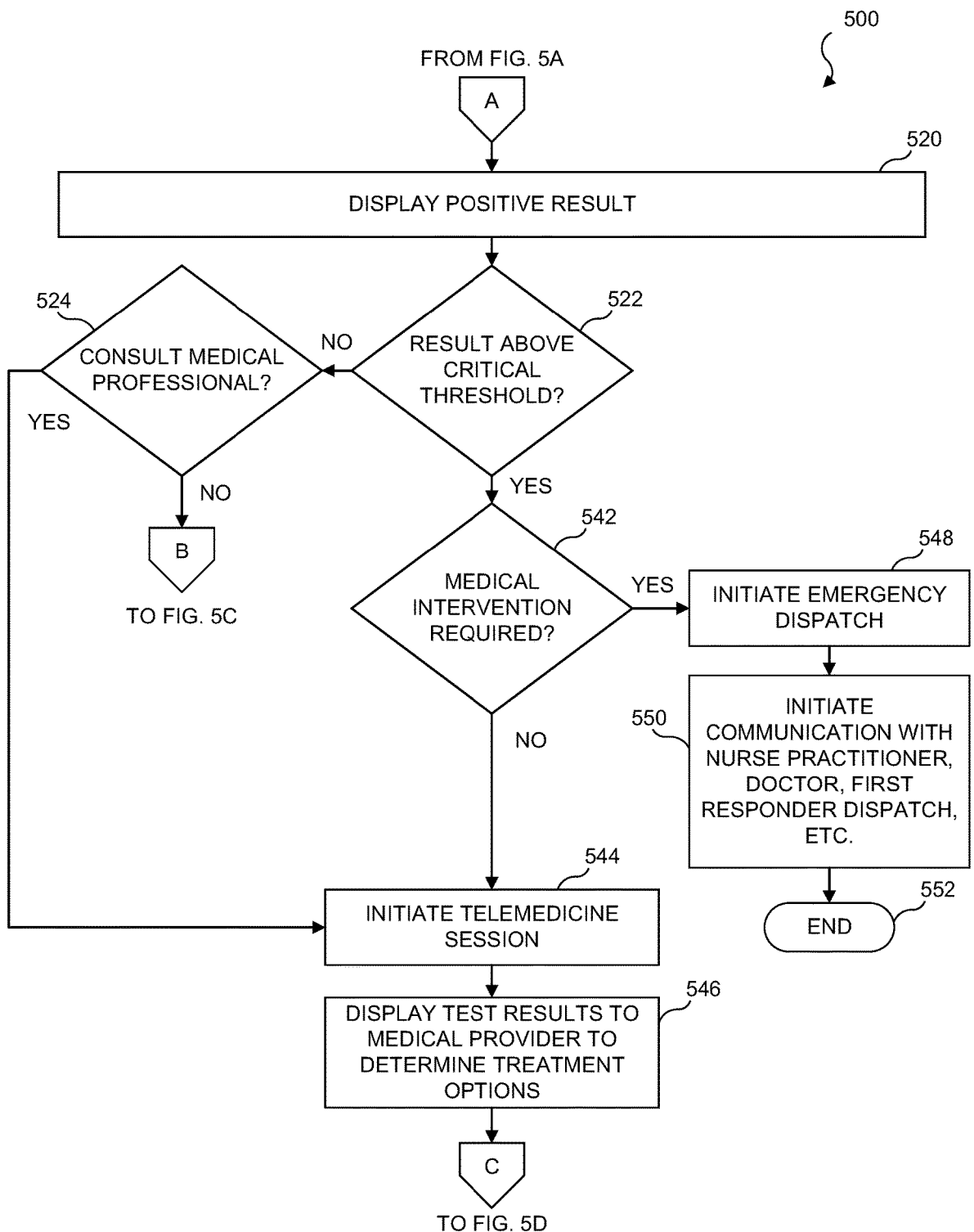
Figure 5C:
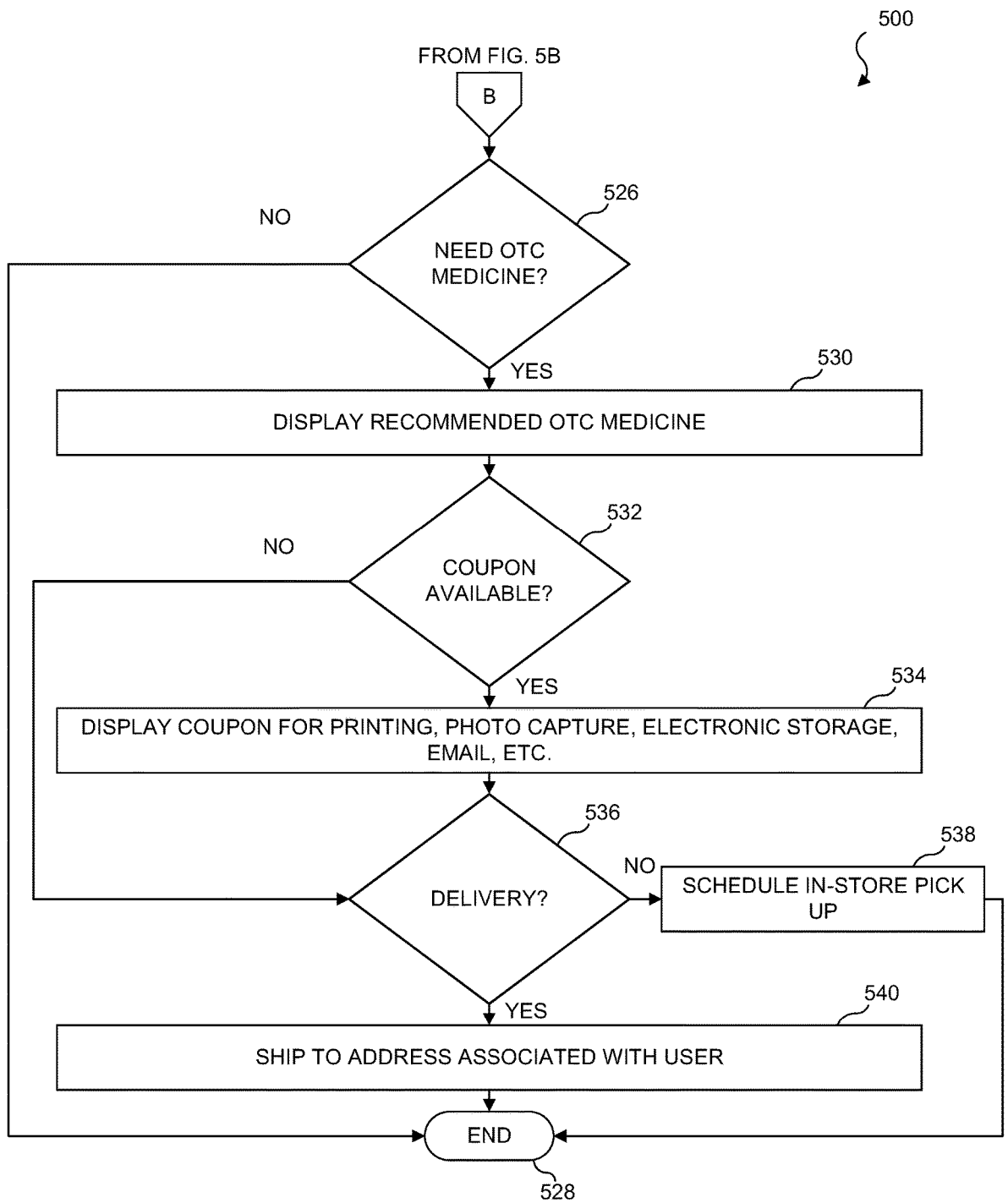
Figure 5D:
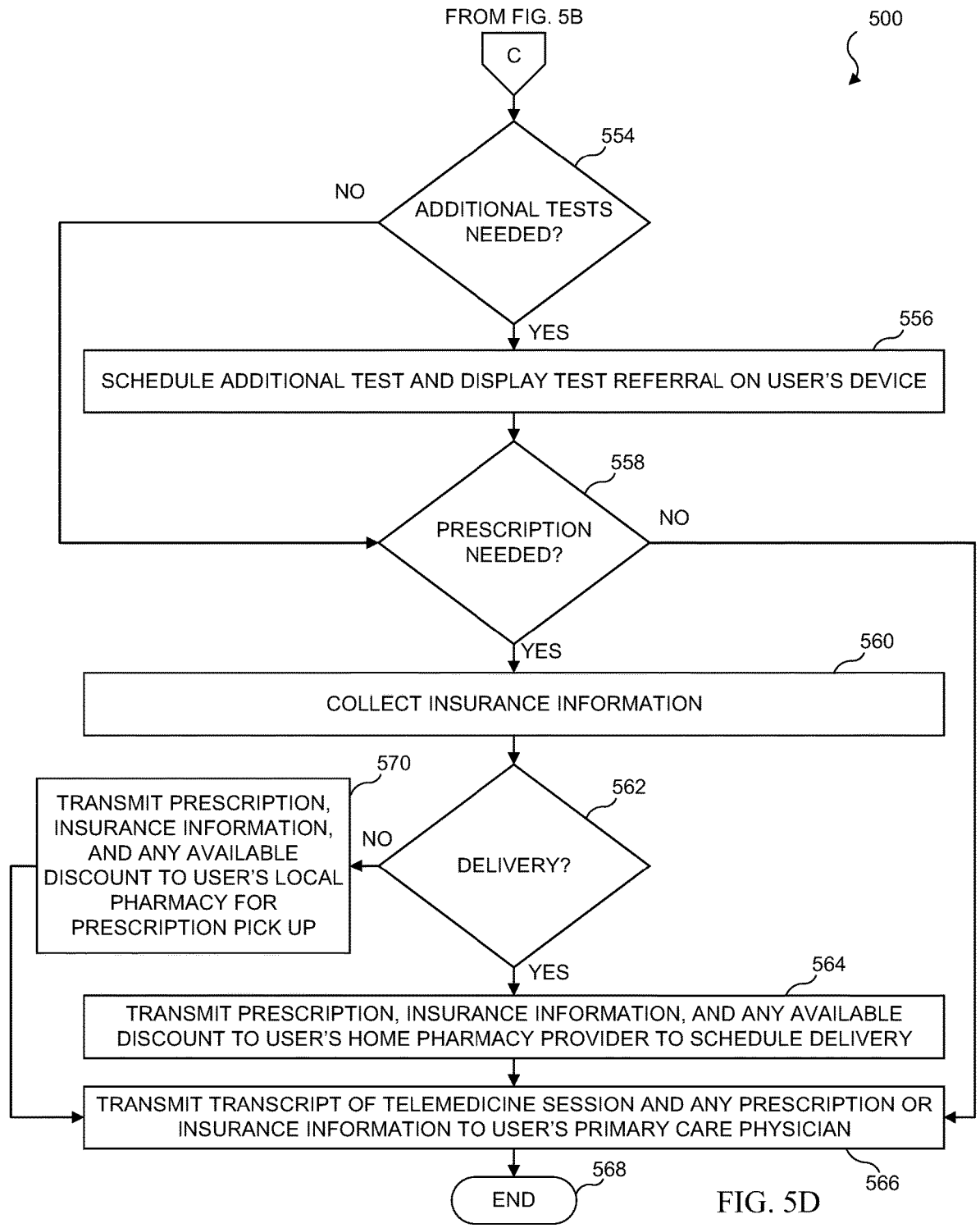

Referring now to FIG. 4K, there is illustrated a data stream 214 for an embodiment in which a unique identifier 212 includes information identifying the user's insurance I.D. In these embodiments, the unique identifier 212 includes an insurance I.D. data stream 422. The insurance I.D. data stream 422 includes information which can be used in a storage database to look up a user's insurance information. This information would be used in situations where the mobile application user indicates that they wish to have the medical test results sent to the healthcare provider, pharmacy, or other entity to allow the user's insurance to be used for a transaction, such as filling a prescription.

Referring now to FIGS. 5A-5D, there is illustrated a biofluidic trigger process 500. The process 500 begins at step 502 where a test using a logical testing unit is performed with a biofluidic input received from a user, client, or application. The logical testing unit may include a testing display and a persistent testing mechanism, and the persistent testing mechanism may include one or more analogical data processors, and one or more persistent antibodies. The analogical data processors may include one or more logical keys. At step 504, media of test results, which are analog results, produced by the testing unit may be captured, such as by a mobile device such as the mobile device 102. The biofluidic input may include or be converted digitally from the analog form thereof to include biofluidic data associated with the type of biofluidic input. The analogical results provided by the testing device or logical testing unit may be first displayed on the display 110 of the mobile device 102 before digital conversion is performed.

At step 506, a unique identifier is generated in accordance with that described herein. At decision block 508, it is determined whether the mobile device has connectivity, such as WiFi or cellular data connectivity to the network 120. If not, the process flows to decision block 510 where it is determined whether the results can be determined locally by the mobile device. In some embodiments, the results of certain biological specimen tests may be able to be determined by the mobile device alone, such as a urinary tract infection (UTI) test. If the test cannot be performed locally by the mobile device, the process loops back to decision block 508 to again check for connectivity. If at step 508 it is determined that the device has connectivity, or if at step 510 it is determined that the test results can be determined locally, the process flows to step 512.

At step 512, the results of the test are determined, either locally be the mobile device or by a remote source such as the server 116 or the database 118. At decision block 514, as described herein, the biofluidic input may be verified by a verification server, such as the server 116, to determine whether the one or more analogical data processors should respond to the biofluidic input. This verification may be used to determine if any specimen was applied at all, if only water was applied, etc. If verification cannot be made, the process 500 loops back to step 502 to have the test performed again. If the specimen is verified, the process moves to decision block 516. At decision block 516, it is determined whether the results of the test are positive. If not, the process flows to step 518 where a negative result is displayed to the user and stored on the server 116 and/or database 118. If at decision block 516 the results are positive, the process flows to step 520 to display the positive result on the mobile device.

At decision block 522, it is determined whether the positive result is above a critical threshold. If not, the process 500 flows to decision block 524, where it is determined whether the user wants to consult a medical professional. If not, the process flows to decision block 526, where it is determined whether the user needs or wants over-the-counter (OTC) medicine. If not, the process ends at end block 528. If so, the process flows to step 530, where one or more recommended OTC medications may be displayed to the user. In some embodiments, a prescription may not be required and an over-the counter (OTC) remedy or medicine is displayed on the client's application program interface. In some embodiments, the application program interface may display to the user an advertisement, discount or coupon to the user for the OTC remedy or medicine during the telemedicine session. In this instance, the medical professional may input a client data package into the application program interface of the professional's mobile device 102. The client data package may include the OTC information, summary of health report, address of the client, phone number of the client, recommendation of follow up with primary care physician, and diagnosis. In some embodiments the client data package is transmitted to the content server, via the network, and saved to the database corresponding to the unique identifier of the user. In some embodiments, the content server may then transmit the client data package to the user's application program interface to display to the user.

At decision block 532 it is determined whether a coupon is available for the one or more recommended OTC medications. In some embodiments, the application program interface may display to the user an advertisement, discount or coupon to the user for the OTC referred during the telemedicine session. In some instances, the client's application program interface may display information to gather flexible spending account information of the client. If so, the process flows to step 534 to display the coupon on the mobile device to allow the coupon to be printed, photo captured such as by taking a screenshot, saved electrically, emailed, etc. The process then flows to decision block 536. If at decision block 532 it is determined that a coupon is not available, the process also then flows to decision block 536. At decision block 536, it is determined whether delivery of the OTC medication is to be made to the user. If not, the process flows to step 538 where in-store pick up is scheduled, the process then flowing to end block 528. If at decision block 536 it is determined that the OTC medication is to be delivered to the user, the process flows to step 540 where the OTC medication is shipped to an address associated with the user, the process then flowing to end block 528. In some embodiments, the client data package, discount or coupon for the prescription, the medical insurance information, or a combination thereof, may be transmitted to a retail store server. The retail pharmacy server may be one of CVS, Walgreens, Target, Walmart, grocery store, Amazon, Amazon Prime Now, and the like. In some embodiments, the prescription may be delivered to the client via delivery services, for instance, Uber, Lyft, and the like. In some embodiments, the prescription may be delivered to the client via delivery services, for instance, Uber, Lyft, and the like.

If at decision block 522 it is determined that the positive result is above a critical threshold, the process flows to decision block 542. At decision block 542, it is determined whether medical intervention is required due to the result being above the critical threshold. If not, the process flows to step 544. If back at decision block 524, it is determined that the user, after it is determined that the result is not above a critical threshold, does not want to consult with a medical professional, the process also then flows to step 544. At step 544, a telemedicine session is initiated. The process then flows to step 546, where the positive test results are displayed to a medical provider so that the medical provider may determine treatment options. In some embodiments, the result from the analog testing device is below a test threshold. In this instance, the user may initiate a telemedicine session with a medical professional via a mobile device 102 with an application program interface. In some embodiments, the user is displayed on the application program interface a medical professional to conference with via the mobile device's audio and video device, i.e. the camera, microphone, speaker, LCD display screen or the like. In some embodiments, the medical professional may authenticate the user and the test results from the analog testing device, gather medical history information from the user, discuss the results of the test with the user, provide medical suggestions based on the results from the testing device and the user's medical history, suggest prescriptions options as a result of the information gather, and the like.

If at decision block 542 it is determined that medical intervention is required, the process flows to step 548 to initiate an emergency dispatch. In some embodiments, the results from the analog testing device may indicate a medical emergency and medical intervention of the medical emergency may occur. In this instance the result from the analog testing device was above a test threshold, which indicates a medical risk. In some cases, medical intervention may be contacting 911, contacting emergency contact, contacting an ambulance service, i.e. private and public services, and the like, via the application program interface. In some instances, the user may be displayed a result on the mobile device 102 that medical intervention has occurred and may be placed in direct contact with 911 dispatch, the emergency contact or the private or public ambulance service. In some embodiments, once medical intervention is indicated, the user may be prevented from ending the testing session. In other instances, the user may be required to provide consent to end the session. Consent may include signing a waiver, creating a digital pin for authentication to electronical sign a waiver or recording a voice message, all indicating consent to end the session without medical intervention. At step 550, while emergency dispatch is en route or even after emergency dispatch arrives, a communication may be initiated between the user and a nurse practitioner, doctor, first responder dispatch, etc., in order to assure the user or walk the user through steps the user may need to perform. The process then ends at step 552. Steps 548 and 550 may in some embodiments be initiated automatically, while not allowing the user to bypass the option, due to the detected critical nature of the user's health.

After step 546, the process flows to decision block 554. At decision block 554, it is determined by the medical provider conducting the telemedicine communication with the user whether one or more additional tests are needed. If so, the medical provider schedules the one or more additional tests, and one or more referrals regarding the additional tests are displayed on the user's device. The process then flows to decision block 558. If at decision block 554 it is determined that additional tests are not needed, the process also then flows to decision block 558.

At decision block 558, it is determined whether a prescription is needed. In some cases, the medical professional may prescribe a medicine in response to the user's telemedicine session. In this instance, the medical professional may input a client data package into the application program interface of the professional's mobile device 102. The client data package may include the prescription information, summary of health report, address of the client, phone number of the client, recommendation of follow up with primary care physician, and diagnosis. In some embodiments the client data package is transmitted to the server 112, via the network 116, and saved to the database corresponding to the unique identifier of the user. In some embodiments, the content server may then transmit the client data package to the user's application program interface for display to the user. If it is determined at decision block 558 that a prescription is needed, at step 560, insurance information pertaining to the user may be collected.

In some embodiments, the application program interface may display to the user an advertisement, discount or coupon to the user for the prescription prescribed during the telemedicine session. In some instances, the client's application program interface may display information to gather medical insurance information of the client. In some instances, the client's application program interface may display information to gather flexible spending account information.

At decision block 562, it is determined whether delivery of the prescription is to be made. If delivery is to be made, the process flows to step 564. At step 564, in some embodiments, the client data package, discount or coupon for the prescription, the medical insurance information, or a combination thereof, may be transmitted to a prescription home delivery server. In this instance, the prescription home delivery server may initiate a home delivery provider to initiate a delivery of the prescription to the client. In some embodiments, the prescription may be delivered to the client via delivery services, for instance, Uber, Lyft, and the like. The process then flows to step 566 to transmit a transcript of the telemedicine session and any prescription or insurance information to the user's primary care physician. The process then ends at end block 568.

If at decision block 558 it is determined that a prescription is not needed, the process flows to step 566 and to end block 568. If at decision block 562 it is determined that delivery of the prescription is not to be made, the process flows to step 570. At step 570, prescription and insurance information, and any available discount, are transmitted to the user's local pharmacy for prescription pick up. In some embodiments, the client data package, discount or coupon for the prescription, the medical insurance information, or a combination thereof, may be transmitted to a retail pharmacy server. The retail pharmacy server may be one of CVS, Walgreens, Target Pharmacy, Walmart Pharmacy, hospital pharmacies, grocery store pharmacies, and the like. The process then flows to step 566 and end block 568.

Figure 6:
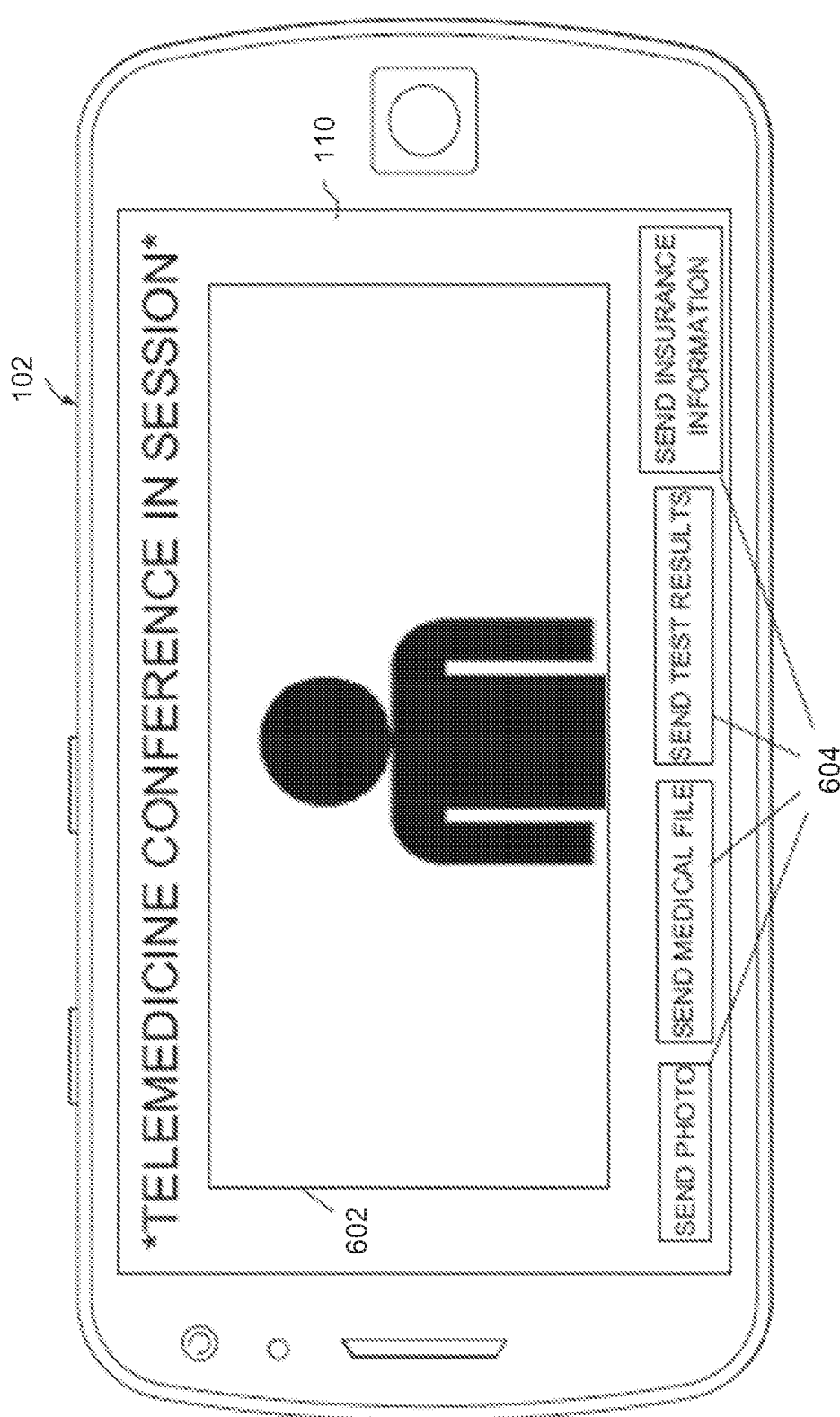
FIG. 6 illustrates one embodiment of a telemedicine conference session on a mobile device.

Referring now to FIG. 6, there is illustrated one embodiment of a telemedicine conference session on a mobile device. During a telemedicine conference that has been initiated as described herein, the user is presented with a video conference window 602 on the display 110. The video conference window 602 allows for user to see the physician that is providing the telemedicine services to the user. It will be understood that the physician may have a similar video window on the device being used by the physician that allows the physician to see the user. This allows the physician to make some visual observations of the user's condition. In addition to the video conference window 602, the user is presented with a plurality of actions 604 on the display 110. The plurality of action 604 may be buttons that allow the user to provide the physician with further information. For example, one button may allow for the user to send a photograph to the physician, such as a photograph of the user's symptoms, or of the user's test results presented on the testing device. One button may also provide an option for sending the user's medical file to the physician, so that the physician can review the user's medical history or other important information. This medical file may include all the information accumulated from all tests performed by the user under the system described herein, and may also include all other medical history information.

The user may have provided a copy of his or her medical history, or such may have been retrieved from a central electronic medical records system.

Other actions that may be provided in the plurality of actions 604 may be a button to send test results to the physician. This would allow the user to send the test results of the latest test the user took before initiating the telemedicine conference, or it may allow for the user to choose the test. The plurality of actions 604 may also include a button for sending the user's insurance information to the physician. The user may have provided this information within the mobile application and had it stored to the server, or this information may have been pulled via a confidential link from a centralized database for the user based on the user's identification information. This option allows the user to give the physician insurance information so that the physician can use the user's insurance for reimbursement of the telemedicine services, and may even set up reimbursement to the user for certain services or products, such as the testing device used for the test.

Figure 7:
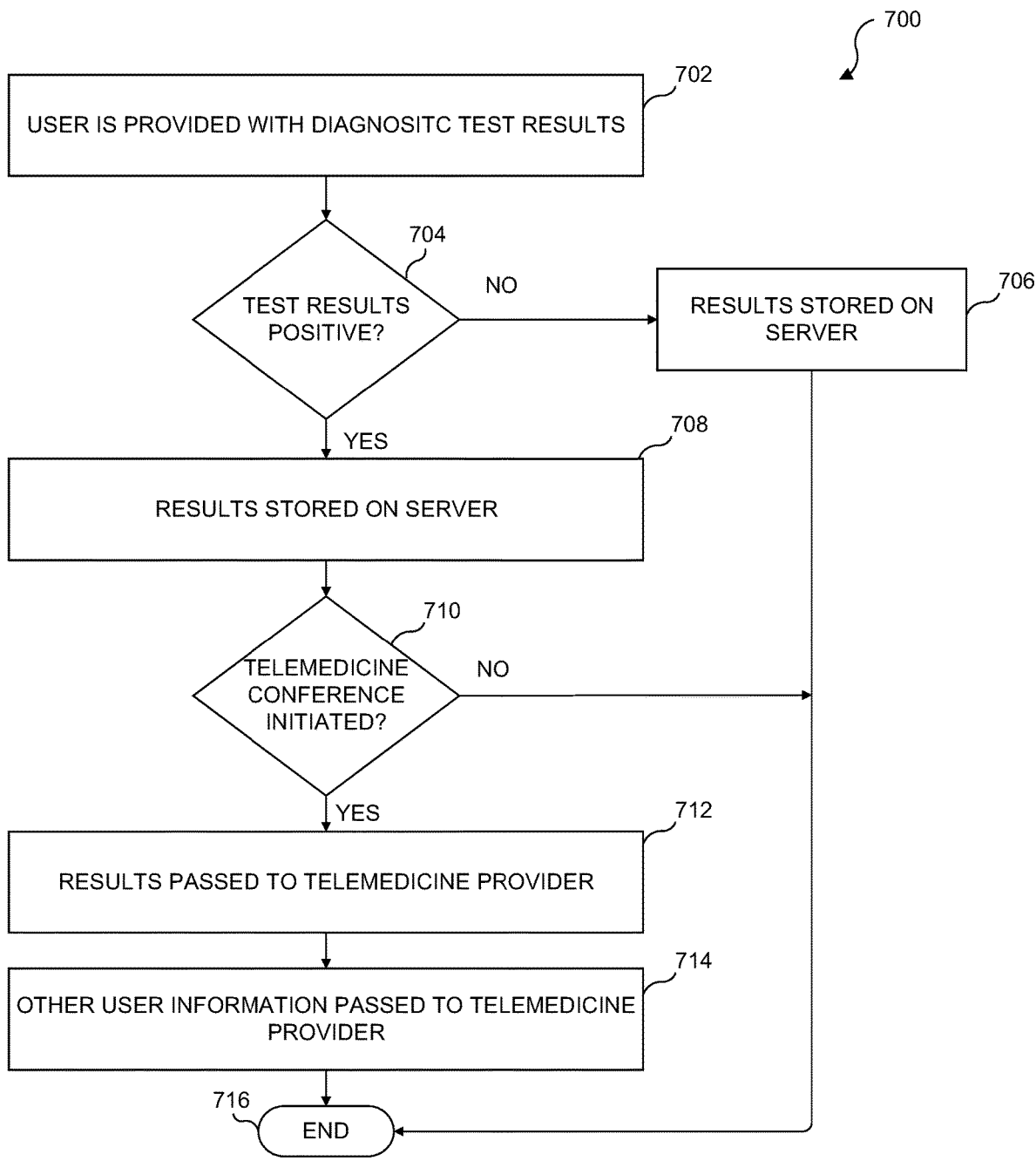
FIG. 7 illustrates a flowchart of one embodiment of a medical file handoff process.

Referring now to FIG. 7, there is illustrated a flowchart of one embodiment of a medical file handoff process 700. The process 700 starts at step 702 where a user is provided with diagnostic test results at the conclusion of a performance of a test. At decision block 704, it is determined whether the test results provide a positive result. If not, at step 706 the results are stored on the server of the system described herein and the process ends at end block 716. If the results are positive, the process flows to step 708 where the results are stored on the server. At step 710, it is determined whether a telemedicine conference has been initiated. This may have been automatically initiated due to the results provided, or may have been initiated in some other way. If the telemedicine conference was not initiated, the process ends at end block 716. If the telemedicine conference was initiated, the process flows to step 712 where the test results are passed to the telemedicine provider participating in the telemedicine conference. The process then flows to step 714, where other user information is passed to the telemedicine provider. The process then ends at end block 716.

The passing of the results to the telemedicine provider and other information at steps 712 and 714 may be performed by the user's mobile device, wherein the mobile device sends the files to the telemedicine provider. The passing may also be done by the server of the system described herein, wherein the results and other information were previously stored to the server and the server then passes the results and other information to the telemedicine provider as a result of the server being notified of a telemedicine conference initiation. The other user information of step 714 may be any information needed by the telemedicine provider, such as past medical records and medical history of the user, past test results, insurance information, or any other information.

Figure 8:
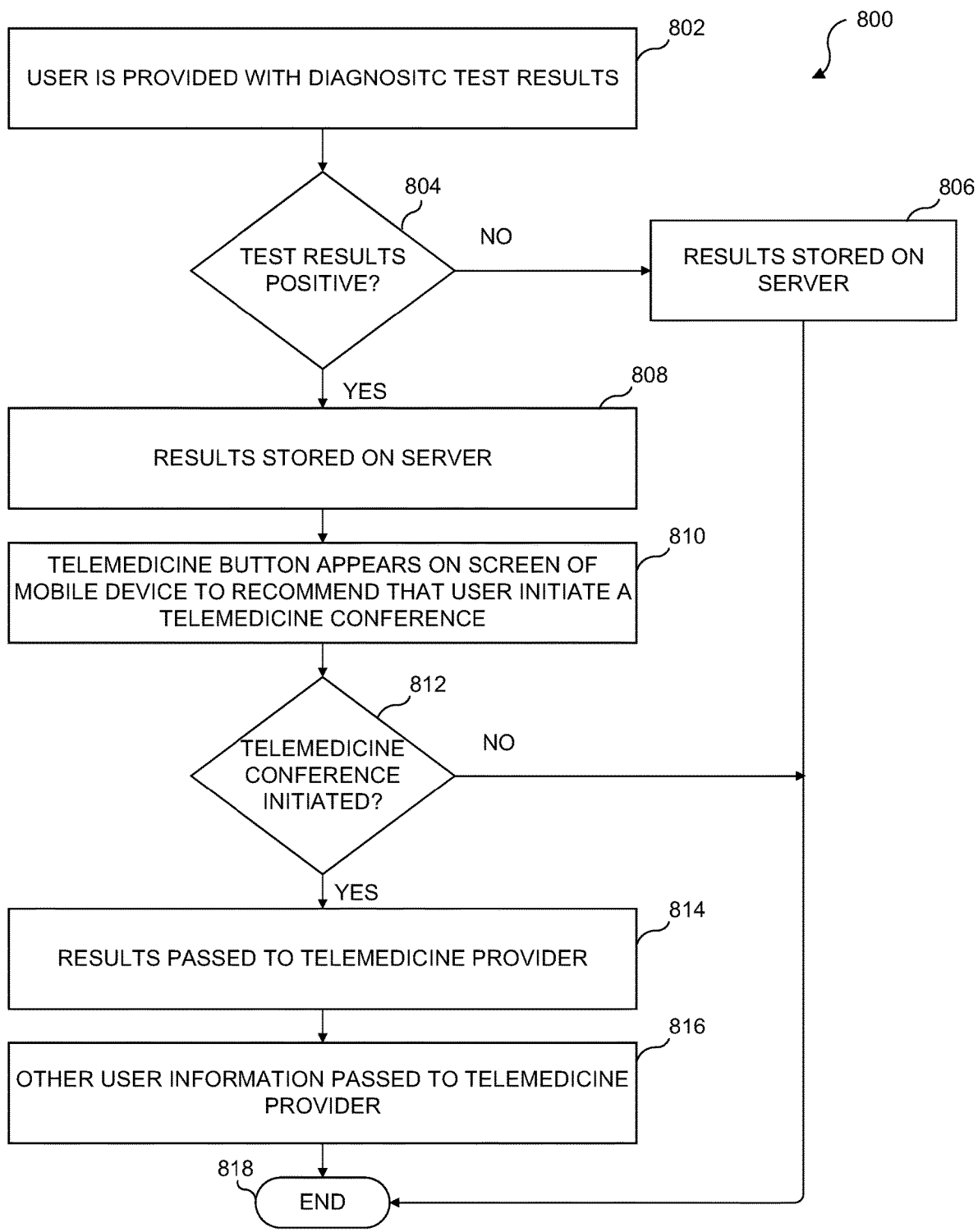
FIG. 8 illustrates a flowchart of one embodiment of a telemedicine conference initiation process.

Referring now to FIG. 8, there is illustrated a flowchart of one embodiment of a telemedicine conference initiation process 800. The process 800 starts at step 802 where a user is provided with diagnostic test results at the conclusion of a performance of a test. At decision block 804, it is determined whether the test results provide a positive result. If not, at step 806 the results are stored on the server of the system described herein and the process ends at end block 818. If the results are positive, the process flows to step 808 where the results are stored on the server. At step 810 a telemedicine button is presented to the user on the screen of the mobile device, similar to that shown in FIG. 28. This button recommends to the user that the user initiate a telemedicine conference, since the test results indicate a positive reaction. At step 812, it is determined whether a telemedicine conference has been initiated. This may have been automatically initiated due to the results provided, or may have been initiated in some other way. If the telemedicine conference was not initiated, the process ends at end block 818. If the telemedicine conference was initiated, the process flows to step 814 where the test results are passed to the telemedicine provider participating in the telemedicine conference. The process then flows to step 816, where other user information is passed to the telemedicine provider. The process then ends at end block 818.

The passing of the results to the telemedicine provider and other information at steps 814 and 816 may be performed by the user's mobile device, wherein the mobile device sends the files to the telemedicine provider. The passing may also be done by the server of the system described herein, wherein the results and other information was previously stored to the server and the server then passes the results and other information to the telemedicine provider as a result of the server being notified of a telemedicine conference initiation. The other user information of step 816 may be any information needed by the telemedicine provider, such as past medical records and history of the user, past test results, insurance information, or any other information.

Figure 9A:
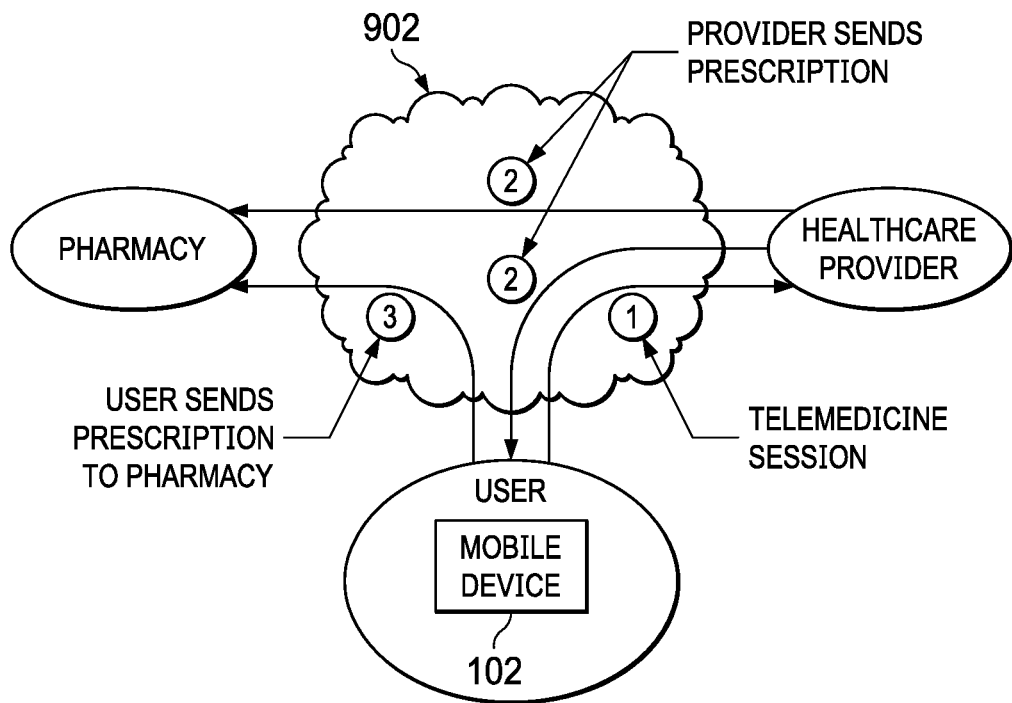
FIGS. 9A and 9B illustrate systems for transmitting prescriptions to a pharmacy using telemedicine.

Referring now to FIG. 9A, there is illustrated an embodiment of a system in which a prescription is transmitted to a pharmacy using a medical test and telemedicine. In these embodiments, rather than the patient needing to physically travel to a pharmacy to drop off a prescription to be filled, the user uses a mobile application to electronically transmit the prescription information to the pharmacy. These embodiments improve upon embodiments which use medical tests and telemedicine and take advantage of the fact that the user is already engaged in a telemedicine session with the user's healthcare provider through a network 902 such as the internet. In these embodiments, the user engages in a telemedicine session with a healthcare provider as described herein, via Path □. When the user and the healthcare provider complete the telemedicine session, the healthcare provider can prescribe necessary medicine to the mobile application user. However, since the user is not physically present with the healthcare provider, the user does not pick up a physical prescription slip. Instead, the healthcare provider transmits via Path □ the prescription in electronic form either to the user's mobile application, or to the pharmacy of the user's choice. If the healthcare provider transmits the "electronic prescription" to the user's mobile application, then the user can then store the electronic prescription on his mobile device 102 in the mobile application until he is ready to get the prescription filled. The user then uses the mobile application to send the electronic prescription to the pharmacy via Path □. The pharmacy then fills the prescription as normal.

Figure 9B:
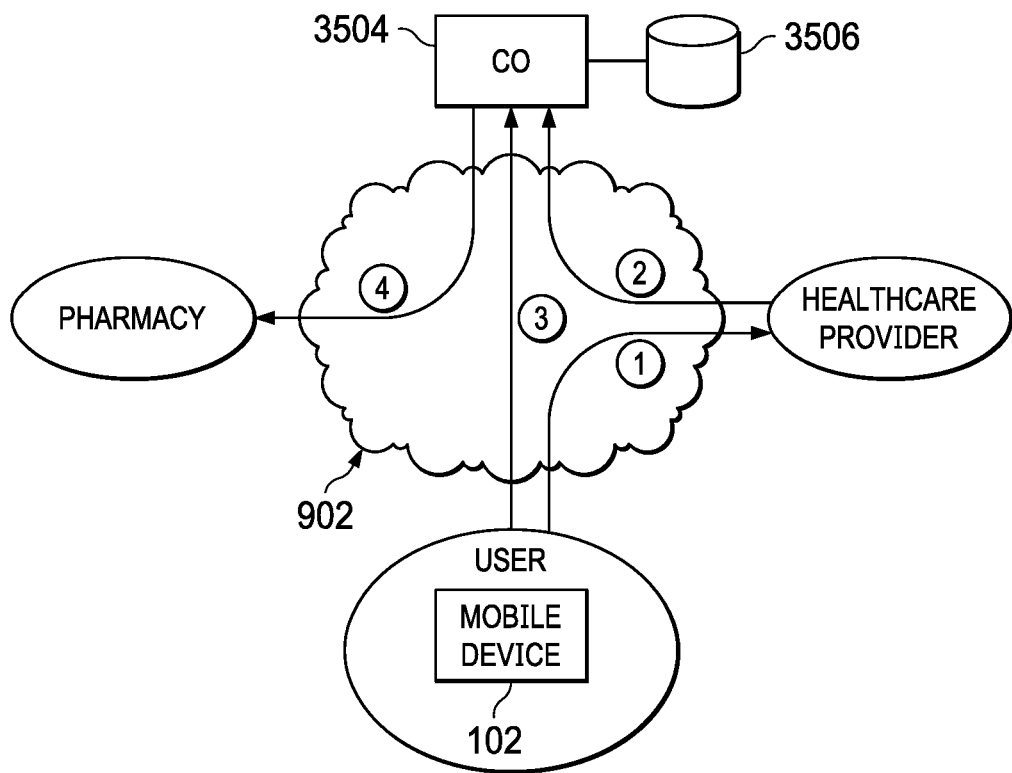

Referring now to FIG. 9B, there is illustrated another embodiment of a system in which a prescription is transmitted to a pharmacy using a medical test and telemedicine. These embodiments are similar to those described herein with respect to FIG. 9A. The system includes a user with a mobile device 102 running a mobile application, a healthcare provider, a pharmacy, and a remote server or central office with a records database. In these embodiments, the user participates in a telemedicine session with a healthcare provider via Path ☐ as described herein. Next, if the healthcare provider decides that a prescription is needed, the healthcare provider creates a prescription record and transmits the record through a network 902 such as the internet to a central office 904 or remote server via Path ☐. The central office 904 then stores the record in a records database 906. When the user is ready to have their prescription filled, they use the mobile application on the mobile device 102 to contact the central office 904 via Path ☐. The central office 904 then retrieves the prescription record from the database 906 and sends the prescription record to the pharmacy via Path ☐ to have the prescription filled. With this method, the healthcare provider does not have to worry about which pharmacy to send the prescription to, and the fact that the prescription record does not have to be stored on the mobile device 102 means that the user could potentially access the prescription record from another mobile device or any other compatible device with network access.

Figure 10:
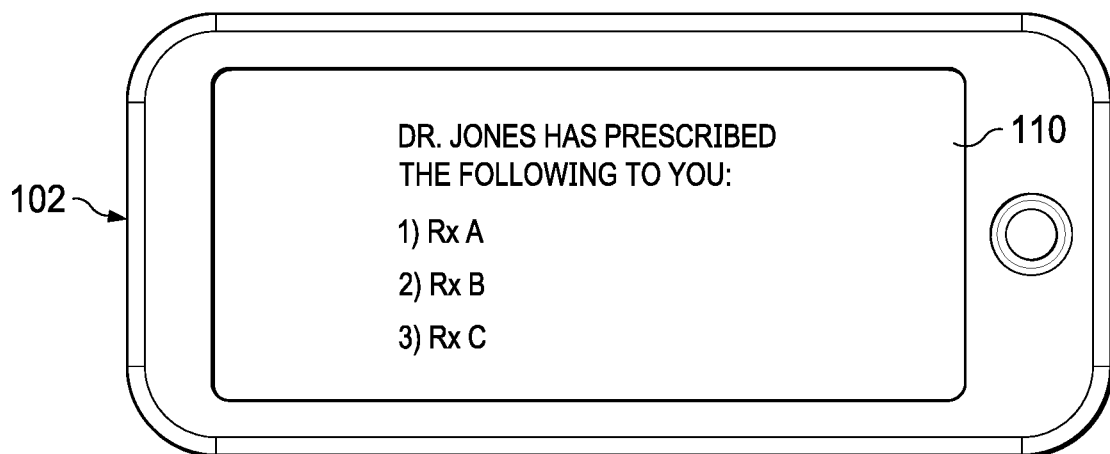
FIG. 10 illustrates an embodiment which uses a mobile application to inform the user which prescriptions have been prescribed

Referring now to FIG. 10, there is illustrated an embodiment in which the mobile application running on the mobile device 102 displays what prescriptions have been prescribed by the healthcare provider to the user. In these embodiments, the mobile application informs the user what prescriptions have been issued or "written" for him by the healthcare provider without the need of physical records. The user receives a notification from the mobile application when the healthcare provider has given the prescription. For example, if the healthcare provider issues ("writes") the prescription during the telemedicine session, the screen illustrated in FIG. 10 will be presented at that time. Or, if the healthcare provider writes the prescription after the telemedicine session has ended, the user will be notified by the mobile application at that time.

Figure 11:
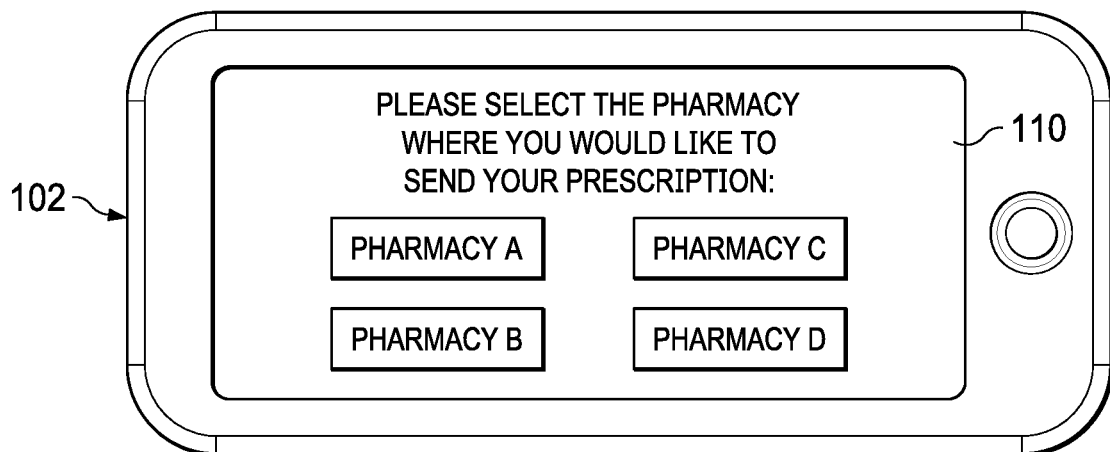
FIG. 11 illustrates an embodiment which uses a mobile application to let a user decide which pharmacy will fill a prescription.

Referring now to FIG. 11, there is illustrated a mobile device 102 from an embodiment in which the user can select which pharmacy to send the prescription to. In these embodiments, a menu displays a choice of pharmacies. These choices can be based on geographic location, on which pharmacies accept the user's insurance, or any other factor which might influence a user's choice of pharmacy. Once the user selects which pharmacy will fill the prescription, the prescription record is transmitted to that pharmacy so that it can be filled. In some embodiments, a preferred pharmacy is selected ahead of time, so that the user does not have to select a pharmacy each time the user receives a prescription from a healthcare provider. In these embodiments, the user is presented instead with a confirmation screen which user will use to send the prescription to the previously-chosen pharmacy to be filled.

Figure 12:
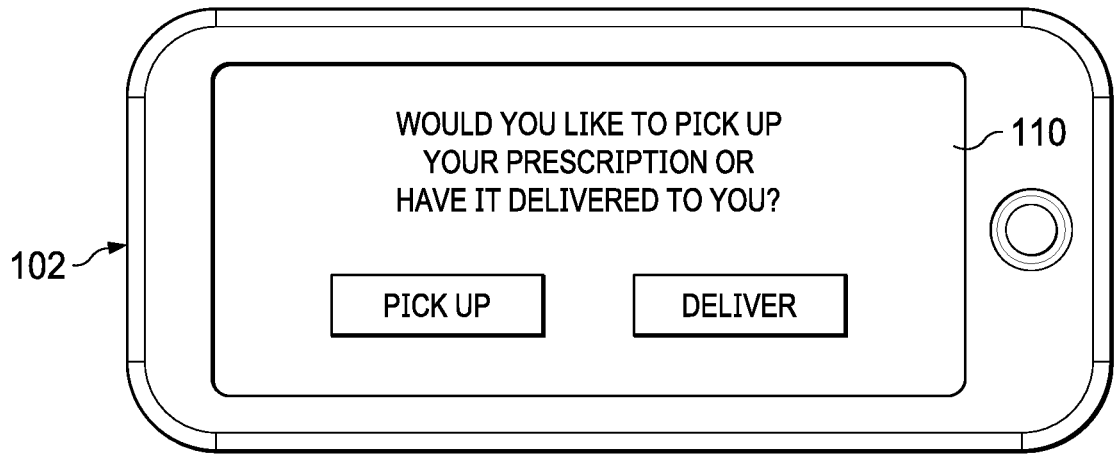
FIG. 12 illustrates an embodiment in which the user can select on a mobile application whether to pick up a prescription or have the prescription delivered.

Referring now to FIG. 12, there is illustrated a mobile device 102 from an embodiment of the system which allows for the prescription to either be picked up or delivered. In some embodiments of the system, the user is offered the convenience of having the prescription delivered to the user's home or place of work. In these embodiments, when a prescription is sent to a pharmacy to be filled, the user is presented with a menu in the mobile application which gives him the option of choosing to pick up the prescription himself, or of having the prescription delivered. If the user selects to have the prescription delivered, the user will then be presented with a screen in the mobile application where he or she enters the delivery address. Some embodiments will allow for addresses to be pre-entered into the mobile application and saved. This will speed up future prescription fillings, as the user will not have to enter the delivery address every time he selects to have a prescription delivered. In some embodiments, if the user selects to pick up the prescription, the user will be given an estimated ready time for the prescription or a notification through the mobile application when the prescription is ready to be picked up.

Figure 13:
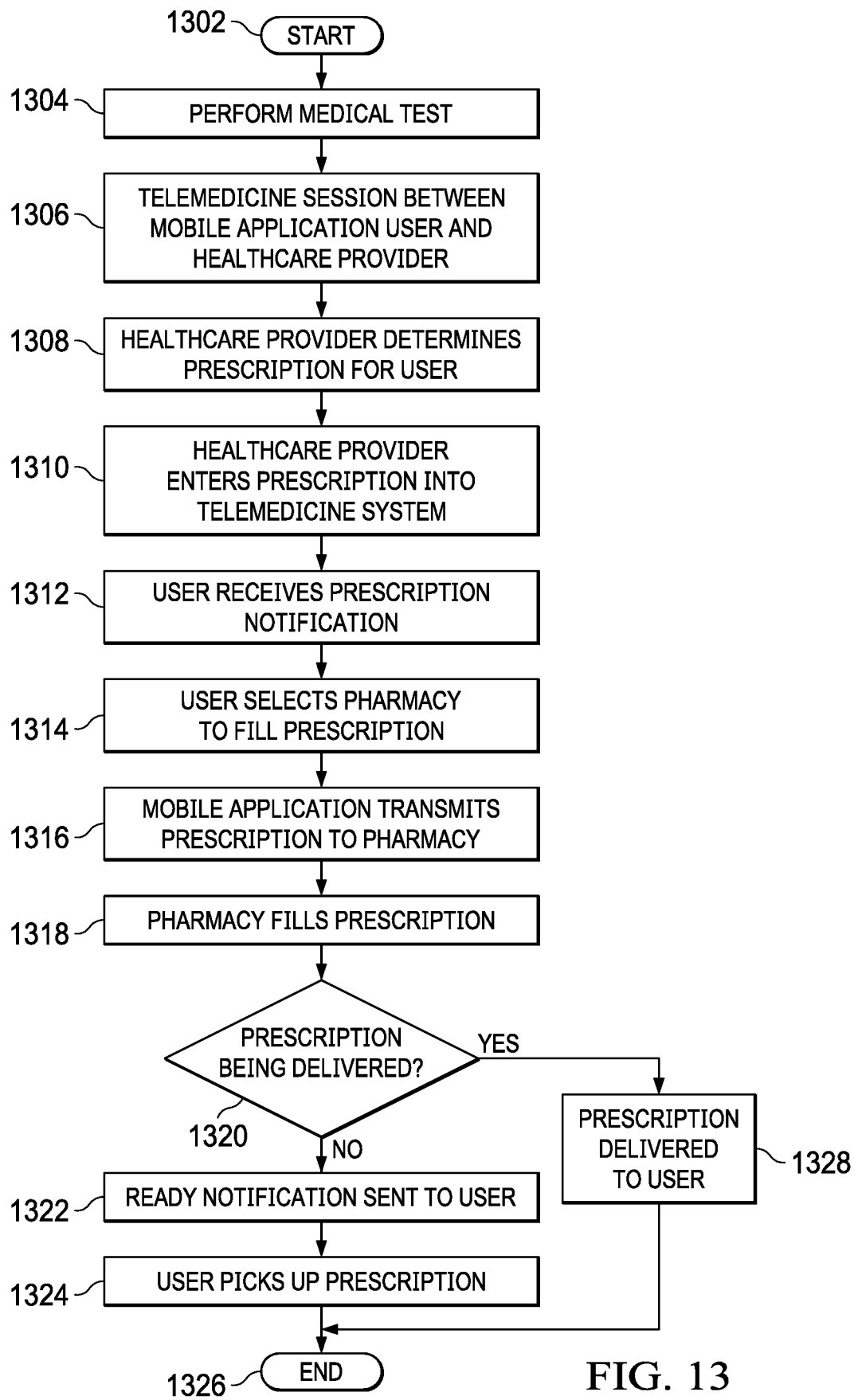
FIG. 13 illustrates a flowchart depicting a process for filling a prescription using a medical test and a telemedicine session.

Referring now to FIG. 13, there is illustrated a flowchart of the process for using a medical test and telemedicine to obtain a prescription. The process starts at Start block 1302 and proceeds to block 1304. At block 1304, the user performs a medical test such as is described herein. Next, at block 1306, a telemedicine session is established and occurs between the user and a healthcare provider as described herein. Next, the process moves to block 1308, where the healthcare provider determines that the user needs a prescription. In some embodiments, this step takes place during the telemedicine session. Next, the process moves to block 1310, where the healthcare provider issues a prescription for the user and enters the prescription information into the telemedicine system. Next, at block 1312, the user is notified through the mobile application that they have been prescribed medication. The process then moves to block 1314, where the user selects a pharmacy to fill the prescription. This step may not take place if the user has a pharmacy pre-selected. Next, at block 1316, the mobile application causes the prescription to be sent to the pharmacy to be filled. The process then moves to block 1318, where the pharmacy fills the prescription. The block then moves to decision block 1320, where the user chooses whether the prescription will be picked up or delivered. If the user chooses to pick up the prescription, the process moves to function block 1322, where the system sends the user a notification that the prescription is ready for pick-up. The process moves to block 1324, where the user picks up the prescription and then ends at block 1326. If the user chooses to have the prescription delivered, then the process moves to block 1328, where the prescription is delivered to the user at his selected address. The process then ends at block 1326.

Figure 14:
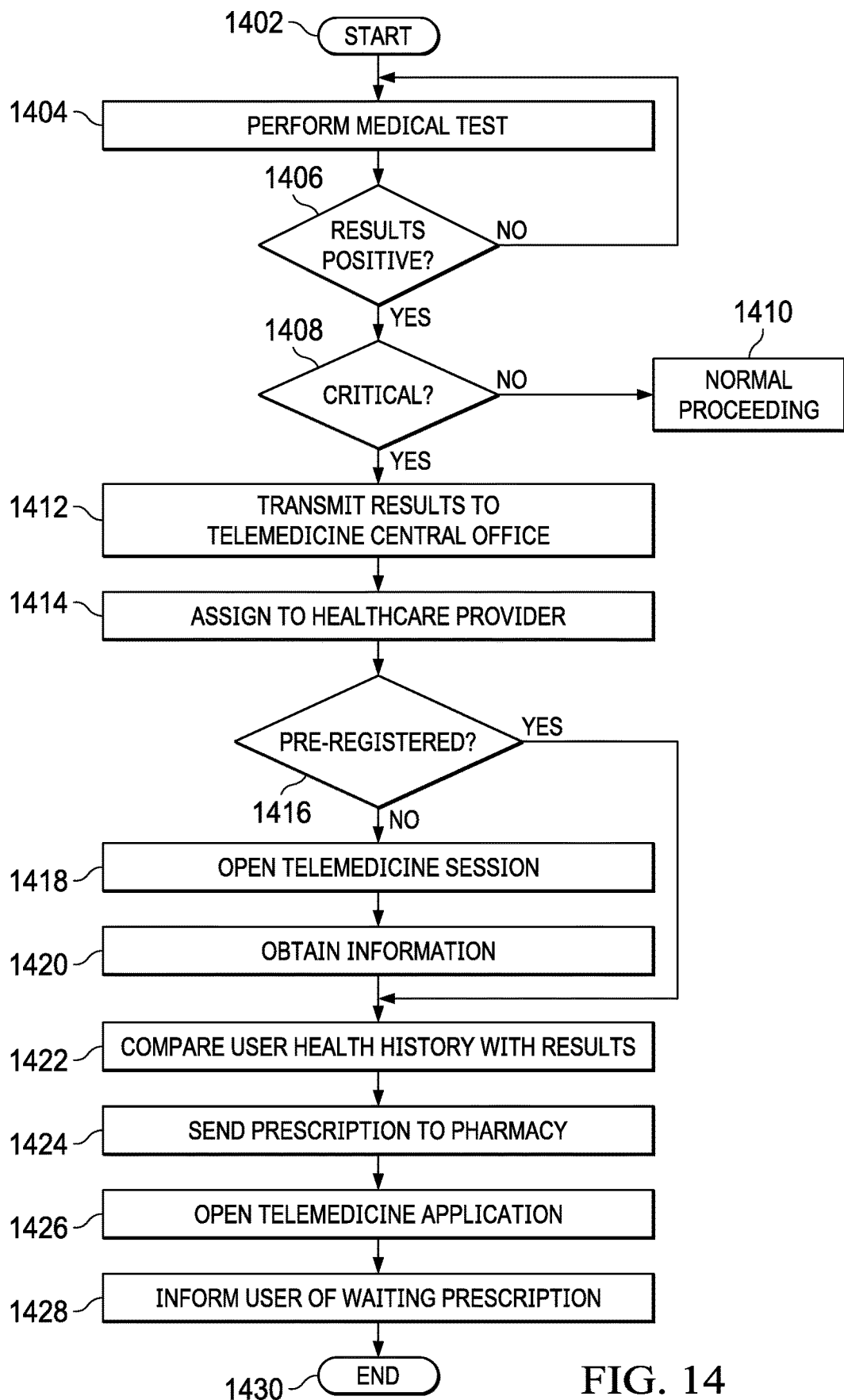
FIG. 14 illustrates an embodiment in which a telemedicine mobile application is used to automatically fill a prescription.

Referring now to FIG. 14, there is illustrated an embodiment in which a telemedicine mobile application is used to automatically fill a prescription. In some cases, when a patient is diagnosed with a particular ailment, the prescription is likely to be a predetermined medication or set of medications. In these cases, a healthcare provider can often issue a prescription for the user without having to actually see or talk to the user. Having a user's health history and the results of a diagnostic test are often enough for a healthcare provider to issue a prescription for a user. Some embodiments take advantage of these situations and improve the efficiency of the telemedicine and prescription-filling process by allowing prescriptions to be issued and filled automatically, without significant interaction between the user and the healthcare provider. The process starts at Start block 1402 and proceeds to function block 1404, where the user performs a medical test. The process then moves to decision block 1406. If the medical test returns negative results, the process loops back to block 1404 until the user performs another medical test sometime in the future. If the test results are positive, the process moves to decision block 1408. If the positive result from the test does not indicate a "critical" or urgent situation, the process movies to block 1410, where a normal telemedicine proceeding occurs, as described herein. If, however, the results indicate an urgent or critical situation which can be resolved without significant user interaction with a healthcare provider, the process moves to function block 1412. At block 1412, the mobile application transmits the medical test results to a central office or remote server for the telemedicine system. The process moves to block 1414, where a healthcare provider is assigned to the user's test results, which are transmitted by the central office to the healthcare provider. The process then moves to decision block 1416, where, if the user has pre-registered, that is, has supplied their health history and pharmacy preferences to the telemedicine system, the process moves to block 1422, where the healthcare provider compares the user's health history with the medical test results to determine if a prescription should (can) be issued to the user.

If, at block 1416, the user has not pre-registered, the process moves to block 1418, where a session of the telemedicine application is opened on the user's mobile device. This session is simply for the user to provide the information necessary for the healthcare provider to issue the proper prescription. The process moves to block 1420, where the user provides their health history and their pharmacy preferences to the telemedicine system through the mobile application. Next, the process move to block 1422, where the healthcare provider compares the user's health history and the test results to determine if a prescription should be issued. The process then moves to block 1424, where the healthcare provider issues a prescription and sends it to the pharmacy. The process moves next to block 1426, where the telemedicine application opens on the user's mobile device. At block 1428, the telemedicine mobile application informs the user that the prescription has been filled by the pharmacy and is ready for pick-up or delivery. The process then ends at End block 1430.

Referring now to FIG. 15, there is illustrated an embodiment of a system which utilizes a remote diagnostic test to initiate a medical escalation and intervention. In some situations, the result of a medical diagnostic test will indicate that immediate or urgent medical attention is needed for the patient. In some embodiments, medical attention will be summoned automatically in these situations. In these embodiments, the user performs a medical test and uses a mobile application running on a mobile device 102 to capture an image of the test product, as described herein. The mobile application then transmits, via Path ☐, the test information through a network 1502 to a remote server or central office 1504. The central office 1504 accesses a database 1506 for the necessary information to generate a result for the medical test. The central office 1504 may also retrieve from the database 1506 criteria for determining whether or not a medical escalation or intervention is warranted on the basis of the test results. The central office 1504 generates a test result and checks the criteria to determine if medical escalation is needed. If no medical escalation is needed, the central office 1504 simply returns, via Path ☐, the test results to the mobile device 102 through the network 1502. If, however, the central office 1504 determines that some type of medical escalation is warranted, then the central office transmits, though the network 1502 via Path ☐, the test and test result information, along with information about the user (such as any relevant personal, demographic and/or contact information collected from the user) to a healthcare provider 1508. Alternatively, instead of the healthcare provider 1508 being contacted by the central office 1508, in some embodiments, the fact that a medical escalation is needed is transmitted along with the test results from the central office 1502 through the network 1502 via Path ☐ to the mobile device 102 running the mobile application. The mobile device 102 then transmits the test and test result information to a healthcare provider 1508 through the network 1502 via Path ④.

The manner of the medical escalation or intervention varies depending on the embodiment, and may vary depending on the type of test and/or the test results. In some embodiments, the escalation takes the form of notifying emergency medical personnel, rather than a healthcare provider 1508, of an urgent medical situation. In these embodiments, the central office may call 911 or in some other way notify emergency services These embodiments would be useful, for example, if a blood test shows that the medical test user has near fatal levels blood sugar or that the user is having a heart attack or stroke. In other embodiments, the medical escalation takes the form of the mobile application on the mobile device automatically initiating a telemedicine session with a healthcare provider 1508. These embodiments are useful, for example, in urgent, but not quite emergency, situations. For example, elevated blood sugar or high blood pressure might not be immanently deadly to a patient, but should still be addressed and brought to the attention of a healthcare 1508 provider quickly. In other embodiments which are most useful for urgent—but not quite emergency—situations, the central office 1504 notifies the healthcare provider 1508 of the test results, and leaves it up to the healthcare provider to determine the best next course of action to take with respect to the patient.

Referring now to FIG. 16, there is illustrated an example of a table which would be found in the database of a central office 1506 and which contains criteria for when to initiate a medical intervention based on the results of a remote diagnostic test. The table 1602 includes several columns of information. In the example embodiment depicted in FIG. 16, the diagnostic test is a quantitative one which produces a numerical rating as part of the test result, similar to the embodiments described herein. An example of such a test could be a blood glucose test, wherein a certain risk is generally associated with a range of glucose levels. In this example, a low test result "rating" indicates a low health risk for the condition being tested, while a higher "rating" indicates a higher risk. In the some embodiments which use a table such as table 1602, different types of medical intervention are used for different test results. The first column 1604 of table 1602 specifies a range of test result "ratings," while the rest of the columns 1604, 1606, and 1608 specify information correlating to that rating range. Column 1606 specifies the health risk associated with a particular test result rating from column 1604, and column 1608 specifies what type of medical intervention will be initiated for a test result within a given range. For example, if a user conducts the example medical test, and the central office 1504 generates a test result rating of 57 (which indicates a dangerous health risk), then the central office will not only return the test result to the user, it will also initiate an urgent medical intervention, such as initiating a telemedicine session between the user and a healthcare provider. If the central office 1504 generates a test result rating of 93 (which would indicate a deadly health risk), then the central office will initiate an emergency health intervention, such as notifying emergency medical services of the user's condition. On the other hand, if the test result rating is in the "NORMAL" or "ELEVATED" range, then no medical intervention will be initiated, and the central office 1504 will simply return the test results to the user and the mobile device 102. Naturally, other embodiments will have different styles of tables in the central office 1504 database. Some embodiments which have qualitative rather than quantitative tests (for example, testing simply "positive" or "negative" for a disease) will not have various multiple different types of medical intervention.

Referring now to FIG. 17, there is illustrated a mobile device 102 from an embodiment in which a medical intervention in the form of a telemedicine session is initiated on a mobile device in response to a diagnostic test. In the example illustrated in FIG. 17, the mobile application running on the mobile device 102 displays that a medical test performed by a user has returned a result showing the user has dangerous levels of blood glucose. As described herein, different embodiments will have different types of medical intervention. In the example of FIG. 17, the mobile application automatically initiates a telemedicine session in response to the high blood glucose test result. The mobile application informs the user that the test results indicated a dangerous glucose level, initiates the telemedicine session, and transmits the test results to the healthcare provider (some embodiments transmit the test results to the healthcare provider directly from the central office 1504).

Figures 18, 19:
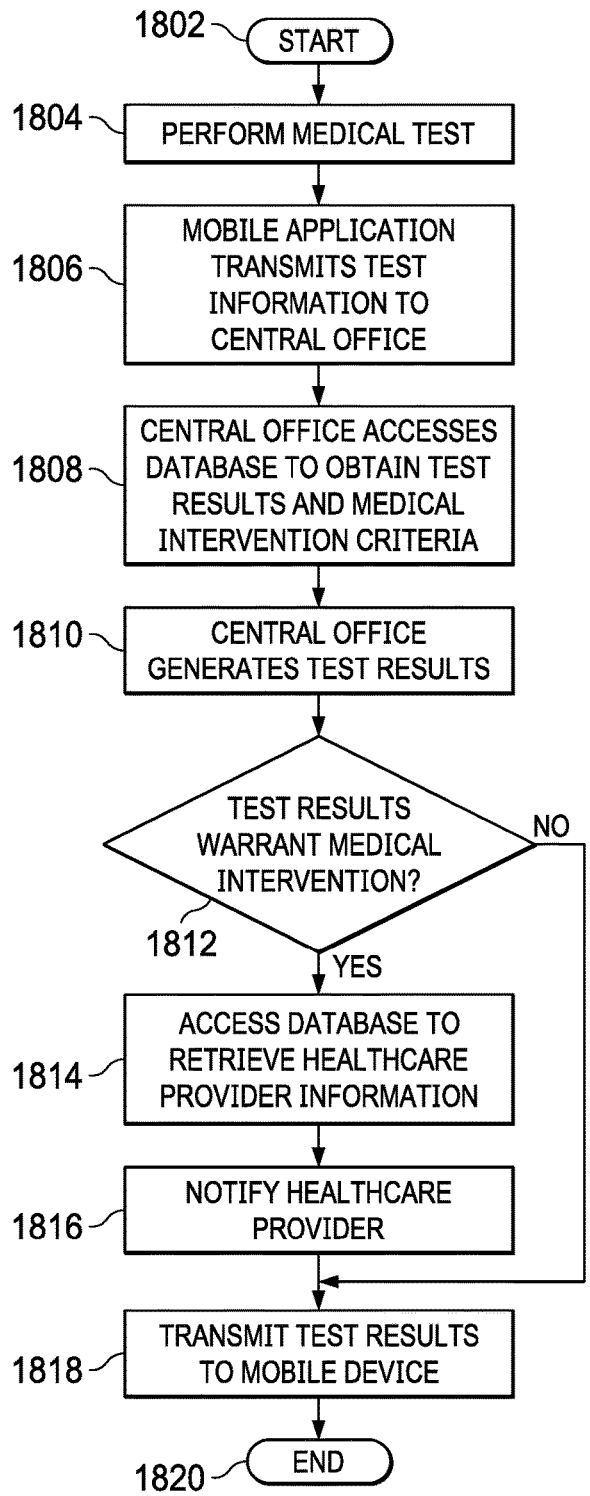
FIG. 18 illustrates a flowchart for an embodiment which initiates a medical escalation or intervention as a result of a remote diagnostic test.
FIG. 19 illustrates an embodiment which includes mapping a diagnostic test to an individual user to create a unique profile on a remote database.

Referring now to FIG. 18, there is illustrated a flowchart for an embodiment which initiates a medical escalation or intervention as a result of a remote diagnostic test. The process starts at START block 1802. Next, the process moves to function block 1804, where the user performs a medical test and reads the testing equipment with a mobile device, such as is described herein. Next, at block 1806, a mobile application on the mobile device transmits the test information, including the image or images of the captured by the mobile device, to a central office over a network 1502. The process flows to block 1808, where the central office 1504 accesses a connected database 1506 to obtain information for generating a test result, as well as information detailing the criteria for initiating a medical intervention. Next, at block 1810, the central office 1504 generates test results based on the information transmitted from the mobile device 102 and the information obtained from the database 1506. At decision block 1812, the central office 102 determines whether or not, based on test results, a medical intervention is warranted. If a medical intervention is warranted, the process flows to block 1814, where the central office accesses the database 1506 to retrieve healthcare provider information for the user. The process then proceeds to block 1816, where the central office 1504 notifies the healthcare provider 1508 of the test results. Next, the process moves to block 1818, where the central office 1504 transmits the test results to the mobile device 102 through the network 1502. The process then ends at END block 1820. If, at decision block 1812, no medical intervention is warranted, then the process instead moves to block 1818 and block 1820, as described herein.

Referring next to FIG. 19, there is illustrated an embodiment which includes mapping a diagnostic test to an individual user to create a unique profile on a remote database. Each time a patient conducts a medical test, there is a change to gather information about that patient and the patient's test. Instead of each piece of information about a patient or a test being regarded individually, multiple data points and pieces of information for a common patient can be associated with each other, providing a greater insight into and creating a detailed profile of the patient. Referring to FIG. 19, there is illustrated a unique profile record 1900. Each unique profile record 1900 is associated with an individual patient or diagnostic test user and has a unique ID 1902. The unique profile record 1900 contains information associated with the patient/user, such as the patient name 1904, the name of a healthcare provider 1906 associated with the patient, or the name of a pharmacy 1908 associated with the patient. Importantly, the unique profile record 1900 also includes the biologic IDs 1910 associated with the user. Each biologic ID 1910 is the same ID as the biologic header 2002 in one of the unique biologic ID database tables 2000. Thus, the unique profile record 1900 includes a "link" to the record of each biologic used by the patient associated with the unique profile record. Each time a diagnostic test is conducted on a biologic sample, the biologic sample is associated with the unique profile record 1900, which means the unique biologic ID database table 2000 (which includes data about the test) is associated with the unique profile record 1900 and the user. This means that more information about the patient is collected and accumulated.

Different embodiments will include different types of data to be stored within each unique profile record 1900. In some embodiments, the unique profile record 1900 includes information about food or medications to which the patient is allergic. Some embodiments of the unique profile record 1900 include records of which illnesses which the patient has had. Virtually any type of information related to the patient/user can be included in the unique profile record 1900 in various embodiments, so long as it contributes to construction of a better "picture" of the patient/user.

Figure 20:
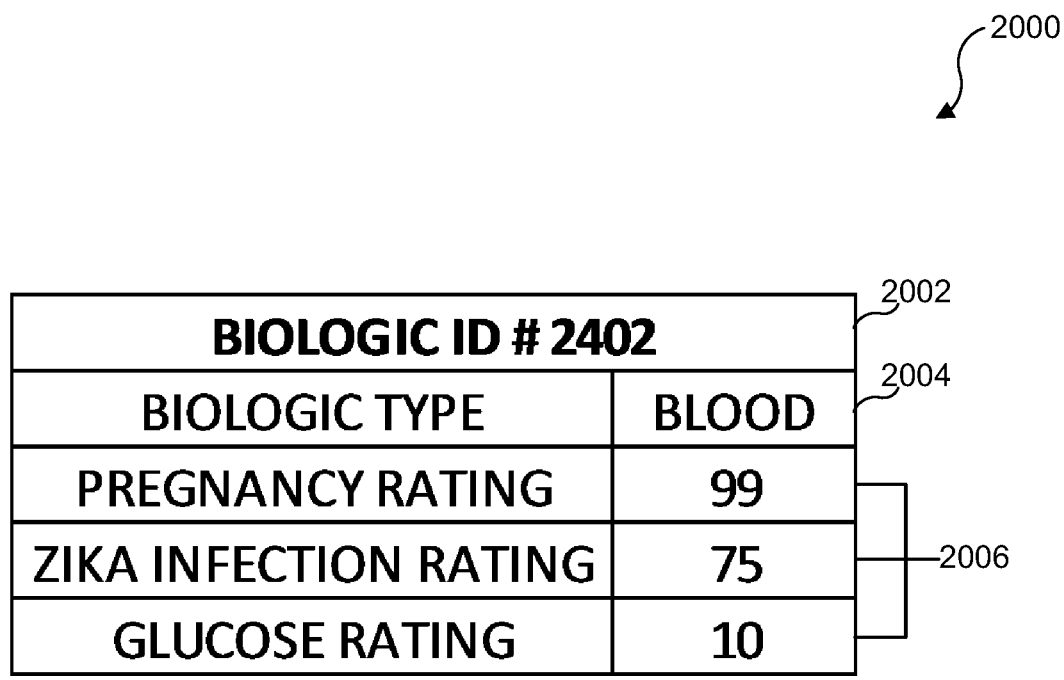
FIG. 20 illustrates an example of a unique biologic ID database table.

Referring now to FIG. 20, there is illustrated an example of a unique biologic ID database table 2000. The table 2000 is illustrative of the type of data stored in association with data for a biologic transmitted by a mobile device 102 for storage on the database 118. A biologic ID header 2002 is provided that shows that the biologic sample has been given a unique ID. All data concerning the biologic may be stored in association with the unique biologic ID. The table 2000 also includes a biologic type entry 2004. This designates what type of biologic that the biologic associated with the unique ID is, such as blood, urine, stool, saliva, sweat, or other biologics. The table 2000 also provides a plurality of test ratings 2006, for various tests performed on the biologic. In the example shown in FIG. 20, a blood biologic is provided having an assigned ID of 2402, and having been testing for pregnancy markers, the Zika virus, and for glucose levels. The rating for pregnancy was a 99 rating, the rating for a Zika infection was a 75, and the rating for glucose levels was a 10. This would indicate that the test subject has an extremely high likelihood of both a pregnancy and a Zika infection, which would have resulted in a warning to seek medical attention at the conclusion of the tests. Other information may also be stored in the database in relation to the biologic, including other condition ratings, time and date each test was performed, user information such as ethnicity, gender, and age, and status indicators such as whether a test subject visited a physician as a result of the tests. The database 118 thus provides the test subject with a growing collection of information that may be accessed by the test subject. This allows the test subject to present the test results to her physician for medical attention or additional testing, and allows for others who may access the database, such as disease researchers, to have access to data on various biologic samples and their markers.

Figure 21:
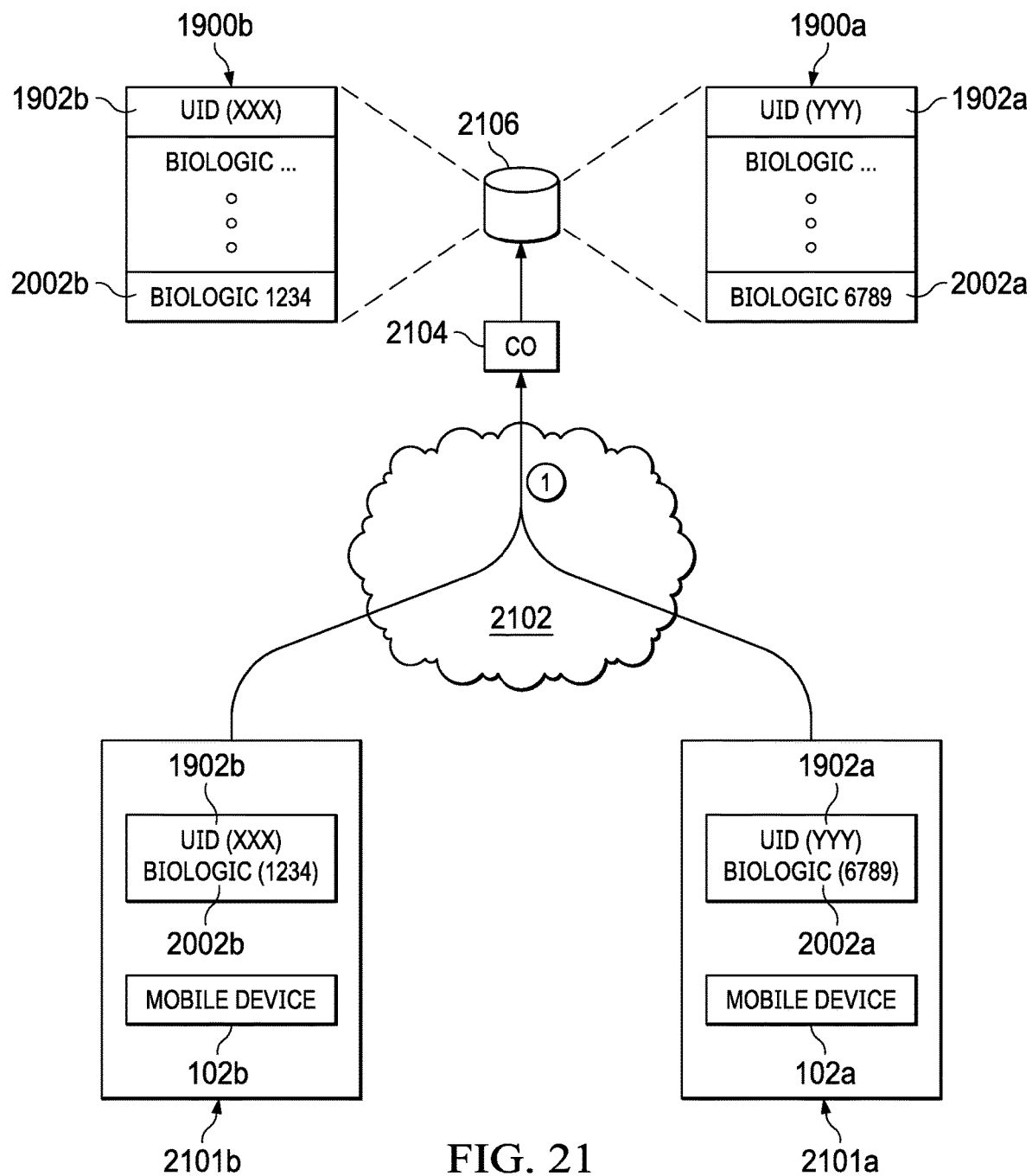
FIG. 21 illustrates an embodiment which includes mapping diagnostic tests to individual users to create unique profiles.

Referring next to FIG. 21, there is illustrated an embodiment which includes mapping diagnostic tests to individual users to create unique profiles. The patient/user 2101 conducts a medical test using a mobile device 102. The first time the patient 2101 uses the mobile application on the mobile device 102, the application allows the patient to create a unique ID 1902 to be assigned to the unique profile record 1900 associated with the patient. In some embodiments, the unique ID 1902 is simply assigned by the mobile application instead of being chosen by the user 2101. After a test is conducted, the mobile application transmits the biologic ID 2002 of the biologic tested along with the unique ID 1902 along Path ☐ through a network 2102, such as the internet, to a remote server or central office 2104. Once the biologic ID 2002 and the associated unique ID 1902 reaches the central office server 2104, the central office server transmits the biologic ID and the unique ID to a connected database 2106. Within database 2106 are stored the unique profile records 1900 for each patient/user 2101. Once the database 2106 receives the biologic ID 2002 and the unique ID 1902, the database uses the unique ID to identify the correct unique profile record 1900 and then appends the biologic ID 2002 to that unique profile record. If this is the first test conducted for/by a particular patient/user 2101, then the database 2106 creates a new unique profile record 1900 with the provided unique ID 1902 and appends the biologic ID 2002. In this way, each time a user 2101 conducts a diagnostic test, the unique ID 1902 and the biologic ID 2002 are sent to the database 2106, where the unique profile record is incrementally augmented with additional information about the user/patient 2101. In some embodiments, the biologic ID 2002 is not assigned by the application on the mobile device 102. Instead, the mobile device sends the information relating to the biologic (test type, test results, etc.) to the central office serve 2104 and database 2106, which then assign a biologic ID 2002 to the biologic data and associate it with the appropriate unique ID 1902.

Data for other users 2101 with other unique profiles 1902 will be handled similarly. Since each user 2101 has a unique profile record 1900 associated with him or her, the database 2106 will be able to associated biologic IDs 2002 with the correct user. In this way, the database 2106 will be populated with unique profile records 1900, from which potentially vast amounts of data can be obtained.

Figure 22:
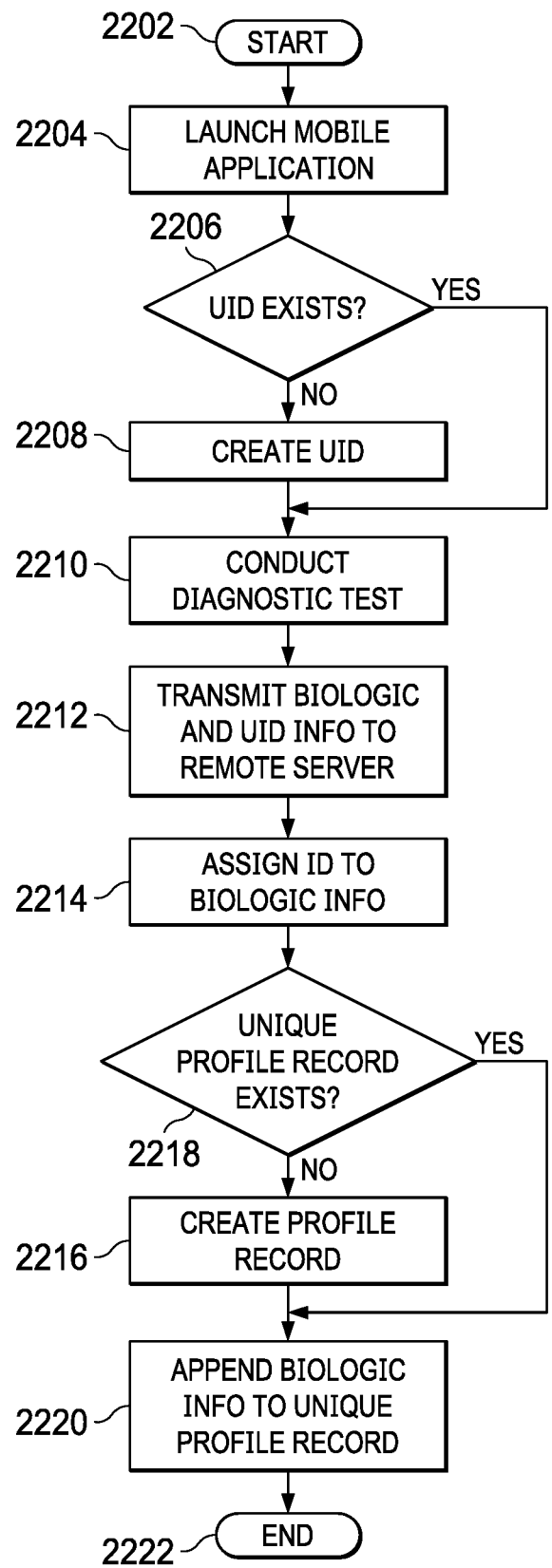
FIG. 22 illustrates a flowchart for an embodiment which includes mapping a diagnostic test to an individual user to create a unique profile on a remote database.

Referring now to FIG. 22, there is illustrated a flowchart for an embodiment which includes mapping a diagnostic test to an individual user to create a unique profile on a remote database. The process starts at Start block 2202 and proceeds to function block 2204, where the user launches the mobile application on the mobile device 102. The process then moves to decision block 2206. If a unique ID 1902 for the user does not exist, the process moves to function block 2208, where a unique ID is created by the mobile application. The process then moves to function block 2210. If, at block 2206, a unique ID 1902 for the user does exist, the process skips block 2208 and moves to function block 2210. At block 2210, the user conducts a diagnostic test with a testing device 300 and a mobile device 102 as described herein. The process then moves to block 2212, where the mobile application transmits the biologic ID information 2002 (which will also link the user to data about the type of diagnostic test) and the unique ID 1902 to the remote server 2104. At step 2214, an ID is assigned to the biologic information. The process then moves to decision block 2218. If a unique profile record 1900 for the user does not exist, the process moves to function block 2216, where a unique profile record is created. The process then moves to function block 2220. If, at decision block 2218, a unique profile record 1900 for the user already exists, the process moves to block 2220. At block 2220, the database 2106 appends the biologic ID information 2002 to the unique profile record 1900. The diagnostic test performed by the user is now mapped to the user's profile 1900 through the biologic database ID table 2000. The process then ends at End block 2222.

In some embodiments, a medical test may be performed by a doctor, lab technician, etc. and may use an automated testing device to perform the test. In this scenario, the test may be used to determine a treatment regimen for a patient based on the test results. For instance, if the test is designed to determine the proper medication and dosage level of that medication to effectively treat a patient, this information may be added to a patient file and transmitted to other parties to alert the other parties to take action in order to enact the treatment plan.

Figure 23:
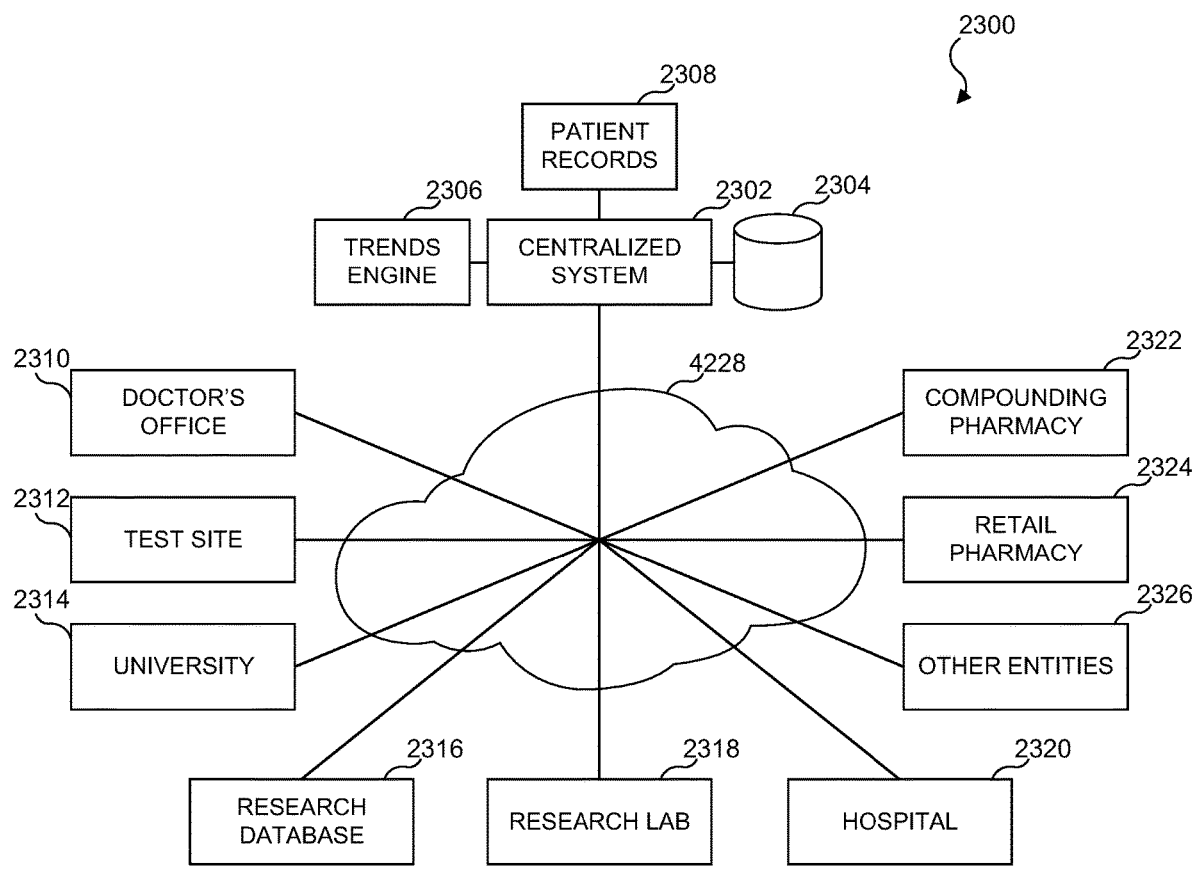
FIG. 23 illustrates a diagrammatic view of a medical test results, trends, and response system in accordance with various embodiments of the present disclosure.

FIG. 23 illustrates a diagrammatic view of a medical test results, trends, and response system 2300. The system 2300 includes a centralized system 2302. The centralized system 2302 may include or be connected to an actionable analytics database 2304, a trends engine 2306, and a plurality of patient records 2308. The plurality of patient records 2308 may include patient demographics and personal information, medical history including test results, doctor's notes, etc., medical information specific to the patient such as DNA data, blood type, markers detected during tests on the patient, or other types of information. The centralized system 2302 may act as a central hub of information for various entities related to the medical industry. These various entities may be interconnected with each other as well as with the centralized system 2302.

For example, the system 2300 illustrated in FIG. 23 further includes one or more of the following: a doctor's office 2310, a test site 2312, a university of higher learning 2314, a research database 2316, a research lab 2318, a hospital 2320, a compounding pharmacy 2322, a retail pharmacy 2324, the centralized system 2302, and other entities 2326. All these entities may be interconnected over a network 2328 to share information and otherwise provide an infrastructure for tracking medical test results, disease trends, pharmaceutical effectiveness trends, triggering medical actions for patients, etc. For example, test results generated by using the testing device described herein may include drug efficacy and proper dosage information pertaining to a patient. This information may be passed from the entity in the system 2300 that performed the test, such as a doctor's office 2310, a hospital 2320, a research lab 2318, or any other test site 2312 or other entity 2326. The results may then be received by the centralized system 2302 to update a patient record 2308 stored in associated with the centralized system 2302. The test results, test information, patient information, and other data may be stored in the database 2304 or processed by the trends engine 2306 to evaluate overall patient health, and to determine whether the patient is susceptible to other medical conditions or whether the test results received regarding the patient are indicative of trends or other medical conditions concerning other patients whose information is stored in the centralized system 2302. The results may also be utilized in advancing medical research, such as by universities 2314, research labs 2318, and by updating research databases 2316.

Referring now to FIG. 24, and still to FIG. 23, patient records on file with any of the entities 2310-2326 may also be updated to reflect the new information obtained as a result of the test. FIG. 24 illustrates the types of information that may be recorded in a patient record 2308, or in the database 2304, in accordance with various embodiments of the present disclosure. FIG. 24 shows that a patient may have a patient record 2402. This patient record may be stored as a document on the centralized system 2302, such as a text file, PDF file, excel file, or other document, or the data in the patient record 2402 may be stored in the database 2304. Particular test types may have ID numbers associated with the particular test types. The ID for the test type may be stored in relation to a patient record when the test associated with the test ID is performed on the patient associated with the patient record. Results of the test performed on the patient or on a patient's biologic specimen may also be stored in relation to the patient.

For example, FIG. 24 shows that test results 2404 of a test having a test ID of 10 are stored in relation to a patient having a patient ID of 1002. Test information results, treatment plans, and other information may be stored in relation to the patient. For example, and as illustrated in FIG. 24, if a patient is found to be positive for a bacterial infection, such as streptococcal bacteria, and results from a test conducted using the testing device described herein indicate that the most effective medication and dosage to treat the infection is amoxicillin at 250 mg, this information may be transmitted across the system 2300. The centralized system 2302 may receive the test results and generate a treatment plan or regimen that indicates that the patient should take amoxicillin at 250 mg twice daily for two weeks. The treatment regimen may be generated for the patient and this treatment regimen may be transmitted to entities responsible for enacting the treatment regimen, such as the doctor's office 2310, the compounding pharmacy 2322 or the retail pharmacy 2324, etc.

Figure 25:
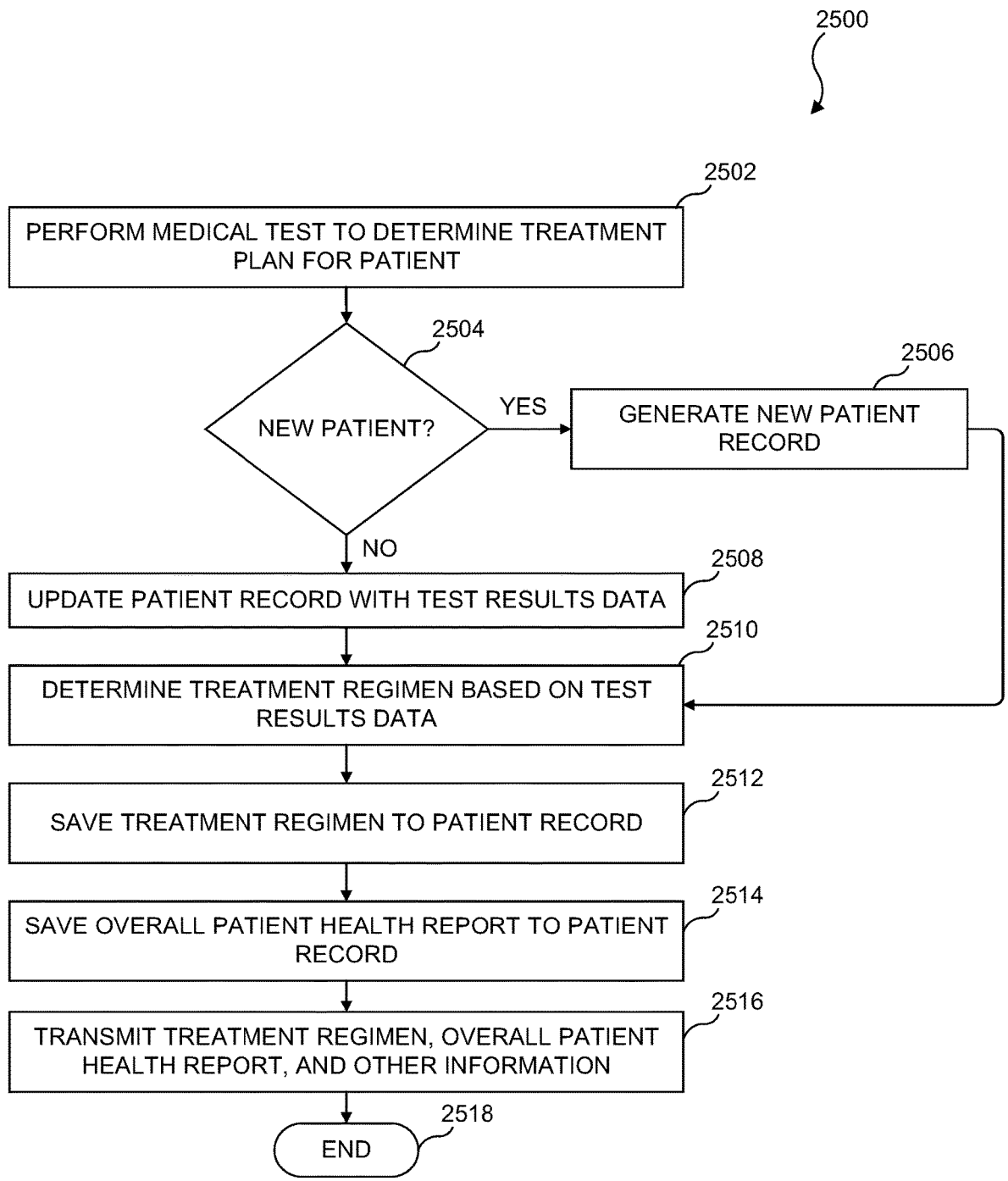
FIG. 25 illustrates a flowchart of a patient record update/creation process in accordance with various embodiments of the present disclosure.

Referring now to FIG. 25, there is illustrated a flowchart of a patient record update/creation process 2500. The process begins at step 2502 when a medical test is performed to determine a treatment plan for a patient, such as a test using a testing device. At decision block 2504, an entity such as the centralized system 2302 determines whether the patient is a new patient, which may be done by querying the database 2304 for personal information relating to the patient to determine if that information already exists in the database such as a social security number. If it is determined that the patient is a new patient, the process flows to step 2506 to generate a new record for the patient. The process then flows to step 2510. If at decision block 2504 it is determined that the patient already has a patient record stored, the process flows to step 2508 where the existing patient record is updated with the results of the test performed in step 2502. The process then flows to step 2510. At step 2510, a treatment regimen is determined for the patient based on the test results data. For instance, if a particular medication at a particular dosage level was tested as effective against a medical condition of the patient, a regimen of administration of the medication may be generated.

The process then flows to step 2512 to save the treatment regimen to the patient record. At step 2514, an overall patient health report may be saved to the patient record. This health report may include general information relating to the patient from other office visits, such as weight, medical states such as diabetes or other states, and may include the medical condition with respect to the test conducted in step 2502, such as stating the test date, severity of the condition, details regarding the treatment regimen and drug interactions and side effects, etc. The process then flows to step 2516. At step 2516, the treatment regimen, overall health report, and other patient information may be transmitted to entities that may use such information to treat the patient, such as a doctor's office, hospital, or other entity.

Figure 26:
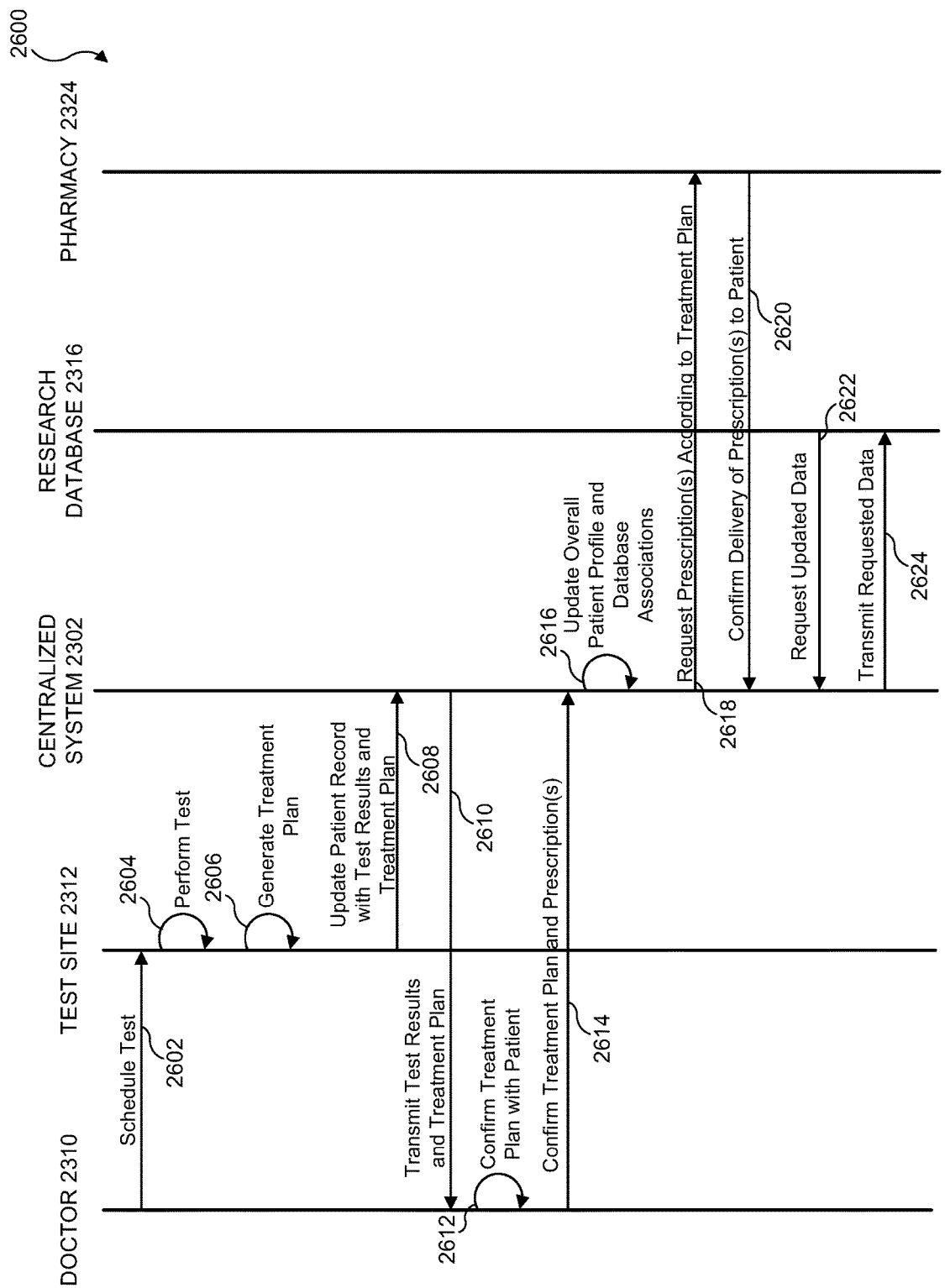
FIG. 26 illustrates a sequence diagram of a test results and treatment regimen enactment process.

Referring now to FIG. 26, there is illustrated a sequence diagram of a test results and treatment regimen enactment process 2600. At step 2602, a doctor sends a request to a test site to schedule a test. The test site at step 2604 then performs the scheduled test. At step 2606, a treatment plan is generated at the test site. The test site may generate the treatment plan when generation of the treatment plan is automated by the device performing the test, or by a professional analyzing the test. In some embodiments, the test results may be sent elsewhere for determining the treatment plan, such as to the doctor or to the centralized system.

At step 2608, the test site sends an update to the patient record at the centralized system with test results and a treatment plan. At step 2610, the centralized system transmits the test results and treatment plan to the doctor's office. At step 2612, the doctor's office confirms the treatment plan with the patient and at step 2614 the doctor's office sends a confirmation of the treatment plan and any written prescriptions to the centralized system. At step 2616, the centralized system updates the overall patient profile and database associations to that patient profile. For example, if the patient is a Caucasian female, and the test results were positive for Crohn's disease, such an association may be made in the database as a potential trend or susceptibility, but may wait for additional data before marking it as an active trend.

At step 2618, the centralized system requests one or more prescriptions from a pharmacy according to the treatment plan. At step 2620, the pharmacy transmits a confirmation to the centralized system that the prescriptions were delivered to or pickup by the patient. At step 2622, a research database may request updated data from the centralized system. The research database may utilize the centralized system as a storehouse for a multitude of information and data points related to diseases, patient demographics, biological markers, or other information useful to medical research and academia. At step 2624, the centralized system transmits the requested data to the research database.

Figure 27:
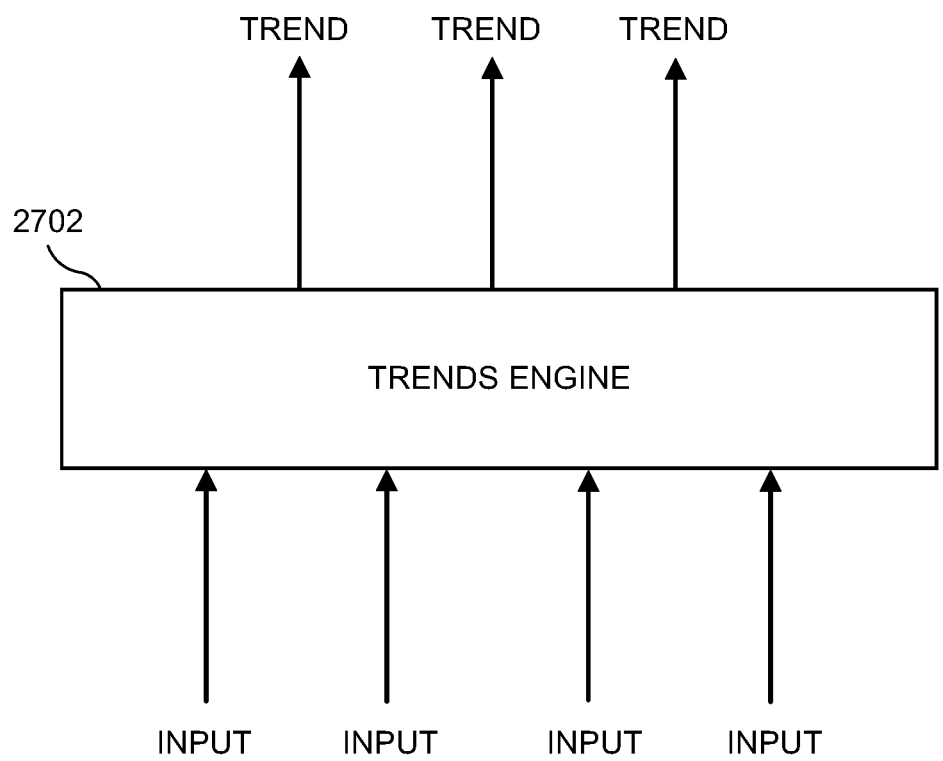
FIG. 27 illustrates a diagrammatic view of a trends engine in accordance with various embodiments of the present disclosure.

Referring now to FIG. 27, there is illustrated a diagrammatic view of a trends engine 2702 in accordance with various embodiments of the present disclosure. The trends engine 2702 may be a linear or non-linear deep learning neural network or trained database. Neural networks are non-parametric methods used for machine learning such as pattern recognition and optimization. They are able to generate an output based on a weighted sum of inputs, which is then passed through an activation function. Typically, the activation function determines the output by summing the inputs multiplied by the weights. A basic activation function is that of $y=f(\Sigma wx)$, where x is the vector of inputs, w is the vector of weights, f(.) is the activation function, and y is the output vector.

The inputs, weights, and outputs may be organized within a multilayer perceptron (MLP), wherein there is an input layer, one or more hidden layers, and an output layer. As shown in FIG. 27, a plurality of inputs may be entered into the trends engine 2702. The trends engine 2702 may include a series of weighted neurons that pass the inputs through an activation function t generate one or more outputs, or trends. The trends engine 2702 may be a feedforward network. Although there could be any number of hidden layers, typically ranging from one to three, it will be appreciated by those skilled in the art that a single hidden layer can estimate differentiable functions, provided there are enough hidden units. A higher number of hidden layers also increases processing time and the amount of adjustments needed during neural network training.

It will be understood by those skilled in the art that the neural network would be trained in order for the neural network to become more accurate. Various training methods exist, such as supervised learning where random weights are fed into the neural network and adjusted accordingly, back-propagation methods, or other methods. Activation functions are applied to the weighted sum of the inputs to generate a certain outcome. The weights may be set to small random values initially. The input pattern may then be applied and propagated through the network until a certain output is generated for the hidden layer. Training results may be collected including the number of true positives, true negatives, false positives, and false negatives. If the number or percentage of false positives and negatives appear too high, additional training may be required.

The outputs of the hidden layer are used as entries for the output layer. Weighted and summed up, they are passed through an activation function to produce the final output. The way the weights are modified to meet the desired results defines the training algorithm and is essentially an optimization problem. When the activation functions are differentiable, the error back-propagation algorithm may be a good approach in progressing towards the minimum of the error function. The errors are then passed back through the network using the gradient, by calculating the contribution of each hidden node and deriving the adjustments needed to generate an output that is closer to the target value. It will be understood by those skilled in the art that neural networks can be set up and trained in various ways and that the above description is illustrative of but one method. It will be appreciated that the neural network may be organized in any way to allow for the functionality disclosed herein.

In some embodiments, the trends engine 2702 may function on a threshold system. For instance, if a certain number or percentage of patients that are within a specific haplogroup also test positive for a specific medical condition, this may indicate a trend output by the trends engine 2702. As more positive results are received for a particular medical condition, the trends engine 2702 may query the database 2306 to determine if there are any demographical or other commonalties between patients that have tested positive for the medical condition. For example, if the threshold is set to 75%, and 80% of patients of African descent have tested positive for a medical condition, the trend engine 2702 may communicate the trend to other entities within the system 2300, or provide the trend when the centralized system 2302 is accessed by other entities in the system 2300.

Referring now to FIG. 28, there is illustrated one embodiment of database tables showing a particular trend. There is shown a patient record 2802. The patient record 2802 includes various data concerning the patient, such as the test IDs for tests performed on the patient or a specimen from the patient. If a patient has a DNA test performed, a patient's haplogroup may be determined. Haplogroups may be Y-chromosomal or may be mitochondrial haplogroups. The centralized system 2302 may keep track of a patients' haplogroups to attempt to find trends among patients that share a common ancestry. For example, FIG. 28 illustrates that patient ID #1002, in record 2802, is within haplogroup C. Thus, the centralized system 2302 may link the patient to data accumulated and test results obtained regarding all patients that are within haplogroup C. Table 2804 illustrates that the centralized system 2302 may count the number of positive results for each test performed on a person of haplogroup C. In this example, patient ID #1002 has may have tested positive for test ID 10. The table 2804 shows that a large number of people in haplogroup C have also tested positive for test ID #10. There is also shown in patient record 2802 that the patient is susceptible to prostate cancer. This may be determined from a trend similar to that shown in 2804. For instance, if test ID #10 tested for prostate cancer markers, and the 10,720 positive results illustrated in FIG. 28 was above a threshold amount to activate a trend, all patients in haplogroup C, such as patient ID #1002, would have an entry added to his or her patient record noting a trending susceptibility to prostate cancer.

Figure 29:
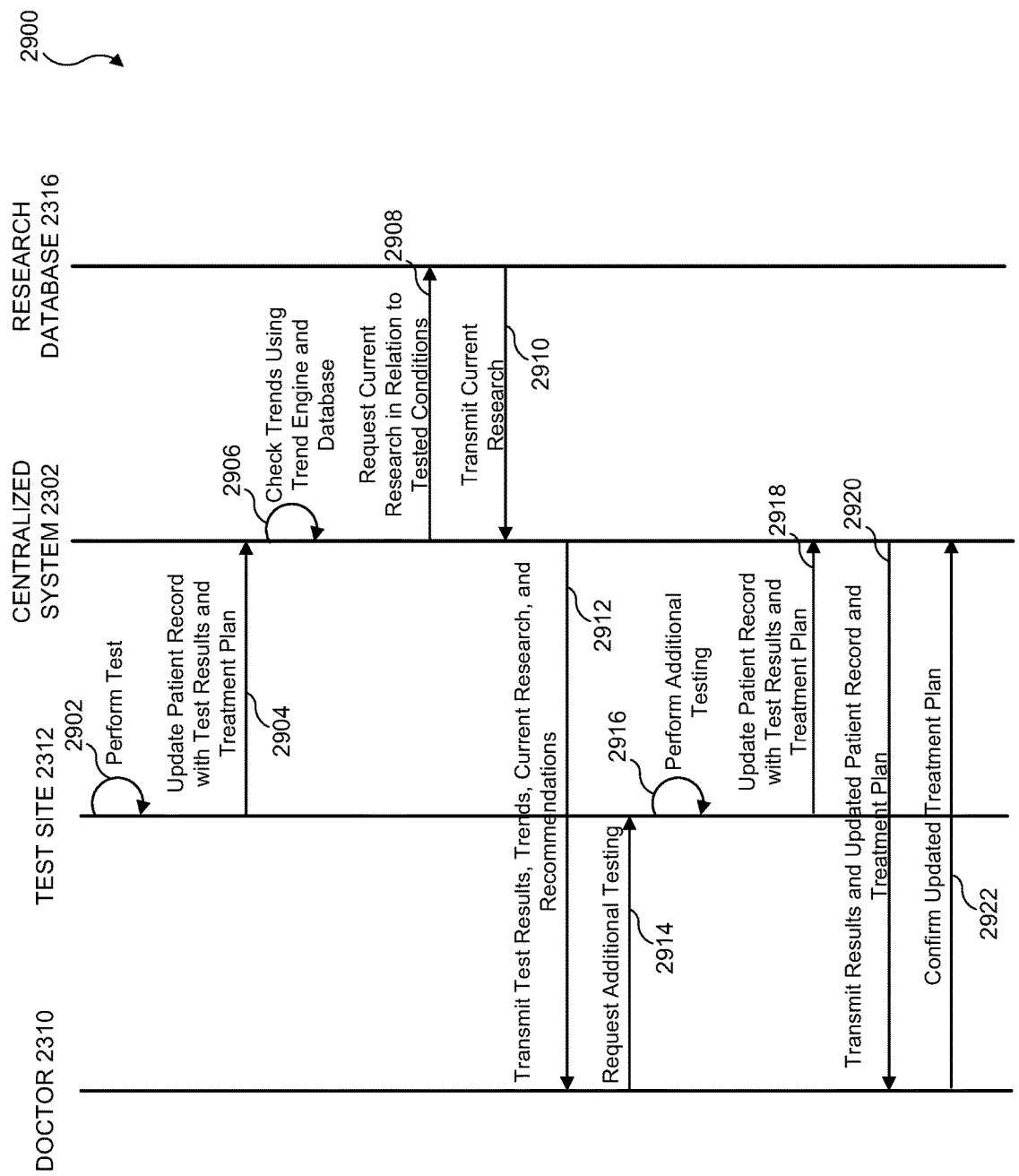
FIG. 29 illustrates a sequence diagram of a research and trends feedback process in accordance with various embodiments of the present disclosure.

Referring now to FIG. 29, there is illustrated a sequence diagram of a research and trends feedback process 2900. At step 2902, a test site 2312 performs a medical test, such as a test using testing device. At step 2904, the test site 2312 sends to the centralized system 2302 a patient record update including test results and a treatment plan. At step 2906, the centralized system 2302 checks trends via the trend engine 2306 and database 2304. At step 2908, the centralized system 2906 requests current research regarding the medical condition of the patient from a research database 2316. At step 2910, the requested research is transmitted from the research database 2316 to the centralized system 2302. At step 2912, the centralized system 2302 transmits the test results, any trends regarding the patient or others similar to the patient, the requested current research, and any recommendations based on this data to the doctor's office 2310. At step 2914, the doctor's office 2310 requests additional testing for the patient. The doctor may request additional testing because of trends regarding the patient's condition or research that was provided to the doctor in step 2912. At step 2916, the test site performs the additional testing.

At step 2918, the test site sends an update to the patient record including the test results for the additional testing and a new or updated treatment plan for the patient based on the additional testing. At step 2920, the test results are update patient record and treatment plan are transmitted from the centralized system 2302 to the doctor's office 2310. At step 2922, the doctor's office 2310 sends confirmation of the updated treatment plan to the centralized office 2922.

Figure 30:
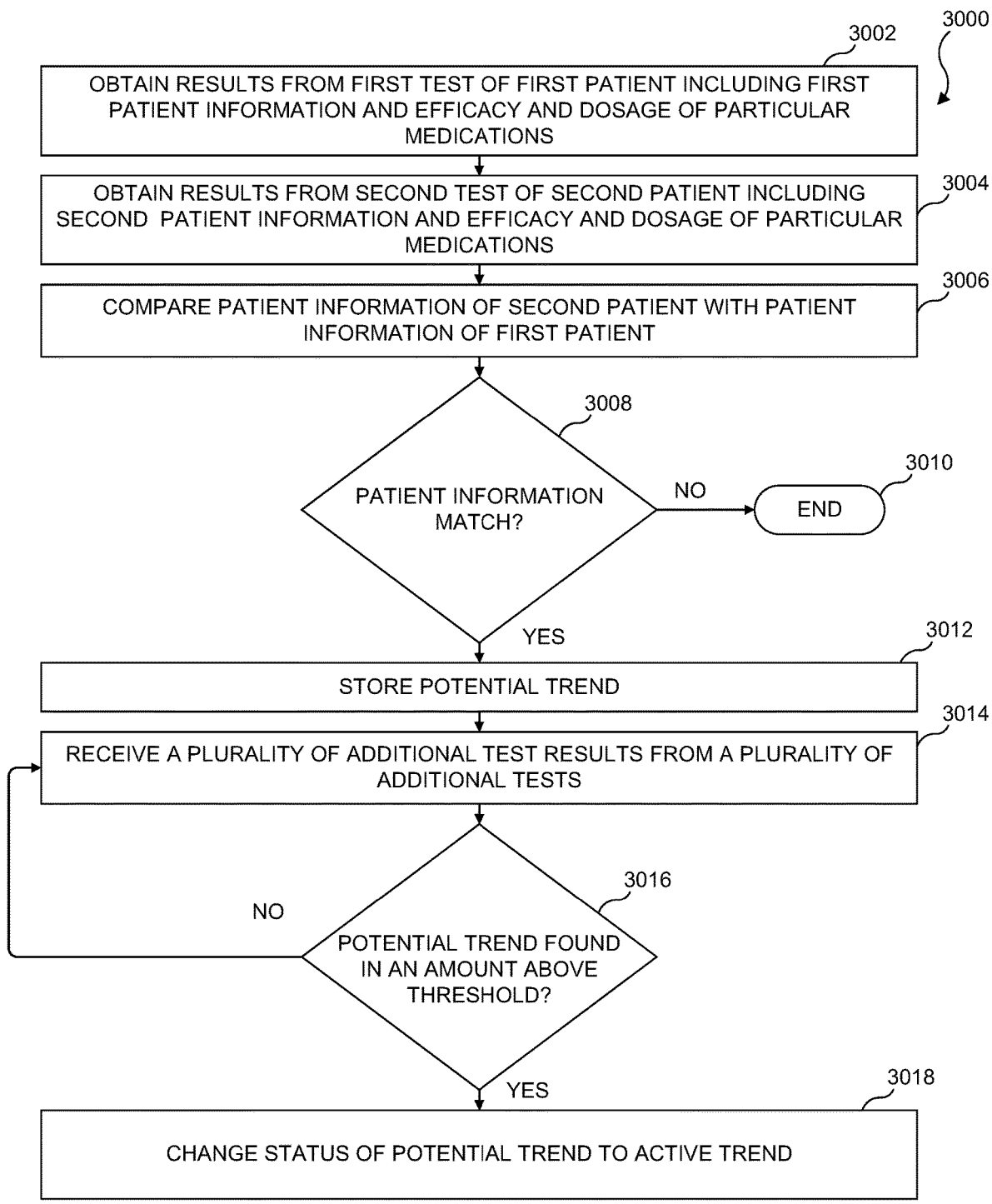
FIG. 30 illustrates a medical condition trend activation process in accordance with various embodiments of the present disclosure.

Referring now to FIG. 30, there is illustrated a medical condition trend activation process 3000. The process 3000 begins at step 3002, where patient information and the efficacy and dosage for particular medications pertaining to a first patient produced by a first test are obtained by an entity such as the centralized server. At step 3004, patient information and the efficacy and dosage for particular medications pertaining to a second patient produced by a second test are obtained by an entity such as the centralized server. At step 3006, the server compares patient information of the second patient with the patient information of the first patient. At decision block 3008, it is determined whether there is any significant patient information matches. For example, if the tests conducted on both patients were for Crohn's disease, and both patients are of the same gender and ethnicity, then there may be a significant patient information match. If there is no significant patient information match the process flows to end block 3010. If there is a match, the process flows to step 3012 to store the potential trend.

A trend may be stored as a potential trend when there is a correlating data point, but not enough data to activate it as an active trend in the system. At step 3014, the system receives a plurality of additional test results from a plurality of addition conducted tests. The process then flows to decision block 3016 to determine whether additional instances of the potential trend stored in step 3012 is in an amount above a threshold. Such a threshold may be a certain number, a percentage of all patients related to the trend demographic or other data point (such as all female patients of a particular ethnicity), or other threshold types. If instance of the potential trend is not above the threshold, the process flows back to step 3014 to receive more test results. If at decision block 3016 it is determined that the instances of the potential trend is above the threshold, the process flows to step 3018. At step 3018, the system changes the status of the potential trend to an active trend.

Independent prescribing, or prescriptive authority, is the ability of doctors, telemedicine doctors, and advanced practice registered nurses (APRNs) to prescribe, without limitation, legend (prescription) and controlled drugs, devices, adjunct health/medical services, durable medical goods, and other equipment and supplies. An issue with some telemedicine procedures is that telemedicine healthcare professionals, that is, doctors and other personnel that participate in and provide telemedicine services to patients may be reluctant to write a prescription for a medication for a patient. This is because confirmation of patient identity and confirmation of actual patient symptoms and diagnosis is limited when the telemedicine healthcare professionals typically only have a brief communication, such as a video conference, with the patient. The telemedicine healthcare professional may be concerned that the patient is faking symptoms to get medications, may be concerned that the telemedicine healthcare professional may improperly diagnose the patient and provide medication that could harm the patient, or may fear liability due to an improper medication being prescribed. The system and methods disclosed herein allow for a telemedicine healthcare professional to receive a quantifiable and verified test report on a patient that ensures the telemedicine healthcare professional in using his or her prescriptive authority during a telemedicine session.

A person's unique ID created from taking a medical test as described herein may also be paired with patient/user authentication data such as a login authentication via an application on a mobile device, biometric confirmation, etc. When the telemedicine doctor receives this information, the doctor can see that a certified test result was created due to the administration of the medical test such as those described herein and patient identity confirmation information, the telemedicine doctor can have a greater assurance that the patient does indeed have a particular medical condition and of the patient's identity.

Figure 31:
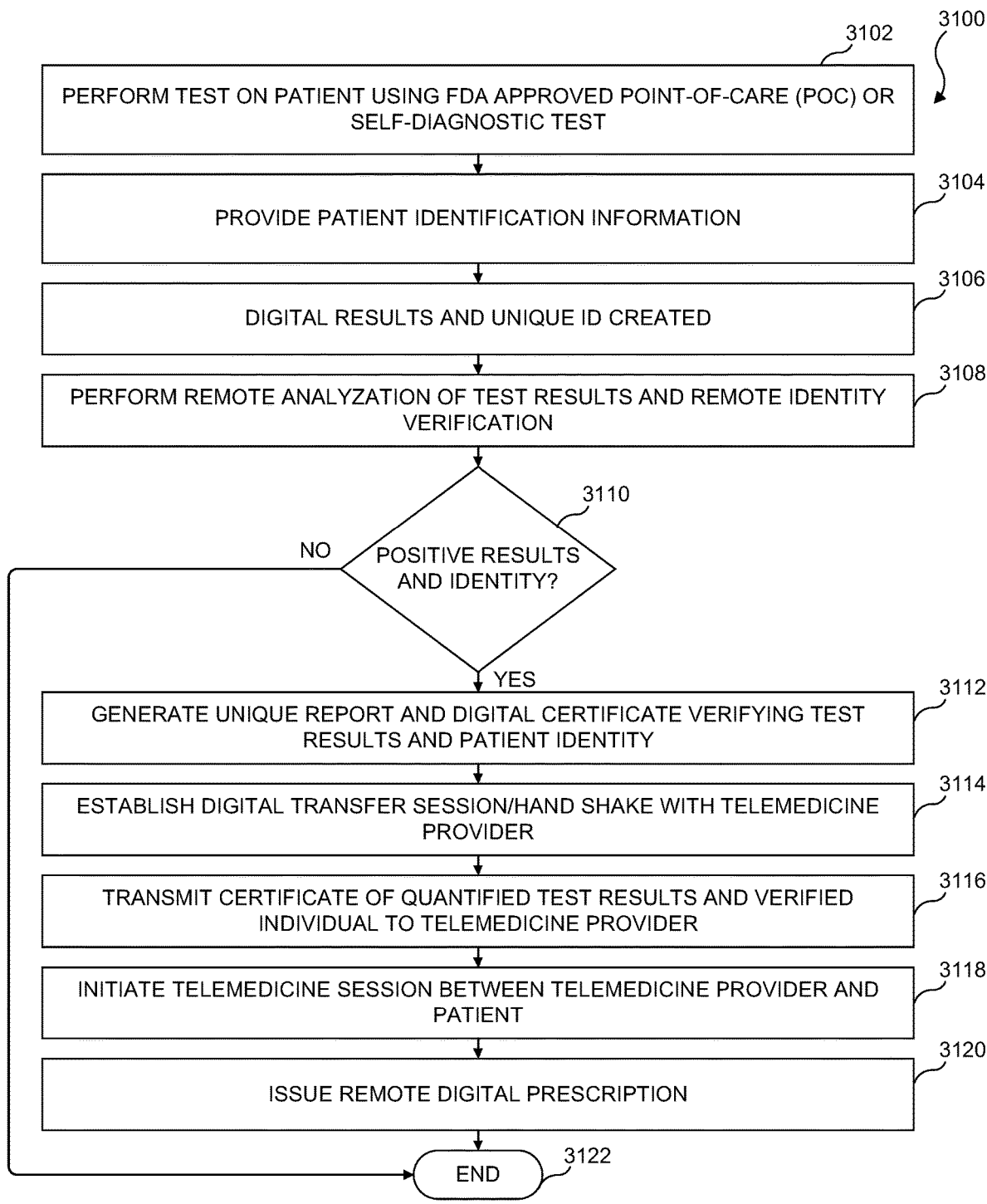
FIG. 31 illustrates a flowchart of one embodiment of a digital certificate of quantified test results and verified individual hand shake process.

Referring now to FIG. 31, there is illustrated a flowchart of one embodiment of a digital certificate of quantified test results and verified individual hand shake process 3100. The process 3100 begins at step 3102. At step 3102, a test is performed on a patient. The test may be an FDA approved test administered by a point-of-care (POC) site, or may be an FDA approved self-diagnostic test administered by the patient. At step 3104, patient identification information is provided. Identification information may include login information if the test uses an application, such as an application on a mobile device for remote test results capture, personal information such as date of birth, social security, or other personal information, or biometric information such as a patient fingerprint scan. A verification process may also be conducted on the test being administered. For example, in some embodiments a mobile device may scan a unique code on the testing device, such as the test type identifier 206 described herein, to confirm that the test device being used is an FDA approved test device and appropriate for the medical condition being tested.

At step 3106, digitized test results and a unique ID are created, which may be created as described herein to generate the unique identifier 212. At step 3108, the digital test results and unique ID are analyzed and the identification information is verified by a remote device such as the server 116 or the centralized system 2302. At decision block 3110, it is determined whether the test results analyzation and identity verification processes confirm a positive medical condition test result and confirm the identity of the patient. The identity of the patient may be confirmed based on information previously provided by the patient and stored at the remote device, such as if the patient previously provided a biometric fingerprint scan and has provided a new scan as part of the patient identification information in step 3104. If either the test results are negative or the patient's identity cannot be confirmed, the process ends at end block 3122.

If at decision block 3110, the test results are positive and the patient's identity is confirmed, the process flows to step 3112. At step 3112, a unique report including a digital certificate verifying test results is generated by the remote device. The digital certificate may be a created by the remote device to provide confirmation and assurance of the medical test results and patient identity to a telemedicine provider. Since test results and identity information are analyzed by the remote device against a learned system and database as described herein, accurate results can be achieved to provide confidence in the report and digital certificate. The digital certificate may include information such as the quantified test results provided by the server and confirmation of the patient's identity. The digital certificate may also include the unique identifier 212, which provides a plurality of information pertaining to the patient, biologic samples taken from the patient, and other information as described herein. The digital certificate thus provides a telemedicine doctor with assurance of an accurate diagnosis of the patient's medical condition(s) and of the patient's identity. In some embodiments, the report and/or certificate may be encrypted with a public key and later decrypted by a telemedicine provider with a private key, or in some embodiments other encryption paradigms may be implemented.

At step 3114, a digital transfer session or hand shake is established between the remote device and a telemedicine provider is established. At step 3116, the remote device transmits the report and digital certificate to the telemedicine provider. In some embodiments, the remote device may also provide additional information to the telemedicine provider, which may be included in the report in some embodiments, generated by the remote device (such as the centralized system 2302 and trends engine 2306 described herein). This additional information may be information such as current trends, new research data related to the medical condition found in the patient, treatment regimens, or other information that may be useful to the telemedicine provider or doctor during a telemedicine session with the patient. At step 3118, a telemedicine session is initiated between the telemedicine provider and the patient. During the telemedicine session, the telemedicine doctor may ask the patient questions to get a better understanding of the state of the patient, and to verify the details in the report. The doctor may also perform a visual inspection of the patient via video conference. At step 3120, the telemedicine doctor may exercise his or her prescriptive authority to write a prescription for the patient and issue a remote digital prescription to pharmacy for patient pickup or delivery. The process then ends at step 3122.

Figure 32:
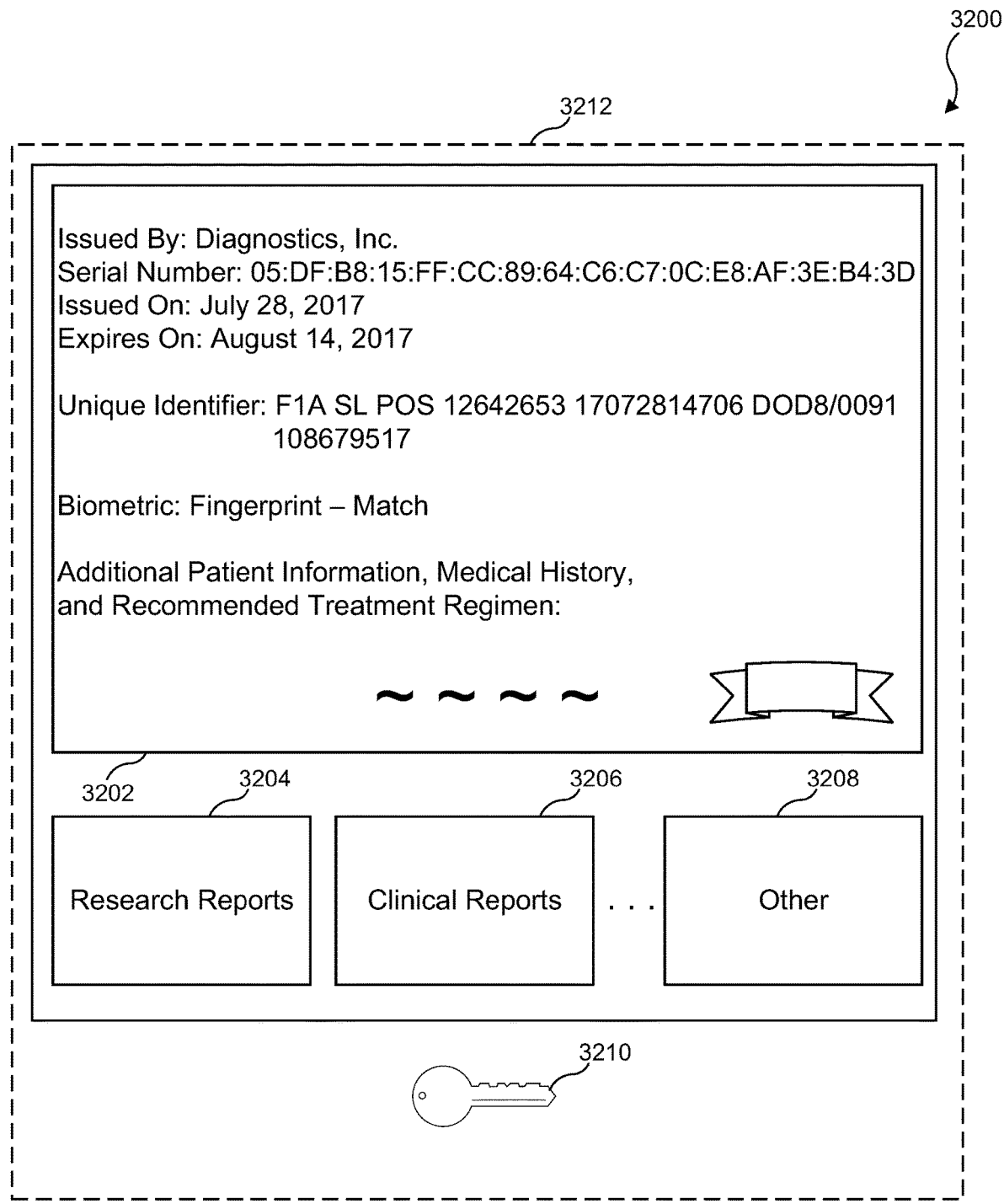
FIG. 32 illustrates one example of a medical test results digital certificate package.

Referring now to FIG. 32, there is illustrated one example of a medical test results digital certificate package 3200. The package 3200 includes a digital certificate 3202. The digital certificate 3202 includes a plurality of information such as the entity that issued the certificate. This entity may be an entity that performed the test on the patient, or may be the entity that owns or manages the centralized system 2302. The digital certificate 3202 may also include a serial number for the particular digital certificate, an issue date of the certificate, an expiration date on which the validity of the certificate expires, the patient's unique identifier, patient biometric verification type and results, and other information including patient personal information, medical history, a recommended treatment regimen, or other information.

In addition to the digital certificate 3202, other reports, data, or information may be sent to a telemedicine doctor, where these other reports, data, and information may be helpful to the telemedicine doctor in treating and advising the patient. The example shown in FIG. 32 includes research reports 3204, which may have been retrieved by the centralized system 2302 from a research database 2316 in response to positive test results for the patient, clinical reports 3206, and other reports or information 3208. The digital certificate package 3200 may then be encrypted using a public encryption key 3210, and may only be decrypted using a private decryption key made available to partnered telemedicine providers. Encryption may be performed using triple DES, RSA, AES, or other algorithms, and transmission of the digital certificate package 3200 may also be encrypted using SSL/TLS or other methods. In some embodiments, a second level of encryption or a wrapper 3212 may be implemented to provide additional security during transmission.

Figure 33:
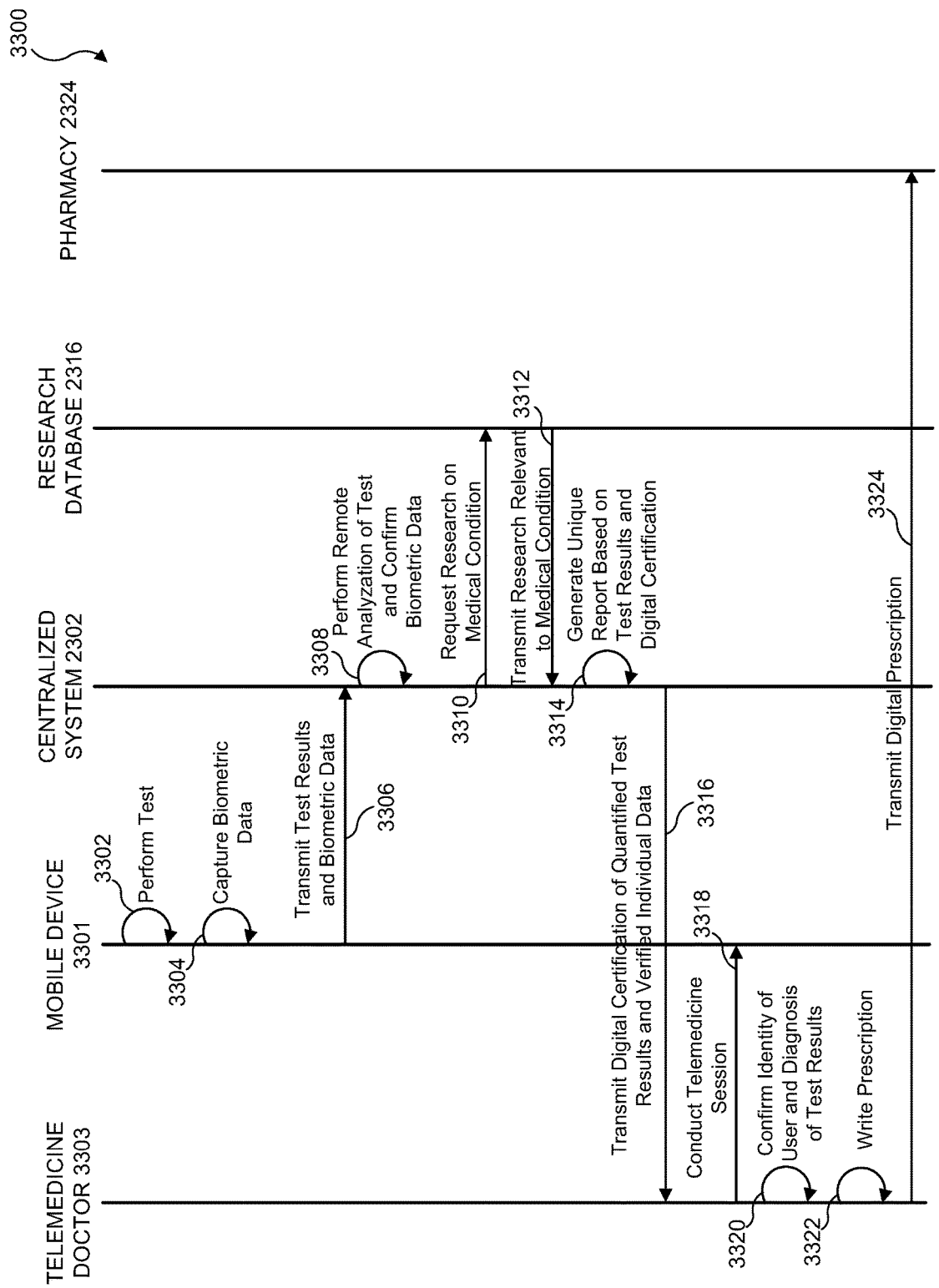
FIG. 33 illustrates a sequence diagram of one embodiment of a digital certificate of quantified test results and verified individual hand shake process.

Referring now to FIG. 33, there is illustrated a sequence diagram of one embodiment of a digital certificate of quantified test results and verified individual hand shake process 3300. At step 3302, a test is performed on a user/patient, which the test may include a mobile device 3301 that captures test results and performs other processing concerning the test. At step 3304, the mobile device 3301 captures biometric data from the patient, such as a fingerprint scan or other information. At step 3306, the mobile device 3301 transmits the test results and the biometric data to the centralized system 2302. It will be understood that the centralized system 2302 may be the server 116, or another system or device capable of processing the data. At step 3308, the centralized system 2302 performs remote analyzation of the test results, which may involve analyzing an image, video, or other media captured of the testing device or analog test results, and may also include comparing the test results against a database or trends engine that includes previous tests performed on the patient or other patients. The centralized system 2302 also confirms at step 3308 the biometric data to determine patient identity.

If the results of the analysis performed at step 3308 determines or confirms a positive test result for the medical condition that is the subject of the test, the centralized system 2302 may at step 3310 request medical research on the medical condition from a research database 2316. At step 3312, the research database 2316 transmits the requested research to the centralized system 2302. At step 3314, the centralized system 2302 generates a unique report and a digital certification of the test results and patient identity. The report may include a plurality of information such as patient personal information, patient medical history, test results from past and the current test performed on the patient and may include information on other patients that also tested positive for the medical condition, the research received from the research database 2316, and other information useful to a telemedicine doctor.

Also at step 3314, the centralized system 2302 generates a digital certification. The digital certification provides confirmation and assurance of the medical test results and patient identity to a telemedicine provider. Since test results and identity information are analyzed by the remote device against a learned system and database as described herein, accurate results can be achieved to provide confidence in the report and digital certificate. The digital certificate may include information such as the quantified test results provided by the server and confirmation of the patient's identity. The digital certificate may also include the unique identifier 212, which provides a plurality of information pertaining to the patient, biologic samples taken from the patient, and other information as described herein. The digital certificate thus provides a telemedicine doctor with assurance of an accurate diagnosis of the patient's medical condition(s) and of the patient's identity.

At step 3316, the centralized system 2302 transmits the digital certification and the unique report to a telemedicine doctor 3303. Since the report indicates that the patient tested positive for one or more medical conditions, the telemedicine doctor 3303 at step 3318 conducts a telemedicine session with the patient using the mobile device 3301. It will be understood that the patient may use a different device for the telemedicine session other than the mobile device 3301 used during performance of the test at steps 3302 and 3304. At step 3320, during the telemedicine session the telemedicine doctor 3303 confirms the identity of the patient and the diagnosis provided by the test results. Although the unique report and the digital certificate may provide an accurate and strong indication of the patient's identity and medical condition, the telemedicine doctor 3303 confirms what is in the repot and the certificate by performing a visual inspection of the identity of the patient, and of the symptoms experienced by the patient. The telemedicine doctor 3303 may also ask questions regarding the patient's identity and the symptoms experienced by the patient to form a complete assessment of the patient.

Once the telemedicine doctor 3303 is assured that the patient has one or more medical conditions, the telemedicine doctor 3303 may determine that a prescription medication is necessary for treating the patient. If so, at step 3322, the telemedicine doctor 3303 exercises his or her prescriptive authority and writes a prescription for the medication the telemedicine doctor 3303 believes will assist in treating the patient. At step 3324, the telemedicine doctor 3303 transmits a digital prescription to a pharmacy 2324 for pickup by, or deliver to, the patient.

Figure 34:
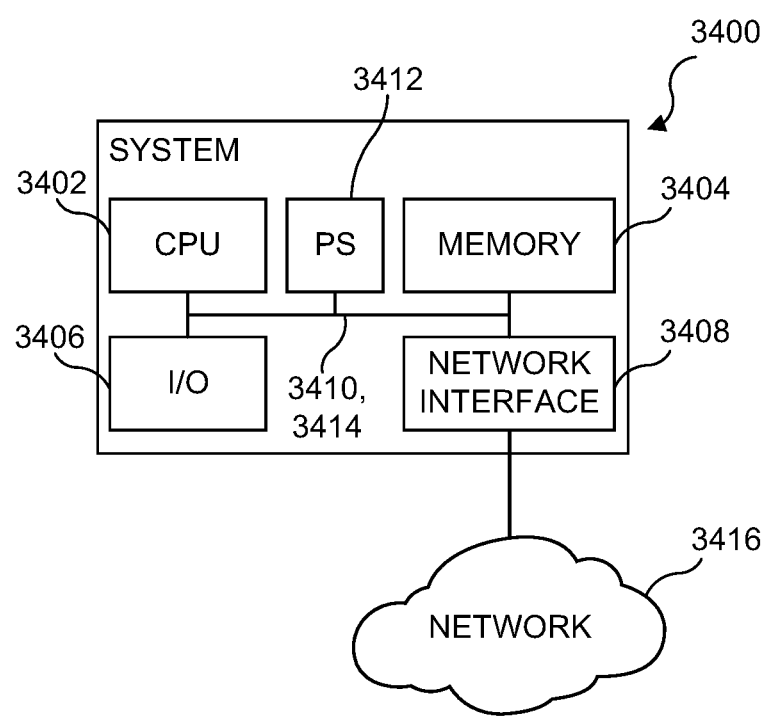
FIG. 34 illustrates a diagrammatic view of one embodiment of a system device that may be used within the environment described herein.

Referring to FIG. 34, one embodiment of a system device 3400 is illustrated. The system device 3400 is one possible example of a device used by an end user, and/or a device such as the mobile device 102 or the server 116. Embodiments include cellular telephones (including smart phones), personal digital assistants (PDAs), netbooks, tablets, laptops, desktops, workstations, telepresence consoles, and any other computing device that can communicate with another computing device using a wireless and/or wireline communication link. Such communications may be direct (e.g., via a peer-to-peer network, an ad hoc network, or using a direct connection), indirect, such as through a server or other proxy (e.g., in a client-server model), or may use a combination of direct and indirect communications. It is understood that the device may be implemented in many different ways and by many different types of systems, and may be customized as needed to operate within a particular environment.

The system 3400 may include a controller (e.g., a central processing unit ("CPU")) 3402, a memory unit 3404, an input/output ("I/O") device 3406, and a network interface 3408. The components 3402, 3404, 3406, and 3408 are interconnected by a transport system (e.g., a bus) 3410. A power supply (PS) 3412 may provide power to components of the computer system 3400, such as the CPU 3402 and memory unit 3404, via a power system 3414 (which is illustrated with the transport system 3410 but may be different). It is understood that the system 3400 may be differently configured and that each of the listed components may actually represent several different components. For example, the CPU 3402 may actually represent a multiprocessor or a distributed processing system; the memory unit 3404 may include different levels of cache memory, main memory, hard disks, and remote storage locations; the I/O device 3406 may include monitors, keyboards, and the like; and the network interface 3408 may include one or more network cards providing one or more wired and/or wireless connections to a network 3416. Therefore, a wide range of flexibility is anticipated in the configuration of the computer system 3400.

The system 3400 may use any operating system (or multiple operating systems), including various versions of operating systems provided by Microsoft (such as WINDOWS), Apple (such as Mac OS X), UNIX, and LINUX, and may include operating systems specifically developed for handheld devices, personal computers, servers, and embedded devices depending on the use of the system 3400. The operating system, as well as other instructions, may be stored in the memory unit 3404 and executed by the processor 3402. For example, the memory unit 3404 may include instructions for performing some or all of the methods described herein.

Figure 35A:
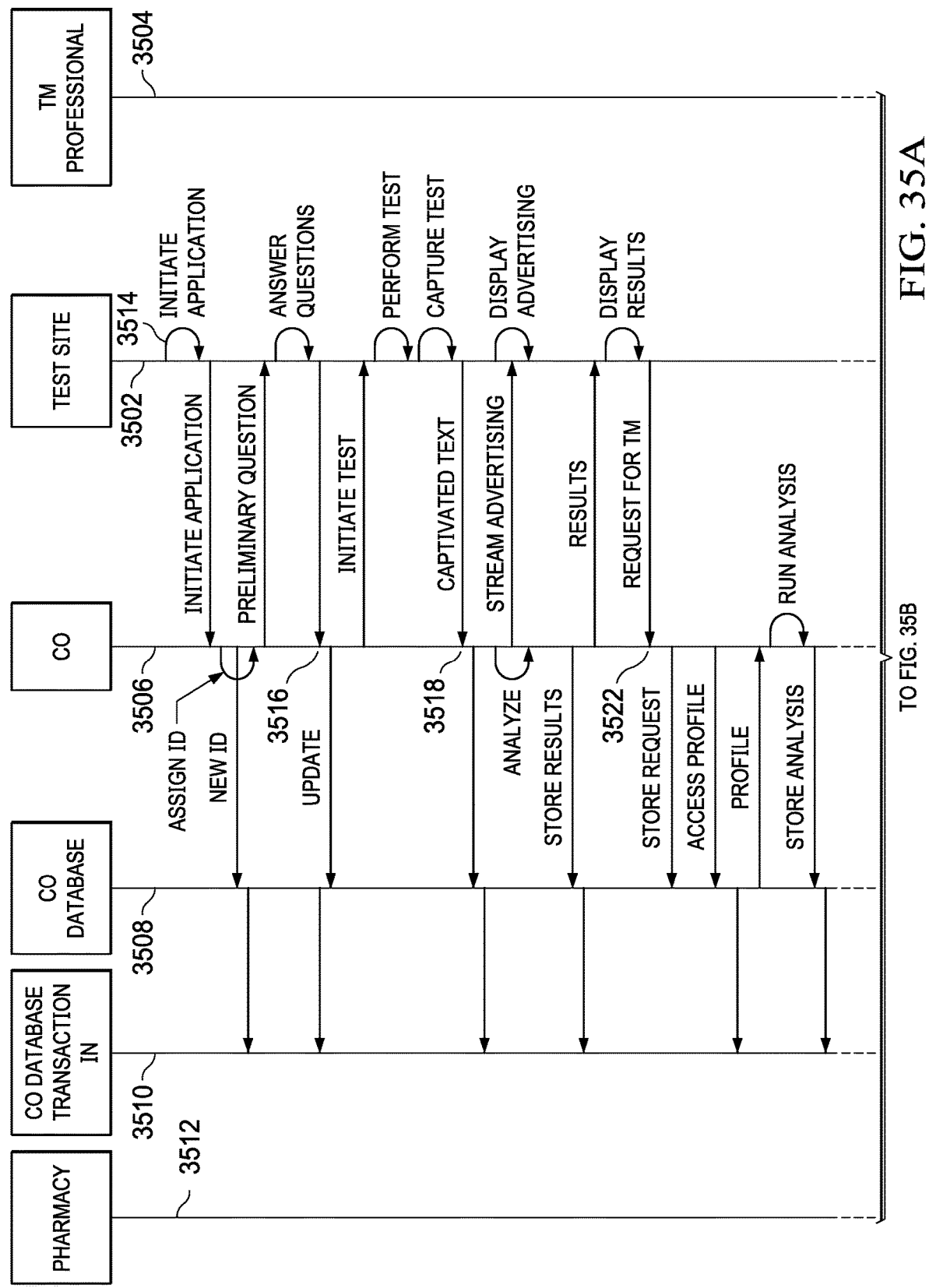

Referring now to FIGS. 35A and 35B, there is illustrated a sequence diagram for a specific telemedicine transaction starting from the initiation of the transaction to the completion of the transaction in the form of providing some type of treatment regimen to a patient, one form being a prescription to a patient and another form being possibly directing the patient to a medical professional or even to the emergency room. For the purpose of this specific example, a Urinary Tract Infection (UTI) will be the subject of the transaction. In this diagnostic transaction, the diagnostic transaction is directed toward a specific malady or medical condition or suspected malady or medical condition from the perspective of the patient, i.e., the patient in this example is he of the opinion that they have a UTI. This is to be compared to conventional medical diagnosis. In conventional medical diagnosis, a medical professional will go through a process of determining which disease or condition explains a person's symptoms and signs. The information required for diagnosis is typically collected from a history and physical examination of the person seeking medical care. Often, one or more diagnostic procedures, such as diagnostic tests, are also done during the process. In general, the medical professional will follow acceptable industry standards and procedures followed by the medical community for performing any type of diagnosis Diagnosis can often become challenging, due to the many signs and symptoms present that are nonspecific. For example, redness of the skin (erythema), by itself, is a sign of many disorders and thus does not tell the healthcare professional what is wrong. Thus differential diagnosis, in which several possible explanations are compared and contrasted, must be performed. This involves the correlation of various pieces of information followed by the recognition and differentiation of patterns.

By comparison, the current medical transaction is one that is geared toward some commonality such as UTI. The patient may have had this previously diagnosed and recognizes that the symptoms they are experiencing are consistent with a UTI. This may be because of their personal history or information they have obtained from the Internet or from a friend. In any event, this transaction to be described hereinbelow is for the purpose of confirming that they do in fact have a UTI or confirming that it is not a UTI. If confirmed, the end goal is to have this condition treated if possible via some acceptable therapeutic regimen such as antibiotics. This treatment usually results in either being referred to a specialist or merely receiving a prescription. This particular transaction, the UTI, is one that can typically be treated with an antibiotic. Thus, this is a very specific transaction which has a very specific goal in mind.

In general, when considering the transaction associated with determining if the patient has a UTI, a very specific sequence of decisions will be made. If one were to visit a healthcare professional, that healthcare professional would ask questions of the patient and make some assessment as to their overall health and medical history, which would lead them to a strong suspicion that it was a UTI. By performing some diagnostic test such as taking a culture, the presence of a UTI can be confirmed. Once confirmed, the general body of wisdom in the medical profession is to prescribe a particular antibiotic. The type of antibiotic can be determined based upon the results of the diagnostic test and also the history of the particular individual. For example, there are some antibiotics that are not recommended for patients who are diabetic, or example. Also, if a patient is susceptible to hypertension, this may also determine the type of antibiotic prescribed. This, of course, changes as new antibiotics come to market and other antibiotics are determined to be ineffective for a particular UTI or have been determined to have some unacceptable side effects. Thus, the body of wisdom does change over time and it is the responsibility of the medical professional to make decisions based upon this body of wisdom.

Referring back to FIGS. 35A and 35B, there is illustrated multiple decision loci at which certain portions of the decisions for the transaction are made. There is a test site 3502 at which the patient resides and the location at which various tests and information are retrieved from a patient and the location at which the patient can interface with the various databases, medical professionals and pharmacies. A telemedicine professional is disposed at a loci 3504, a central office for running the entire transaction is disposed at a loci 3506, which central office can interface with two databases, a main or first central office database at a loci 3508 and a and a second central office database comprising a transaction central office database a loci 3510. The two databases at loci 3508 and 3510 are typically located at the central office but this just distinguishes that there are two databases, a main database and a transaction database. As will be described hereinbelow, the transaction database at loci 3510 is a database that stores all the information about the secure transaction to define a unique transaction ID consists of all of the transactions carried out during the diagnosis, and which unique transaction ID will then the locked this down and encrypted, such that the transaction database maintains a record of the transaction from initiation to completion independent of the information that is stored at the loci 3508 in the main database. The main database contains information that represents all of the information regarding a patient's medical history associated with any type of information stored therein, such as input medical history all the transactions that the patient has undergone, etc. the transaction database, comparison, stores all of the unique transaction IDs, each unique transaction ID containing all information associated with a particular diagnostic transaction undergone by patient/user via their mobile unit interfacing with the central office and a telemedicine professional, as will be described hereinbelow. For example, it may be that certain questions were answered in the course of the unique diagnostic transaction and these would the part of the diagnostic transaction and would be interval to the unique transaction ID, but they would also be entered into the central office main database associated with that patient and also in the central database associated with all patients as a common knowledge database. The central office at the loci 3506 can interface with a pharmacy at a loci 3512 to complete the transaction.

The transaction is initiated at the test site by a user/patient opening an application on their portable user device such as a smart phone, a mobile unit (MU). The application is opened and then the user/patient will actually select the type of transaction that they are interested in. This particular type of transaction is a diagnostic transaction and this will typically be associated with some testing platform or device. It could be a simple medical test strip or a microfluidics device. This is some type of device that can receive a biologic in the form of some type of bodily fluid from the user/patient and perform some diagnostic test specific to that particular testing platform. The user/patient can actually select the test to be performed such as the UTI from a menu or take a photograph of the particular testing device after the test is complete that would indicate the type of test associated with that testing device via some type of op the recognizable code disposed on the testing platform, such as the test strip. Of course, some testing devices might test for multiple medical conditions, for example, and some selection might have to be made by the user/patient. Further, there can be some type of electronic interface between a testing device and the phone. In any event, there is some initiation that is performed at the test site at a point 3514 by either the user/patient or automatically view the interface of the user/patient's MU and the testing device. Once the application is initiated, the user/patient's MU will then send information to the central office to initiate the application at the central office. At this point, either at the user/patient's MU or at the central office, a unique transaction ID is assigned to this particular diagnostic transaction. Initially, this unique transaction ID is merely an identifier at the initiation of the transaction and which unique transaction ID will be thereafter and subsequently populated with associated transactions, as we described hereinbelow. This unique transaction ID will typically have multiple fields associated there with, such that unique transaction ID will be defined this as a UTI test, for example.

In this particular specific sequence for carrying out a diagnostic transaction for a UTI with a specific test rep the next step is to understand what the application is, i.e., UTI, and then the central office sends preliminary questions back to the mobile device from the central office that are tailored to retrieving some preliminary information regarding some information from the user/patient there would be specific to diagnosing a UTI. These initial and preliminary questions are for the purpose of confirming that this particular UTI diagnostic test is the appropriate test for that particular patient. When the application is initiated, the central office will recognize the identity of the patient as result of some type of identification information sent back to the central office in the form of the IMSI of the phone, user login information that was required in order to open the application, etc. it may be that the user has been preregistered and all that is required is the IMSI of the phone, for example, or some type of user login information required to login to the application on the user/patient's MU and which can then be transmitted therefrom to the central office. This newly created and unique transaction ID will then be utilized to initiate the transaction in the form of storing all subsequent steps during the diagnostic transaction from initiation to completion in the central office main database and also in the central office transaction database and they will be utilized to track the entire transaction. It is noted that any information that is associated with the diagnostic transaction and which will become a secured and permanent part of the unique transaction ID associated with that diagnostic transaction will be fixed at the end of the transaction in the unique transaction ID.

For a UTI, the typical questions that would be asked of the user/patient with a query would be in the form of and inquiry as to whether the patient had pain or burning when urinating. Also, there will be some type of query as to how long this has persisted—if it only occurs once during the day and not again for the rest of the day and there are no other signs or symptoms, this is an indication that the body may have already flushed out any bacteria and the patient should not be concerned any further. The patient then may be queried as to whether frequent urination has not brought any relief or that the patient always has a sensation of a full bladder but only dribbles during urination. The patient may then be queried as to whether the urine is cloudy, bloodied or discolored. Even the color of the urine as to being off yellow or clear may be an issue and will be part of the query. Of course, there may be a query as to what types of food have been eaten during last 24 hours. Beets and other foods can cause urine to be frightening pink, orange or red, but the lack of pain will indicate that this may not be a UTI. A query may be made as to the odor of the urine, as a pungent smell is sometimes a common UTI symptom. A query may be made as to whether the urine continues to have a pungent smell after urinating a number of times and whether it is also paired with a cloudy or red color. A query may be made as to whether the patient has cramping, pressure, or abdominal pain in addition to whether they have muscle aches and fatigue. Any combination of questions will provide some preliminary information to a testing or diagnostic sequence to indicate whether it is worth going forward with the diagnostic test. This is determined at the central office at a point 3516 after the answers to the questions have been analyzed. Once they have been analyzed, and an initiation of the test is indicated, then the test is initiated by prompting the user at the user/patient's MU to take the next step in the test. This will involve, for example, a test strip on which a biofluid sample such as urine is deposited. The patient may have multiple test strips associated with such things as a UTI, strep, or any other common infection that is available. The patient may have already utilized this particular test strip and seen some indication that the results are positive. However, that information is not part of the system as of yet. At this point, the user is prompted to take a photograph of the test strip for analysis purposes. If the test strip has already been prepped with the biologic, as it may take 10 or 15 minutes for the chemical reaction, then the picture can be taken directly. However, if not, the user must then actually place a biologic on the strip and then take the photograph after the prescribed amount of time for the test results to become valid. Once the photograph is taken, this is the capture aspect which basically takes an analog output from the test strip and digitizes it to convert this to a digital information that comprises the captured image which is then transferred to the central office as the captured test. This is indicated at a point 3518. At each step, the central office database and the transaction database are updated with the results. In this manner, all the questions that are asked and all the answers will be stored in both the central office database, and transaction database in association with unique transaction ID, in addition to the results of the capture test being stored in both databases. It should be understood that any time information is stored in the transaction database, it is always stored in association with the unique transaction ID associated with the particular diagnostic transaction that is being undertaken.

Once the capture test is present at the central office database 3506, it can be analyzed and, during analysis, advertisement information can be streamed to the user at their mobile device. Typically, the user is waiting for the results of this test to confirm their suspicions and they will typically wait very patiently and watch the screen of their mobile device for a certain amount of time. Thus, there will be a certain level of attention span that is dedicated to the screen at this time, which is very desirable from an advertiser's standpoint. The analysis, of course, is almost instantaneous, but it is delayed to allow these advertisements to be streamed to the user. Of course, these are focused advertisements, since it is known who the target is, i.e., a female within a certain demographic with a certain medical history and the type of specific medical condition that may be involved. After a certain period of time, the results are then transmitted to the user/patient's MU and displayed. Of course, the results are stored in the central office database and the transaction database at the same time. At this point, the user may be prompted for requesting an interface with a telemedicine professional or the user can terminate the transaction, depending upon the results. If the transaction is terminated, this is provided as an update to the central office database and also to the transaction database. At this point, the unique diagnostic transaction is closed and the unique transaction ID is then closed to provide a fixed transaction which is then encrypted in no other transactions can be appended to this unique transaction ID. The purpose of this, for example, is that at this point in time, a patient can have certain results determined during the diagnostic transaction and was are associated with associated with the steps carried out in the diagnostic transaction for this specific medical condition, and wherein valuable information can also be provided to the user/patient in association with generally accepted standards in the medical community for processing a diagnosis for UTI. It may be that, in the future, different questions would be asked and would be considered necessary in order to adequately diagnose a UTI. However, at the time of this transaction, is important to freeze in time the questions actually asked of this particular user/patient. This can provide information that is valuable to overall system. It can also provide some type of verification of the system and these test strips in the overall test process, which will be an FDA approved testing process, and that is a have been carried out in accordance with then known and approved standards.

After the user/patient receives the results of the test, which are displays on the user/patient's MU, they then have the option fifth results are positive to interface with a telemedicine professional and, upon selection of this option, the user/patient's MU sends a request for a telemedicine professional vendor to the central office. This request is stored in the database at the Central office in association with the overall unique transaction ID and then the profile of the particular user/patient is accessed from the central office database. This particular profile for this user/patient is not really required for any of the preceding process steps required for this unique diagnostic transaction, as those preceding process steps are generally associated with just determining what the particular test is that the user/patient is utilizing and what questions should be associated with that test prior to proceeding further with unique diagnostic transaction and what analysis to perform on the particular test results it receives from the user/patient. Thus, the first step is to at least recognize what type of specific medical condition is involved, i.e., a UTI, merely from the fact that the user/patient has requested the initiation of a UTI transaction. This triggers the queries that are sent out to at least collect some preliminary medical information from the user/patient prior to receiving any test results from the testing platform. At this point in the diagnostic transaction, there will not be provided any particular diagnosis to the user/patient but, rather, the central office merely provides results from a test, i.e., is a test negative or positive, to the user/patient. At this point in time, even if the results are positive, it is up to the user/patient to select a continuation of the diagnostic transaction in the form of, for example, contacting the telemedicine professional. It could be that the next step is for the user to a select an option of transferring the results to their personal physician, which address and information is stored in the user/patient's profile at the central office. If the user/patient selects the option of initiating a session with a telemedicine professional, the next step in the diagnostic transaction is taken. However, once a telemedicine professional is involved, then the medical history, and possibly some information in profile, in some form that is associated with user/patient at the time of the transaction may be required for the process to continue. A telemedicine professional would want to know, for a UTI test for example, that this is a female, the age of that female, any past medical history, allergies, etc. that that particular user/patient may have. At a point 3522, this request triggers the storage of the request (noting that all transactions will be stored in both databases and, when stored in the transaction database, they will be stored in association with the transaction ID). An analysis based upon the particular type of transaction is then run based upon the test results and the user/patient information utilizing an expert system, as will be described hereinbelow.

At this point in the process for this particular transaction, the portion of the central office database associated with the unique transaction ID for this particular transaction is updated with the profile information for that user/patient that is required to run the analysis. As will be described hereinbelow, the analysis is basically an expert system or some type of artificial intelligence that analyzes the patient profile in terms of what information is necessary to make a recommendation regarding a therapeutic regimen to be carried out in view of the test results and the information regarding the user/patient for this specific medical condition. This recommendation is made to the telemedicine professional based upon the particular test being performed for the specific medical condition such as the UTI, the test results and any information that has been provided during the transaction or prior to the transaction and which is stored in the central office database in addition to any information regarding medical history of user/patient. The results of this analysis will be stored in both the central office database and also in the portion of the central office database associated with unique transaction ID, also noting that information regarding the actual expert system or the such that was utilized at the time of the diagnostic transaction will be stored, such that at a later time it can be verified. Once suggested treatment regimen has been determined, this information is then transferred to the telemedicine professional, as will be described in more detail hereinbelow.

Once the require information has been transferred to a telemedicine professional in accordance with the diagnostic seizure for this diagnostic transaction, this will initiate a link between the telemedicine professional and the user/patient. The central office will request a connection to the telemedicine professional by the test site by sending the information to the test site for initiating such a connection and then the connection will be made. It may also be that all connections go through the central office. This is at a point 3524. Both the telemedicine professional and the user/patient at the test site will interface with the central office to indicate that a connection has been made, as a connection in this example is a peer-to-peer connection, but also could be a managed connection, such that all communications and information must flow between the user/patient's MU and the central office, and between the central office and the telemedicine professional, with the central office controlling information sent both parties in the connection. Thus, all information regarding this connection will be transferred to the central office to allow the records regarding all aspects of this diagnostic transaction to be updated in both the central office database, and in the transaction ID database in association with the unique transaction ID for this transaction. The telemedicine professional then interacts with the test site, with any information regarding this interactive connection being communicated to the central office such that the central office database and the unique transaction ID database can be updated. During this interactive unique diagnostic transaction, certain information can be accessed from the central office database for transmission back to the telemedicine professional. This occurs at a point 3526. This interactive interface, with all information transferred to and from the test site to the telemedicine professional recorded in the respective databases in association with this unique transaction, will continue until the completion, which in this example, is the generation of a prescription at a point 3528. This operation will be interfaced to the user/patient and also to the central office for processing and updating of the respective databases. This will "trigger" the suggested prescription operation, which is suggested prescription operation was one that was determined by the expert system. All the telemedicine professional does is, after entering certain data, and asking certain questions, push a "completion" button on their screen to just accept a suggested prescription, or one of multiple suggested prescriptions. With multiple suggested prescription, the telemedicine professional can make some decision based upon their experience. The central office will then send a request to the particular pharmacy, typically a pharmacy that is preauthorized for the user/patient end there stored profile, followed by an authorization sent back to the central office database. This authorization will then be displayed to the telemedicine professional if necessary and that will be confirmed by the central office database to the pharmacy. Once the transaction has been confirmed by the pharmacy and an acknowledgment is made to the user/patient in the form of possibly sending a tracking number and a phone number for the pharmacy from which the prescription is to be filled, the file is encrypted and locked by the central office database to basically lock the unique transaction ID database for that transaction. As will be described hereinbelow, although all of the respective information for this user/patient will be updated in the central office database, all the information required for this unique transaction to be process of initiation to completion is stored in unique transaction ID database in association with and as part of this particular unique transaction ID. This will be LOC for verification purposes and later access. As such, the actual state of this entire unique diagnostic transaction will be preserved. This is important, as things change with respect to a user/patient's medical history, for example. If, at the time of a particular diagnostic transaction, the medical history of this particular user/patient indicated that the user was not a diabetic, that would be important for the expert system to determine a suggested prescription. At a later time, this could have been updated indicating that the user/patient is now a diabetic. But the state of health or medical history of the particular user/patient at the time the transaction is what is important, as that is what the system and the telemedicine professional has relied upon in order to prescribe a particular drug, such as an antibiotic. There are certain antibiotics that on the label provide some indication that they are not to be used for people with certain levels of diabetes. If the system does not know if this condition exists with respect to the particular user/patient, then this would be an acceptable antibiotic to prescribe, giving the state of knowledge available to the telemedicine professional and to the expert system at the time of the transaction. By storing all of the information that was used in all of steps of the diagnostic transaction, etc., that were involved in this diagnostic transaction, this diagnostic transaction can be locked in time to preserve all decision-making processes. Another example for this might be where the test strip were in fact changed. By having knowledge of exactly which test strip was used for this transaction in the version and date thereof, further verification can be provided as to the results of this particular test and transaction.

Figure 36:
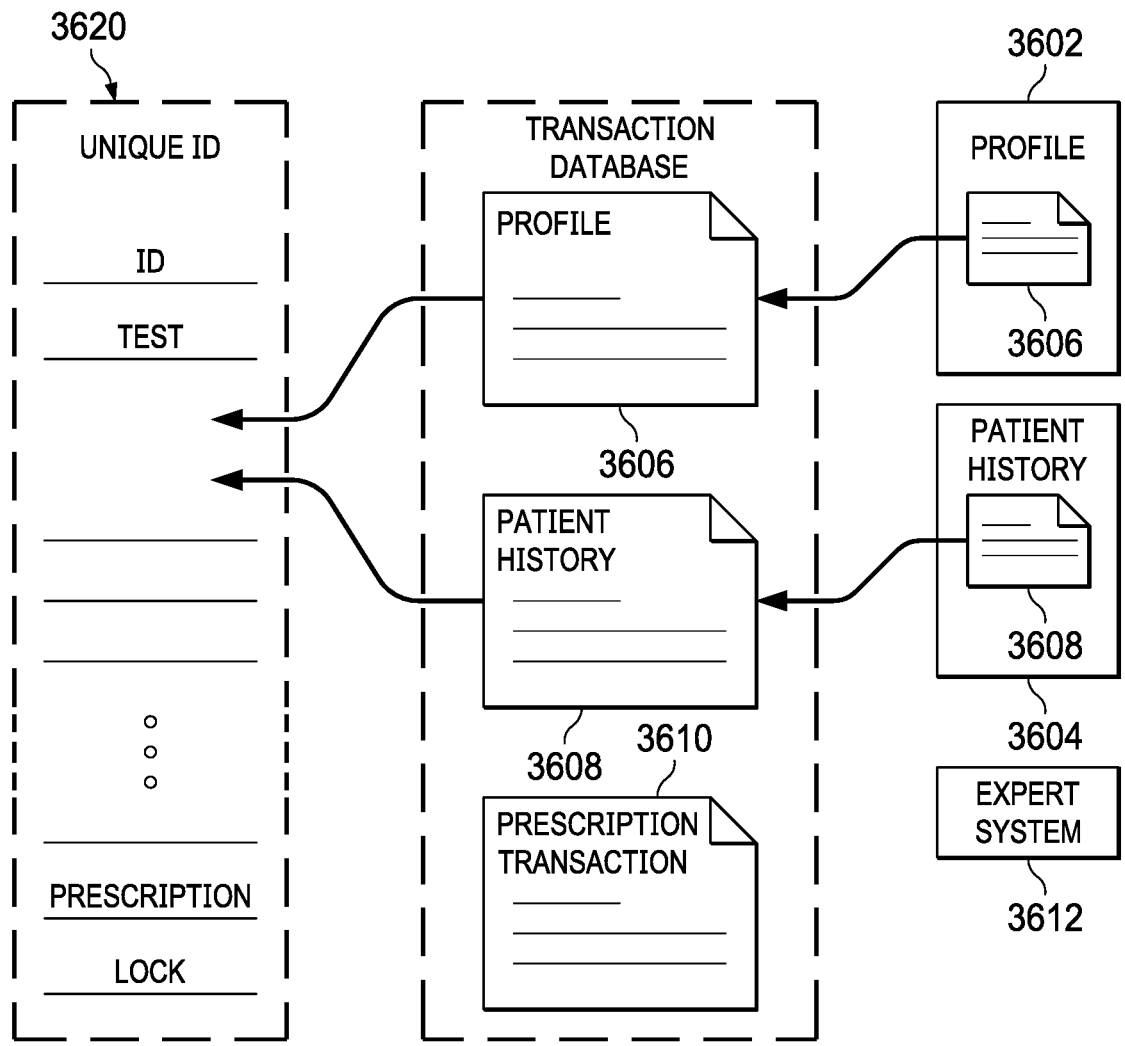
FIG. 36 illustrates a diagrammatic view of the way in which the Central Office database is updated.

Referring now to FIG. 36, there is illustrated a diagrammatic view of how this transaction database is locked and fixed time. It can be seen at the central office database can contain a profile of the particular user/patient at a block 3602. In addition, there may be patient history stored in a block 3604. Only a portion of this profile is required for this particular test, i.e., the UTI test. This information is indicated as a portion 3606 of the profile and also a portion 3608 of the patient's history. There may be certain aspects of the patient's history that are relevant to any decision on a particular test such as UTI. While a history of a previous diagnosis of irritable Bowel Syndrome (IBS), by way of example, may be relevant to a diagnosis, information with respect to an inner ear problem is probably not relevant and would not be required by the expert system or telemedicine professional, or any medical professional, in order to make a decision as to prescribing an antibiotic for UTI. Thus, only the information that is relevant to the diagnostic transaction process for the specific medical condition would be utilized. If utilized, it is actually transferred over to the transaction database for storage therein in association with this unique diagnostic transaction and in association with the particular step in the process that is being carried out. This is also the case with respect to some of the patient history. This is also indicated in a section 3610 which represents the prescription transaction which will actually be stored. This might involve some information from the user/patient's preferences that were prestored, insurance information, etc. All of this will be stored within the unique transaction database when it is access and utilize to make a decision and to bring the overall unique diagnostic transaction process to a close.

In addition, there will be provided an expert system 3612, which is used for analysis purposes. This particular expert system, as will be described hereinbelow, is a trained system, which has a defined functionality that will, based upon the inputs thereto, output some type of result. However this result is based on the actual state of the expert system at the time of its decision. If, at a later time, the trained functionality of the expert system were changed or updated, this could possibly result in a different decision. For example, if a diagnosis procedure for UTI were updated in the accepted industry standards for this diagnostic process to consider some other aspect to be important, such as travel to a foreign country, this would be some aspect that the expert system would, or possibly could, require as an input. Thus, it is important to understand the actual state of the system at the time of the transaction. It would not be necessary to store the entire expert system in the transaction database but, rather, it might be desirable to have the date and serial number for the expert system recorded, such that the state of the expert system "at the time of the unique transaction" can be determined, if necessary. The expert system has embedded therein as a result of the training thereof the functionality that is an IF-THEN functionality. Diagnostic procedures are inherently linear procedures that can be defined in terms of a series of diagnostic steps that must be taken in order to make a final decision, and which diagnostic tests operate in accordance with industry accepted standards, the overall functionality operable to yield output that, in the Presley disclose embodiment, results in the suggestion of a therapeutic regimen such as a suggestion as to what type of drugs would be applicable to treat the specific medical condition that is the subject of the overall test performed on the test platforms and resulting diagnostic procedures for this unique diagnostic transaction. There are, of course, a number of branches that can be taken along this decision process, but these branches are well defined in the expert system.

The unique transaction ID database is basically a collection of completed transactions for individual diagnostic procedures, each associated with and associated one of the unique transaction IDs. Although the unique transaction ID is something that identifies the transaction, it also contains all the information necessary to uniquely represent the unique diagnostic transaction itself and all steps that were involved in the unique diagnostic transaction. Thus, the unique transaction ID will have some type of file header or ID assigned to it initially and then it will continually change as the transaction proceeds by adding or pending such things as the test results to it, the basic profile in the patient history, etc. These are all stored uniquely in the transaction database, or linked to this unique transaction ID, or the unique transaction ID could actually contain all of this information. One preferred form is a plurality of URLs that point to unique and unchanging portions of transaction database, such that the collection sequence of the URLs uniquely define the unique diagnostic transaction. This overall collection of URLs or of data associated with the transaction constitutes the unique transaction ID. For any user/patient, a subsequent and new test will result in another unique transaction ID created.

Figure 37:
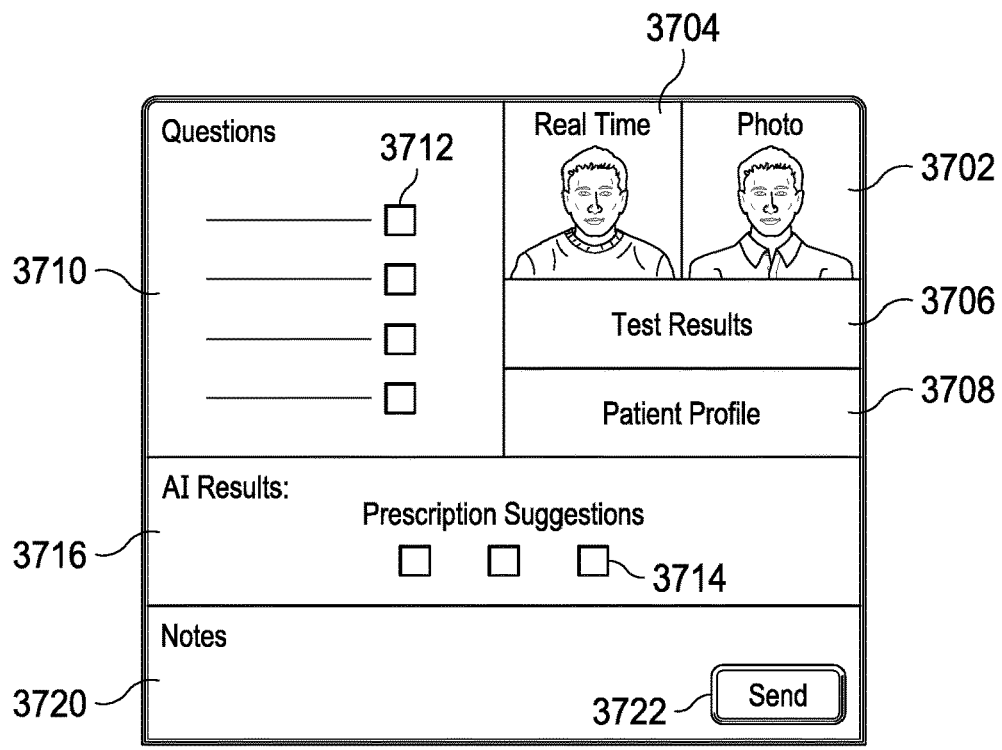
FIG. 37 illustrates a sample screen that would be presented to a telemedicine professional.

Referring now to FIG. 37, there is illustrated a diagrammatic view of the screen that would be presented to the telemedicine professional. What is important here is that the screen needs to be populated for the telemedicine professional to allow the telemedicine professional to make a decision, i.e., to prescribe a particular drug, in accordance with industry accepted standard diagnostic procedures in the medical industry for that locale an associated with diagnostic seizures associated with the specific medical condition being tested for. Information that is provided to the telemedicine professional, in this example, comprises an actual photograph of the individual in an area 3702 and even possibly a real time screen in an area 3704 to allow a video link to the user/patient via some system, such as Facetime®, Skype®, etc., to allow the telemedicine professional to actually see the individual they are talking to. It may be that this video stream will be required for verification purposes by comparing the received image with the stored image. Further, it may be that the video stream is imperative for certain types of tests, as the acceptable drugs to treat some maladies may have a higher level of verification required. Additionally, it may be that the user/patient is required to enter some type of biometrics, such as a fingerprint scan, a retinal scan or a vein scan. All of this video stream another verification information received from the user/patient, of course, will be stored as part of the unique transaction associated with the unique transaction ID in the transaction ID database. The test results will be displayed in an area 3706 and this will basically tell the telemedicine professional all the information they require regarding the test results, i.e., what type of test it is, the testing device, the results, etc. There will be provided in an area 3708 pertinent patient profile information that would be relevant to the specific medical condition tested for to assist a telemedicine professional in completing a diagnosis and selecting from the determined drug therapy regimen provided by the expert system. As with any diagnostic procedure, there are industry acceptable standards that must be followed in making such a diagnosis. The expert system will be trained on these standards and have them embedded in the functionality thereof and will, based upon the results and the patient history, etc., present a series of questions that would be required by the telemedicine professional to be asked of the user/patient and answered-these potentially just being boilerplate questions that are part of the industry accepted standards. These are in an area 3710. These are questions that may be required to be asked in accordance with acceptable standards in the medical industry for this particular specific medical condition being tested for, such as UTI, the audio of which will be stored in the transaction ID database in association with the unique transaction ID for this transaction. There are provided check boxes 3712 associated with each of these questions that the telemedicine professional will check to indicate they have been asked and answered. It may be that the audio would not be required; rather, just the confirmation of the checkmark. Of course, it should be understood that the information regarding this particular telemedicine professional and their credentials would have been approved in order to interface with the particular telemedicine professional in the connection process. These credentials, of course, would also be stored in association with the unique transaction ID in the transaction ID database.

The expert system would provide some artificial intelligence (AI) for this operation and it might modify the questions to be asked depending upon information regarding the particular medical history or information provided in the initial questions asked by the system of the user/patient. For example, the questions provided for a woman may be different than for a man. The purpose of the questions in area 3710 is merely to comply with certain industry accepted standards with respect to this particular UTI, for example The expert system would have already determined that, in response to a positive response to each of the questions and of course the positive results, potential suggestions for a treatment therapy regimen, such as a drug therapy. These potential treatment therapy regimen suggestions would be presented in an area 3716 with selectable boxes 3714. If multiple regimens are available, they would be ranked, for example, for selection by the telemedicine professional, i.e., if the expert system determined that there are three drugs that are potentially available, they might be provided in this area and rank in accordance with their suitability to the specific medical condition being tested for and also as a condition of user preferences. The telemedicine professional could then provide some notes, if necessary, in an area 3720 and then, upon completion of the questions and selection of one of the treatment therapy regimens such as drugs suggested by the expert system, a "send" button 3722 is then depressed to indicate that the telemedicine session has been completed and the treatment therapy regimen selected sent back to the central office. Although not shown, there could also be a "cancel" button that would indicate that the test results did not indicate there was a UTI, for example. The depression of the "send" button will then trigger the prescription process, which is really outside of the decision process for the telemedicine professional. How it could be filled or when it actually is filled is the responsibility of the central office and the prescription preferences that were previously provided by the user/patient. It could be that the user/patient is presented with the ability to select at the mobile device between picking up the prescription at their doctor's office, having the prescription filled by their preferred provider the next morning or even have a service deliver the prescription within a very short period of time for a premium. Some services can deliver the prescription, depending upon the prescription, within one or two hours. This might be desirable for a mother having gone through this particular transaction for strep throat in a child as an example. That mother may want to have the antibiotics delivered as soon as possible in that situation.

Figure 38:
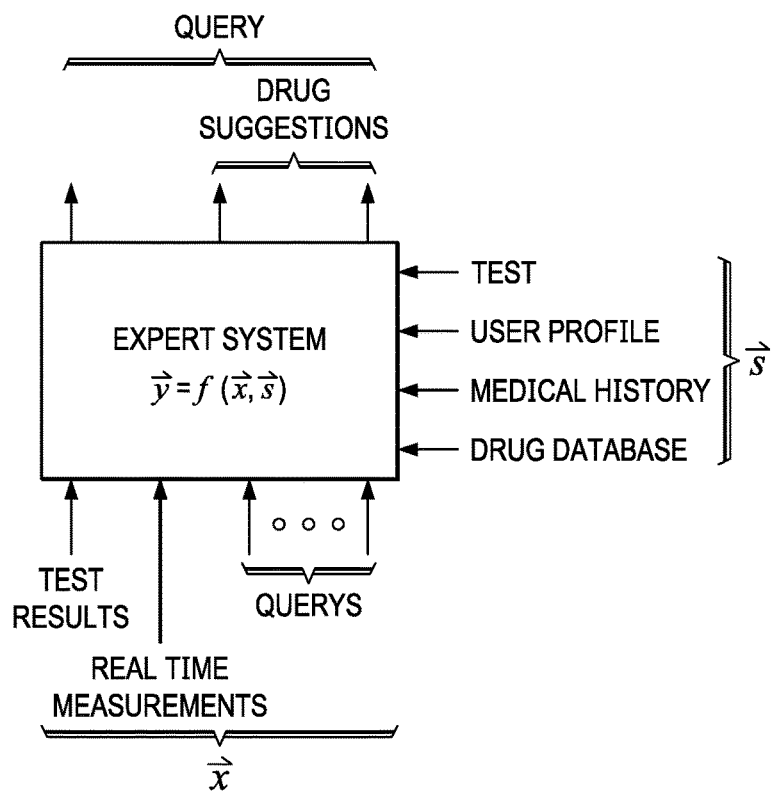
FIG. 38 illustrates a block diagram of an expert system.

Referring now to FIG. 38, there is illustrated a diagrammatic view of an expert system. An expert system is basically a system that is trained on a knowledge base of a given expert in the industry. The knowledge base for the medical industry consists of the accepted and standard specific diagnostic procedures associated with the specific medical condition that is the subject of the test platform upon which the biologic has been applied and which is the subject of the test results, if any. These are the diagnostic procedures required by a medical professional to interface with the patient and diagnose the specific medical condition being tested for, i.e., a UTI, and then prescribe a therapeutic regimen, such as a drug.

For the present system, the particular test that is performed, i.e., that associated with the test platform such as the test strip, that test strip associated with a UTI, defines the diagnostic procedure. Expert systems can take many forms, those associated with a linear system and those associated with a nonlinear system. Nonlinear systems are utilized in some instances to model a system on a set of data, such that a prediction can be made when data actually not in the original set of training data is presented to it. Such things as neural networks are examples of nonlinear modeling systems. However, for the present expert systems, a linear system such as a first principles engine is utilized. A first principles engine operates on a be determined formula wherein, for a given set of inputs within a finite set of inputs, there is an output. This is a defined function that is embedded within the engine and requires the inputs to exist within that finite set of inputs. For example, there will be provided a vector of values $\vec{x}$ that represent the finite set of variable inputs of the system such as test results, the input questions that were presented to the user at the time of the test initiation, biological readings such as blood pressure, temperature, etc. that can vary. Vector of state variables $\vec{s}$ is provided that represent fixed information defining the state of the system at the time of operation, such state variables being the test that is being performed, for example. The output is a vector $\vec{y}$ that represents the output for that particular operation of the system under those state variables. For example, if the test were a UTI test, the expert system would be "parameterized" for that test. This parameterization would configure the expert system for a particular test and for such things in the user profile such as the gender, age, etc. of the user/patient. The expert system could also be configured with information accessed from a drug database for any drugs that would be associated with any type of diagnosis for a UTI, for example. Thus, the expert system would then be predisposed to only make decisions regarding selection of one of potentially multiple drugs that are available for treating a UTI and make those decisions in a linear fashion based upon the results of the test and the results of any of the queries made of the user/patient upon initiation of the overall testing procedure. Additionally, it may be that the user/patient has indicated a preference for generic drugs versus brand name drugs or that they want to select the lowest price, and the expert system can make this determination, as that is one of the inputs that can be provided to the expert system. Since the industry acceptable standards in the medical industry are very linear in nature and follow a prescribed pattern, they can be embedded within the function of the expert system, $\vec{y}=f(\vec{x},\vec{s})$. Knowing that the results of the test are positive and having knowledge of information regarding the user/patient and possibly some input information from wearables that the user/patient may be capable of providing through their mobile device, a set of questions can be provided as an output in addition to one or more suggestions as to which drug would applicable. These questions will typically be provided in some type of lookup table. As noted hereinabove, the expert system may be able to interface with the drug database to select the drug based upon both the test results and the medical history of the user/patient and possibly the preferences of the user/patient. If the user/patient is an elderly person, a woman that has diabetes, the drug selection may be different than if that user/patient was a young woman with no indication of diabetes. It is also important to note that this diagnosis could change as a result of the acceptable industry standards for the diagnostic procedure changing, i.e., some additional information regarding the actual temperature of the patient at the time of the test being required in the future after the current test has been performed, as opposed to just the fact that there is presently required only the existence of a high bacteria level in the urine. The standards could also be changed with respect to the particular drugs that could be selected based upon some additional facts being known about drugs that have side effects that change in the future. Thus, it is important that, at the time of the diagnosis, the parameters of expert system, the inputs to the expert system and the function of the expert system be fixed in the unique transaction ID database associated with that unique transaction ID. If, for the purposes of later verification of the particular transaction which resulted in a prescription of a particular drug, it were necessary to review the overall transaction, it would be important to review exactly what happened at that time, and it would be important to have knowledge of the decision-making process, i.e., how exactly did the expert system analyze the information that it was presented and what information was presented. By knowing the configuration of the expert system, i.e., what exactly the embedded function $\vec{y}=f(\vec{x},\vec{s})$ represented at that point in time, the exact circumstances of the transaction associated with that unique transaction ID could be replicated and verified. Since all the inputs of the expert system are mapped through that functionality to provide an output, it is necessary to know the functionality and the actual inputs that were processed therethrough at the time of the transaction. Since the data associated with that unique transaction ID, which data represents the unique transaction ID, is "locked," and encrypted, this is a highly protected unique ID.

Figure 39:
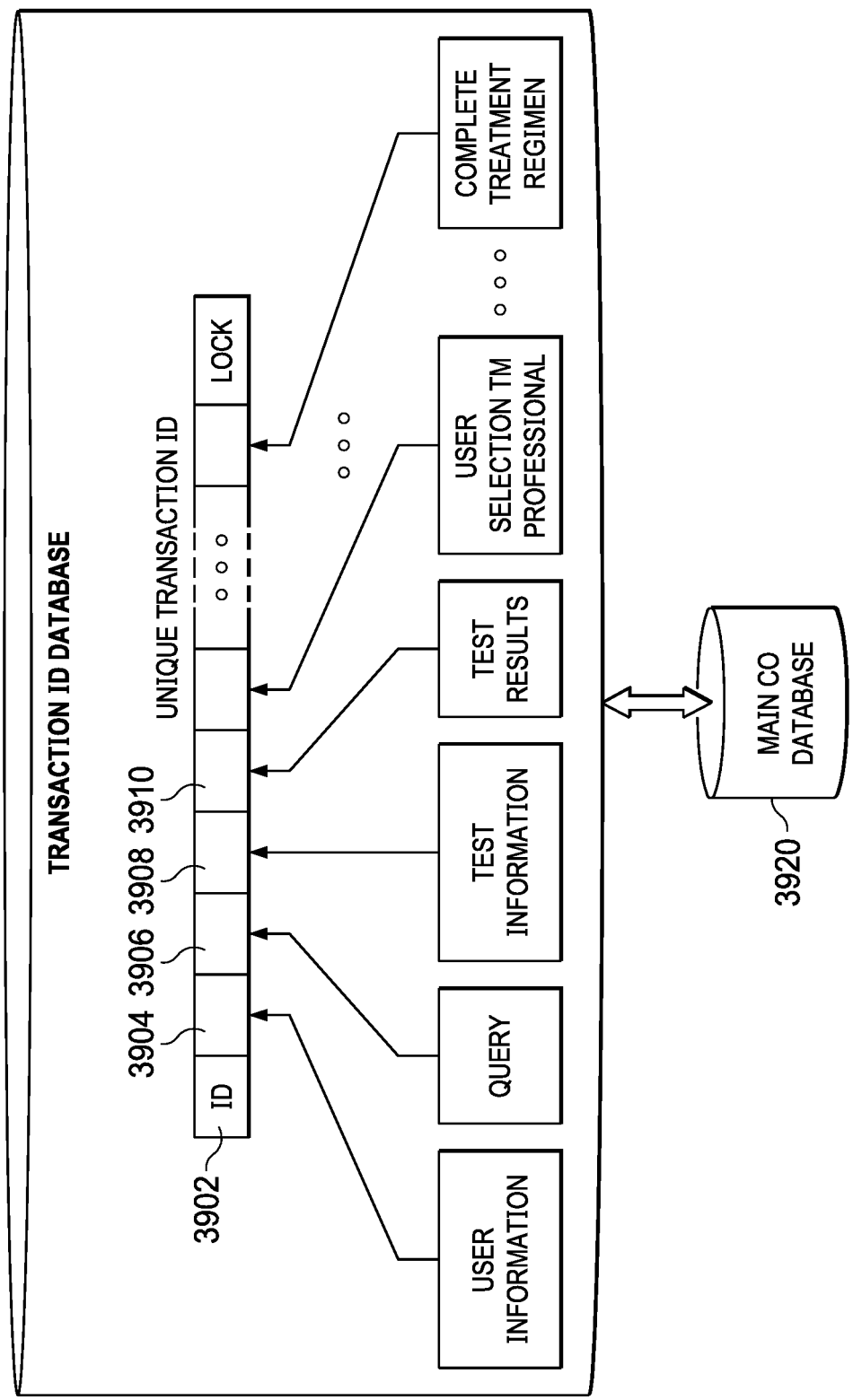
FIG. 39 illustrates a diagram of the unique transaction ID.

Referring now to FIG. 39, there is illustrated a diagram of the unique transaction ID. The unique transaction ID is initiated with an assigned identifier in a field 3902. This basically is an identifier assigned by the system for the purpose of storing the information in the transaction ID database at the central office. Thereafter, the data collected during the transaction is added into fields in the unique transaction ID. This data may actually be a URL that points to a particular stored pieces of information within the transaction ID database. Is important to note that this information will be stored in a secure manner such that it cannot be changed. Thus, if, at a later time, the URL were utilized to point to a location within the transaction ID database, the information that it would pull up would be the information that was stored in the transaction ID database at the time of the transaction. For example, the next field might be the user information that was transferred to the central office upon the initiation of the application. This could be stored in the field 3904 or there could be a URL pointing to the information in the transaction ID database. This information actually may be identical if the same user/patient had undergone multiple transactions using the exact same user information in the very first step, but it will be uniquely stored multiple times, once for each of the unique transaction IDs it is associated with, even if it is identical. The next field, a field 3906 could be associated with the information that was part of the initial query sent to the user/patient as a result of the user/patient initiating on their mobile unit or phone the transaction for the specific medical condition, i.e., a UTI, for example. A next and subsequent field 3908 could be associated with the test information that was transmitted to the central office and then a subsequent field 3910 associated with the actual test results sent back to the user/patient. Is important to note that the sequence of fields and how they are populated will be substantially the same for any user/patient that initiates a transaction for the same specific medical condition that is being tested for, i.e., a UTI, and utilizing the same test platform. However, there might be different fields dispersed therethrough, as the diagnostic procedure could have different branches. As noted hereinabove, there could be certain things in the medical history of an individual that would cause additional decisions to be made, these decisions again being those associated with standard medical practices. And there may be certain user preferences that cause different branches to be taken. As another example, consider that the expert system had determined that, due to the test results and other information based upon the answers to the questions, the user/patient should go directly to a hospital rather than just prescribe a drug treatment regimen. This would, of course, require a different branch and a different decision to be made. However, this sequence of fields is a linear sequence that, for another user/patient that had substantially the same results, the same symptoms and answers the query in an identical manner, would result in a substantially identical user transaction ID, with the exception that there would be different information in there such as the user information, the identifier, etc. It will still be a unique transaction ID in the transaction ID database and information stored in association with that the transaction ID would be unique and permanently stored and secured in association there with. All of the data will be mirrored in the main central office database 3920 for the purpose of updating the various medical history portions associated with a user/patient, providing historical data for analyzing trends, etc. It is important to note that, however, the transaction ID database is separate and apart from the main central office database 3920 such that, even though the information is stored in the main central office database, it is also stored in the transaction ID database in association with one or more of the unique transaction IDs. Of course, there will be information in the main central office database to allow a user to be associated with various unique transaction IDs in the transaction ID database.

Figure 40:
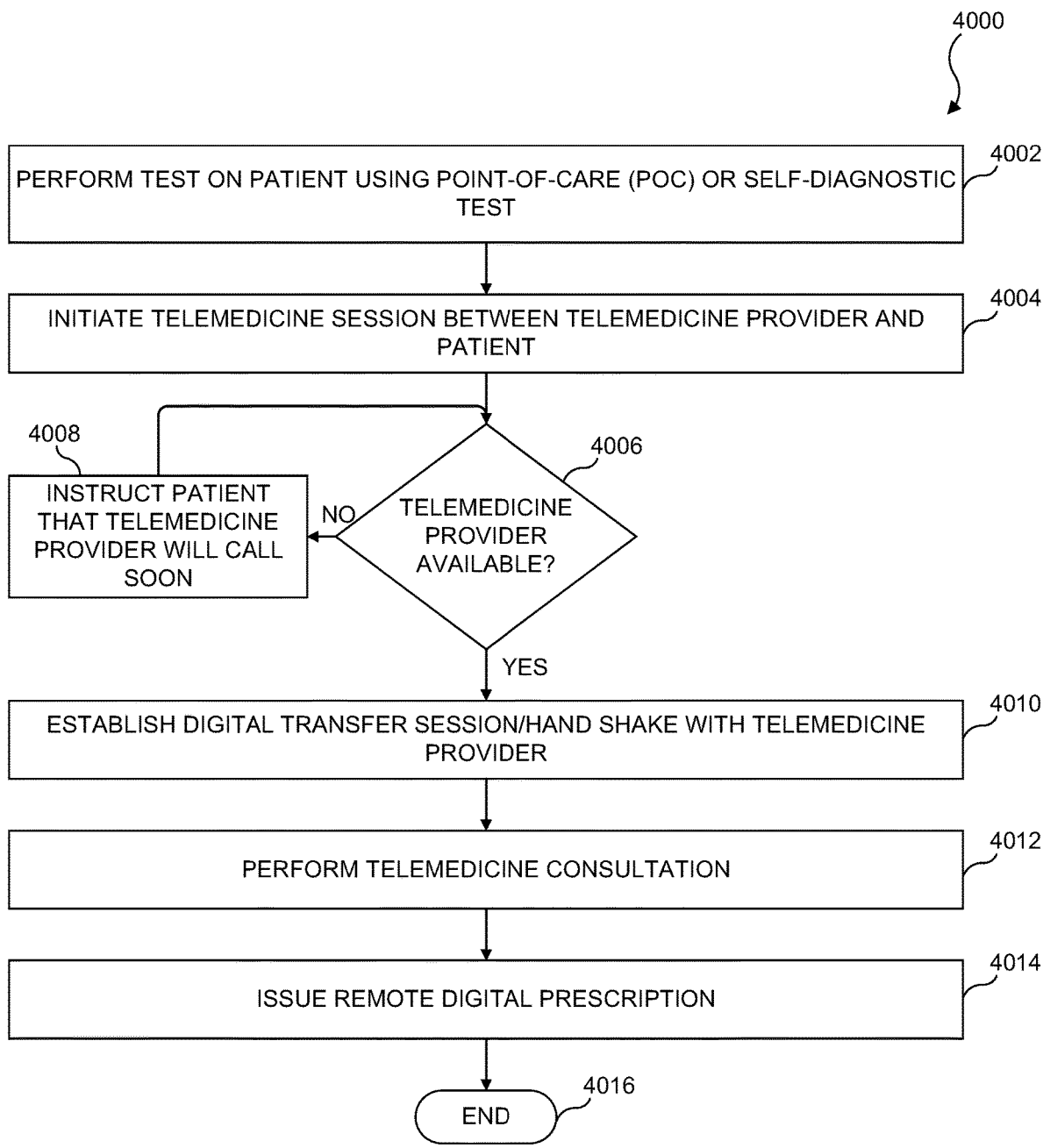
FIG. 40 illustrates a flowchart of one embodiment of a telemedicine initiation process.

FIG. 40 illustrates a flowchart of one embodiment of a telemedicine initiation process 4000. The process 4000 begins at step 4002. At step 4002, a test is performed on a patient using a POC or self-diagnostic test. For example, a patient may have received the self-diagnostic test from a retailer such as Wal-Mart or CVS, or from a pharmacy. The self-diagnostic test may have software associated therewith for conducting the test and for other operations described herein. At step 4004, in response to conducting the test, a telemedicine session is initiated between a telemedicine provider and a patient. The telemedicine session may be triggered by simply the taking of a photograph of the diagnostic test, without any analysis or results being yet provided. At decision block 4006, it is determined whether the telemedicine provider is available. If not, the process moves to step 4008, where the software instructs the patient that a telemedicine provider will call soon. For example, the application display a message that a telemedicine provider will call the patient in approximately five minutes. The process then moves back to decision block 4006. If at decision block 4006 a telemedicine provider is available, the process moves to step 4010, where a digital transfer session and/or hand shake with the telemedicine provider is established. At step 4012, a telemedicine consultation is performed by the telemedicine provider for the patient. For example, the telemedicine provider may review the image taken of the diagnostic test, and provide an opinion or advice to the patient. If warranted, the telemedicine provider may at step 4014 issue a remote digital prescription for the patient. The process 4000 then ends at step 4016.

It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A method for creating a unique transaction ID (UTID) securely representing a medical diagnostic transaction between a user/patient and a telemedicine professional, comprising the steps of:

receiving, at a central office from a user/patient's mobile unit (MU), test information generated by a test platform proximate the user/patient's MU of a biologic received from the user/patient, to initiate a new diagnostic transaction, wherein the information generated by the test platform includes a representation of positive results of a specific medical condition and information regarding the test platform, wherein the information regarding the test platform includes an indication of the specific medical condition tested by the test platform;
the central office having a first central office database for storing medical information and profile information for a plurality of users/patients, the central office having a second central office database for storing UTIDs;
initiating generation of a UTID for the new diagnostic transaction initiated by the receiving operation after creation thereof in the second central office database, wherein the UTID stores, as part of the UTID, transaction information including the positive results and the information regarding the test platform, and wherein the UTID is associated with the user/patient;
analyzing the received test information to determine if the test information for the specific medical condition being tested represents a positive result for an existence of the specific medical condition;
transferring test results back to the user/patient's MU for display to the user/patient;
updating the UTID in response to receiving additional information generated by another test platform, wherein the additional information includes a representation of positive results of a specific medical condition and information regarding the other test platform, wherein the information regarding the other test platform includes an indication of the specific medical condition tested by the other test platform, and wherein the UTID is configured to be updated to store, as a part of the UTID, information on a plurality of transactions upon an occurrence of each of the plurality of transactions; and
receiving from the MU a request for a telemedicine professional session limited to the specific medical condition being tested and in response thereto executing the following steps at the central office representing a diagnostic procedure for the specific medical condition following predetermined industry standard diagnostic procedures for such diagnosis for the specific medical condition:
  analyzing the test results with an expert system in view of user/patient stored information in the first central office database to determine at least one treatment regimen for the specific medical condition, the expert system being trained on the predetermined industry standard diagnostic procedures associated with the diagnostic procedures for the specific medical condition and for generating a result of a suggested industry recommended treatment regimen,
  generating a digital certificate, wherein the digital certificate includes the UTID and information associated with the UTID, user/patient authentication information, test results information, determined treatment regimens determined by the expert system, and expiration information, wherein the expiration information indicates a time when a validity of the digital certificate expires,
  encrypting the digital certificate using an encryption key, wherein the encrypted digital certificate is only decrypted by a decryption key made available to partnered telemedicine providers,
  contacting a telemedicine professional and transmitting predetermined information from the first central office database including at least the encrypted digital certificate,
  receiving interactions between the telemedicine professional and the user MU,
  receiving approval from the telemedicine professional of a selection of the determined treatment regimen determined from at least responses from the user/patient by the telemedicine professional through the user/patient's MU in addition to the determined treatment regimens for the specific medical condition provided by the expert system or from stored preferences of the user/patient stored in the first central office database that define an appropriate action to be taken to complete an approved treatment regimen approved by the telemedicine professional for the specific medical condition, and
  locking the UTID to prevent additional transaction information from being appended thereto during the telemedicine professional session.

2. The method of claim 1, and further comprising:
initiating an application on the user/patient's MU;
determining at the user/patient's MU the specific medical condition to be tested for;
accessing the first central office database and transmitting thereto information regarding the specific medical condition to be tested for and user information; and
the central office initiating the new diagnostic transaction and requesting test information, after which the step of initiating the generation of the UTID is performed.

3. The method of claim 2, and further comprising the steps of, prior to the central office requesting test information, generating queries and sending the generated queries to the user/patient at the user/patient's MU, the central office receiving responses to the generated queries from the user/patient's MU and, thereafter, requesting test information.

4. The method of claim 1, wherein the test information comprises a digitized form of analog test information generated by and received from the test platform proximate the user/patient's MU.

5. The method of claim 1, wherein the test platform comprises a test strip that is operable to receive a biologic and provide a color indication indicating the test results, which color indication is digitized as the test information.

6. The method of claim 1, wherein the test platform comprises a microfluidic device having specified target regions there on or providing test information.

7. The method of claim 1, wherein the determined treatment regimen comprises a drug regimen and the drug regimen comprises at least one drug that can be suggested for treatment of the specific medical condition.

8. The method of claim 7, wherein the drug regimen comprises at least multiple drugs that can be suggested for treatment of the specific medical condition by the expert system.

9. The method of claim 1, wherein the predetermined information provided to the telemedicine professional in the step of contacting the telemedicine professional comprises at least a portion of a medical history of the user/patient relevant to the specific medical condition and the diagnostic procedures associated therewith and at least a portion of the profile information of the user/patient relevant to the specific medical condition and the diagnostic procedures associated therewith.

10. The method of claim 1, and further comprising the step of generating advertising information and transmitting the advertising information to the user/patient's MU between the step of receiving at the central office from the user/patient's MU the test information and the step of transmitting the test results thereto, such that a delay between the step of analyzing and transmitting is generated for the purpose of providing advertising to the user/patient.

11. The method of claim 1, wherein the expert system has a defined functionality with an input vector of variables to process through a trained functionality to provide an output and wherein the defined functionality at the time of the new diagnostic transaction being conducted and the UTID being created is fixed within the UTID.

12. A system for creating a unique transaction ID (UTID) securely representing a medical diagnostic transaction between a user/patient and a telemedicine professional, comprising:
 a first central office database configured to store medical information and profile information for a plurality of users/patients;
 a second central office database configured to store UTIDs;
 a memory; and
 a processor coupled to the memory, wherein the processor is configured to:
 receive, from a user/patient's mobile unit (MU), test information generated by a test platform proximate the user/patient's MU of a biologic received from the user/patient, to initiate a new diagnostic transaction, wherein the information generated by the test platform includes a representation of positive results of a specific medical condition and information regarding the test platform, wherein the information regarding the test platform includes an indication of the specific medical condition tested by the test platform;
 initiate generation of a UTID for the new diagnostic transaction initiated by the receive operation after creation thereof in the second central office database, wherein the UTID stores, as a part of the UTID, transaction information including the positive results and the information regarding the test platform, and wherein the UTID is associated with the user/patient;
 analyze the received test information to determine if the test information for the specific medical condition being tested represents a positive result for an existence of the specific medical condition;
 transfer test results back to the user/patient's MU for display to the user/patient;
 update the UTID in response to receiving additional information generated by another test platform, wherein the additional information includes a representation of positive results of a specific medical condition and information regarding the other test platform, wherein the information regarding the other test platform includes an indication of the specific medical condition tested by the other test platform, and wherein the UTID is configured to be updated to store, as a part of the UTID, information on a plurality of transactions upon an occurrence of each of the plurality of transactions; and
 receive from the MU a request for a telemedicine professional session limited to the specific medical condition being tested and in response thereto executing the following steps representing a diagnostic procedure for the specific medical condition following predetermined industry standard diagnostic procedures for such diagnosis for the specific medical condition:
  analyze the test results with an expert system in view of user/patient stored information in the first central office database to determine at least one treatment regimen for the specific medical condition, the expert system being trained on the predetermined industry standard diagnostic procedures associated with the diagnostic procedures for the specific medical condition and for generating a result of a suggested industry recommended treatment regimen for the specific medical condition,
  generate a digital certificate, wherein the digital certificate includes the UTID and information associated with the UTID, user/patient authentication information, test results information, determined treatment regimens determined by the expert system, and expiration information, wherein the expiration information indicates a time when a validity of the digital certificate expires,
  encrypt the digital certificate using an encryption key, wherein the encrypted digital certificate is only decrypted by a decryption key made available to partnered telemedicine providers,
  contact a telemedicine professional and transmitting predetermined information from the first central office database including at least the encrypted digital certificate,
  receive interactions between the telemedicine professional and the user MU,
  receive approval from the telemedicine professional of a selection of the determined treatment regimen determined from at least responses from the user/patient by the telemedicine professional through the user/patient's MU in addition to the determined treatment regimens provided by the expert system or from stored preferences of the user/patient stored in the first central office database that define an appropriate action to be taken to complete an approved treatment regimen approved by the telemedicine professional for the specific medical condition, and
  lock the UTID to prevent additional transaction information from being appended thereto during the telemedicine professional session.

13. The system of claim 12, wherein the processor is further configured to:
 initiate an application on the user/patient's MU;
 determine at the user/patient's MU the specific medical condition to be tested for;
 access the first central office database and transmit thereto information regarding the specific medical condition to be tested for and user information; and
 initiate the new diagnostic transaction and requesting test information, after which the step of initiating the generation of the UTID is performed.

14. The system of claim 13, wherein the processor is further configured to:
 prior to requesting test information, generate queries and sending the generated queries to the user/patient at the user/patient's MU; and
 receive responses to the generated queries from the user/patient's MU and, thereafter, request test information.

15. The system of claim 12, wherein the test information comprises a digitized form of analog test information generated by and received from the test platform proximate the user/patient's MU.

16. The system of claim 12, wherein the determined treatment regimen comprises a drug regimen and the drug regimen comprises at least one drug that can be suggested for treatment of the specific medical condition.

17. The system of claim 16, wherein the drug regimen comprises at least multiple drugs that can be suggested for treatment of the specific medical condition by the expert system.

18. The system of claim 12, wherein the predetermined information provided to the telemedicine professional comprises at least a portion of a medical history of the user/patient relevant to the specific medical condition and the diagnostic procedures associated therewith and at least a portion of the profile information of the user/patient relevant to the specific medical condition and the diagnostic procedures associated therewith.

19. The system of claim 12, wherein the processor is further configured to:
  generate advertising information and transmitting the advertising information to the user/patient's MU between the step of receiving at the central office from the user/patient's MU the test information; and
  transmit the test results thereto, such that a delay between the analyzing and the transmitting is generated for the purpose of providing advertising to the user/patient.

20. The system of claim 12, wherein the expert system has a defined functionality with an input vector of variables to process through a trained functionality to provide an output and wherein the defined functionality at the time of the new diagnostic transaction being conducted and the UTID being created is fixed within the UTID.

* * * * *